(12) United States Patent
Martins et al.

(10) Patent No.: US 12,070,601 B2
(45) Date of Patent: Aug. 27, 2024

(54) STIMULATION SYSTEM FOR EXERCISING DIAPHRAGM AND METHOD OF OPERATION THEREOF

(71) Applicant: Pinnacle Bionics, Inc., Commack, NY (US)

(72) Inventors: Antonio Garcia Martins, Ronkonkoma, NY (US); Don Headley, Scottsdale, AZ (US)

(73) Assignee: PINNACLE BIONICS. INC., Commack, NY (US)

( * ) Notice: Subject to any disclaimer, the term of this patent is extended or adjusted under 35 U.S.C. 154(b) by 0 days.

(21) Appl. No.: 15/202,463

(22) Filed: Jul. 5, 2016

(65) Prior Publication Data
US 2016/0310730 A1    Oct. 27, 2016

Related U.S. Application Data

(63) Continuation-in-part of application No. 14/941,422, filed on Nov. 13, 2015, now abandoned, which is a (Continued)

(51) Int. Cl.
*A61N 1/36* (2006.01)
*A61M 16/00* (2006.01)
(Continued)

(52) U.S. Cl.
CPC ....... *A61N 1/3601* (2013.01); *A61M 16/0051* (2013.01); *A61N 1/0456* (2013.01); *A61N 1/0551* (2013.01); *A61N 1/36017* (2013.01); *A61N 1/36031* (2017.08); *A61N 1/36034* (2017.08); *A61M 2016/0027* (2013.01); *A61M 2016/0039* (2013.01); *A61M 2016/0042* (2013.01); *A61M 2205/332* (2013.01); *A61M 2205/3375* (2013.01); *A61M 2205/3569* (2013.01); *A61M 2205/3584* (2013.01); *A61M 2205/3592* (2013.01); *A61M 2205/50* (2013.01); *A61M 2205/502* (2013.01);
(Continued)

(58) Field of Classification Search
CPC .......................... A61N 1/3601; A61N 1/36017
See application file for complete search history.

(56) References Cited

U.S. PATENT DOCUMENTS

| 3,478,746 A | 11/1969 | Greatbatch |
| 4,750,499 A | 6/1988 | Hoffer |

(Continued)

FOREIGN PATENT DOCUMENTS

WO    WO 2013/188965    12/2013

*Primary Examiner* — Rex R Holmes
*Assistant Examiner* — Jennifer L Ghand
(74) *Attorney, Agent, or Firm* — Thorne IP, PLLC; Gregory L. Thorne

(57) ABSTRACT

An apparatus for reducing ventilation induced diaphragm disuse in a patient receiving ventilation support from a mechanical ventilator (MV), including: an electrode array of first and second types and comprising a plurality of electrodes configured to stimulate a phrenic nerve of the patient; and at least one controller configured to: identify a type of electrode array from at least two different types, generate a stimulus signal for stimulating a phrenic nerve of the patient based upon the identity of the electrode type.

20 Claims, 31 Drawing Sheets

Related U.S. Application Data continuation of application No. 14/673,470, filed on Mar. 30, 2015, now abandoned.

(60) Provisional application No. 61/972,093, filed on Mar. 28, 2014.

(51) Int. Cl.
 *A61N 1/04* (2006.01)
 *A61N 1/05* (2006.01)

(52) U.S. Cl.
 CPC . *A61M 2205/581* (2013.01); *A61M 2205/583* (2013.01); *A61M 2205/8206* (2013.01); *A61M 2210/1014* (2013.01); *A61M 2230/202* (2013.01); *A61M 2230/205* (2013.01); *A61M 2230/50* (2013.01); *A61M 2230/63* (2013.01); *A61M 2230/65* (2013.01)

(56) References Cited

U.S. PATENT DOCUMENTS

| | | | |
|---|---|---|---|
| 4,944,088 A | 7/1990 | Doan | |
| 5,954,761 A | 9/1999 | Machek | |
| 6,006,134 A | 12/1999 | Hill | |
| 6,014,584 A * | 1/2000 | Hofmann | A61N 1/0502 604/21 |
| 6,032,064 A * | 2/2000 | Devlin | A61B 5/282 600/383 |
| 7,302,296 B1 | 11/2007 | Hoffer | |
| 7,303,422 B2 | 12/2007 | Hoffer | |
| 7,636,602 B2 | 12/2009 | Fassio | |
| 7,840,270 B2 | 11/2010 | Ignagni | |
| 7,962,215 B2 | 6/2011 | Ignagni | |
| 8,195,297 B2 | 6/2012 | Penner | |
| 8,233,987 B2 | 7/2012 | Gelfand | |
| 8,244,359 B2 | 8/2012 | Gelfan | |
| 8,406,885 B2 | 3/2013 | Ignagni | |
| 8,428,726 B2 | 4/2013 | Ignagni | |
| 8,478,412 B2 | 7/2013 | Ignagni | |
| 8,515,545 B2 | 8/2013 | Trier | |
| 8,571,662 B2 | 10/2013 | Hoffer | |
| 8,571,663 B2 | 10/2013 | Weisfeldt | |
| 8,634,915 B2 | 1/2014 | McCabe | |
| 8,649,866 B2 | 2/2014 | Brooke | |
| 8,676,323 B2 | 3/2014 | Ignagni | |
| 8,700,150 B2 | 4/2014 | Demmer | |
| 8,706,236 B2 | 4/2014 | Ignagni | |
| 9,050,005 B2 | 6/2015 | Ignagni | |
| 9,079,016 B2 | 7/2015 | Ignagni | |
| 9,138,580 B2 | 9/2015 | Ignagni | |
| 9,242,088 B2 | 1/2016 | Thakkar | |
| 9,682,235 B1 * | 6/2017 | O'Mahony | A61M 16/0875 |
| 2006/0247729 A1 * | 11/2006 | Tehrani | A61N 1/3601 607/42 |
| 2007/0293918 A1 * | 12/2007 | Thompson | A61N 1/36021 607/72 |
| 2010/0036451 A1 | 2/2010 | Hoffer | |
| 2010/0319691 A1 * | 12/2010 | Lurie | A61M 16/201 128/203.12 |
| 2011/0190845 A1 * | 8/2011 | Weisfeldt | A61B 5/04001 607/42 |
| 2014/0039286 A1 | 2/2014 | Hoffer | |
| 2014/0277244 A1 | 9/2014 | Rockweiler | |
| 2014/0277280 A1 | 9/2014 | Saha | |
| 2014/0309538 A1 | 10/2014 | More | |
| 2015/0045848 A1 * | 2/2015 | Cho | A61B 5/0809 607/18 |
| 2015/0231399 A1 | 8/2015 | Demmer | |
| 2015/0231400 A1 | 8/2015 | Demmer | |
| 2015/0265833 A1 * | 9/2015 | Meyyappan | A61B 5/08 128/204.21 |
| 2015/0265840 A1 | 9/2015 | Ghosh | |
| 2015/0302539 A1 * | 10/2015 | Mazar | G08B 21/0211 705/3 |

* cited by examiner

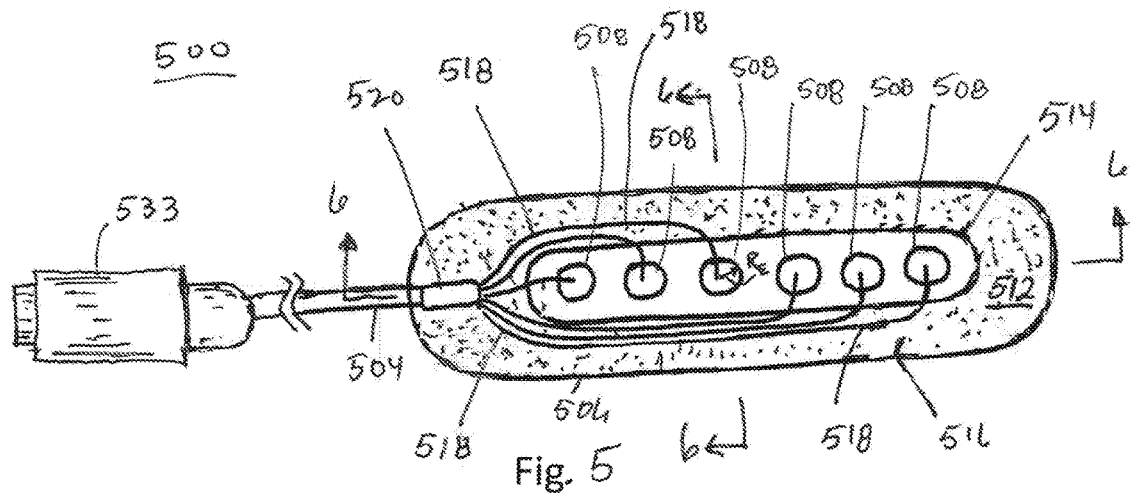
Fig. 5
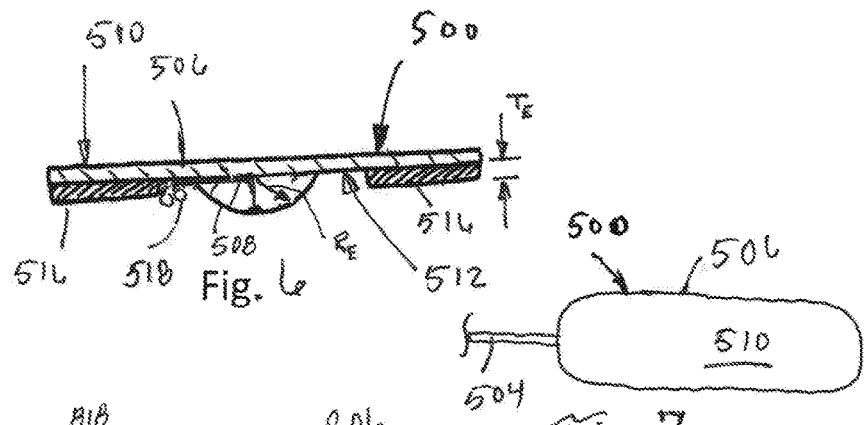
Fig. 6
Fig. 7
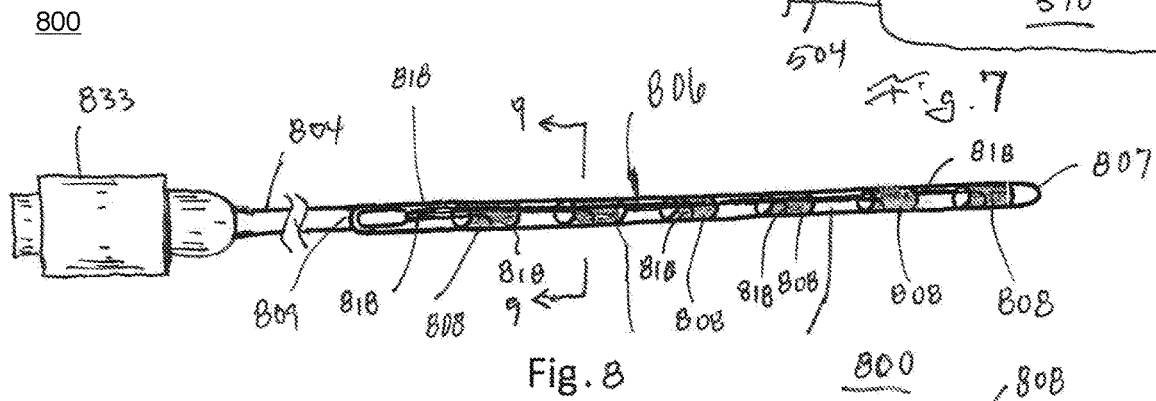
Fig. 8
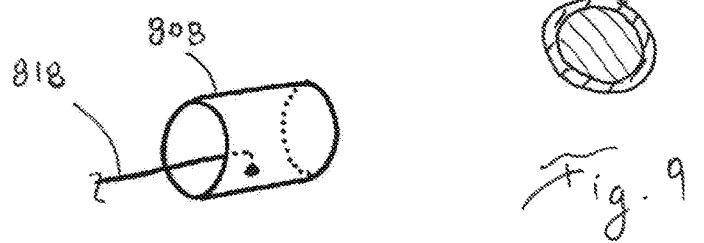
Fig. 9
Fig. 10

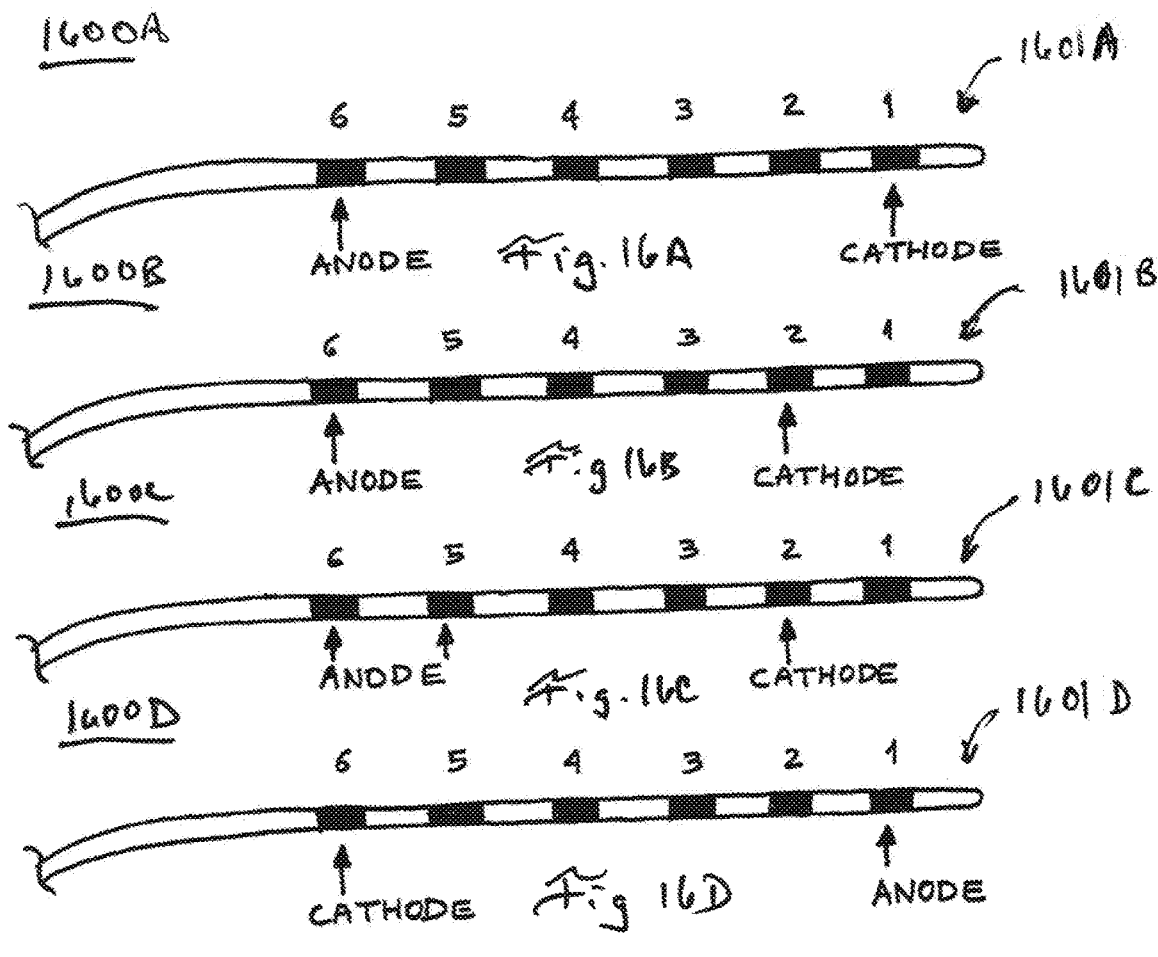
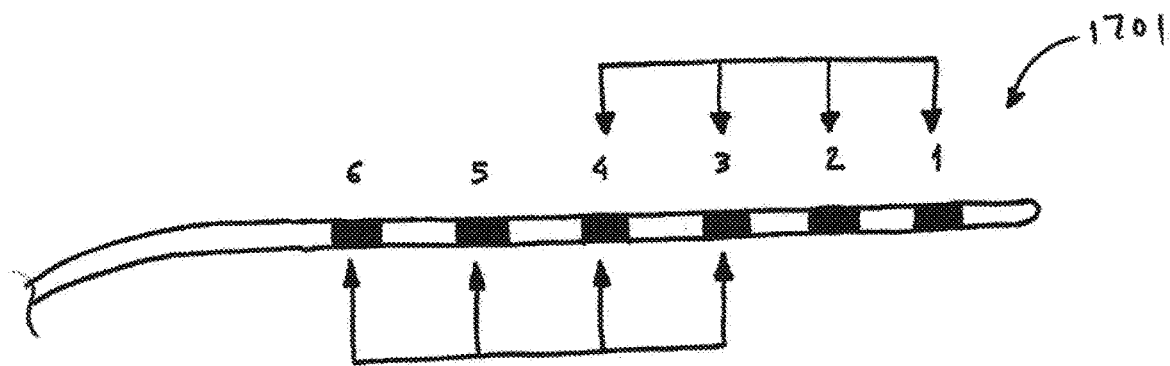
Fig. 17

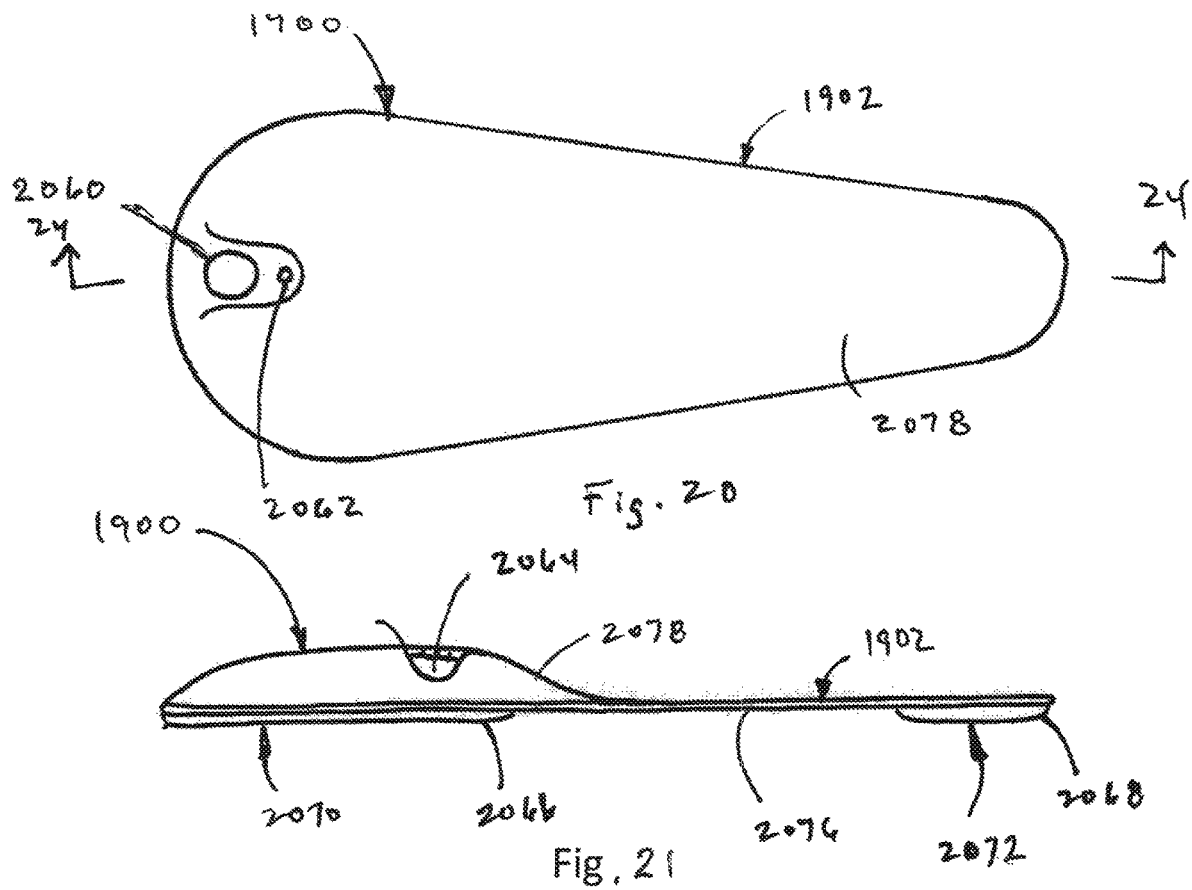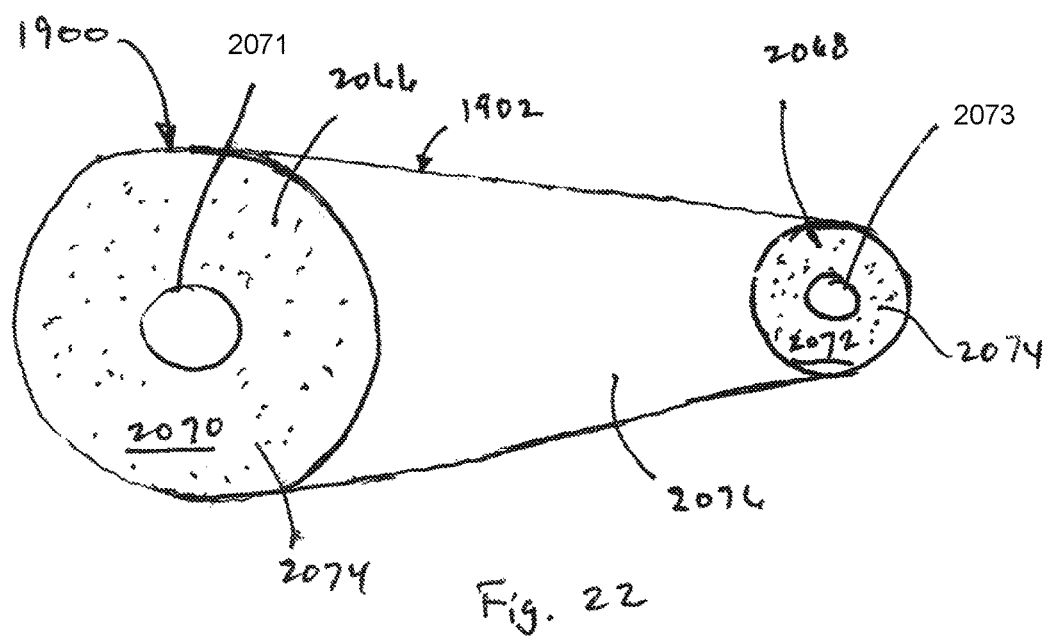

STIMULATION SYSTEM FOR EXERCISING DIAPHRAGM AND METHOD OF OPERATION THEREOF

CROSS-REFERENCE TO RELATED APPLICATIONS

This application is a continuation in part of U.S. patent application Ser. No. 14/941,422, entitled, ICU TEMPORARY PACER PROJECT, filed on Nov. 13, 2015 which is a continuation of U.S. patent application Ser. No. 14/673,470, entitled, ICU TEMPORARY PACER PROJECT, filed on Mar. 30, 2015, which is a non-provisional and claims the benefit of U.S. Provisional Patent Application No. 61/972,093, entitled, "ICU TEMPORARY PACER PROJECT," filed on Mar. 28, 2014. The contents of all of the above-noted applications are incorporated herein by reference as if set forth in full and priority to these applications is claimed to the full extent allowable under U.S. law and regulations.

FIELD OF THE PRESENT SYSTEM

The present system relates to a medical stimulation system to stimulate a phrenic nerve to exercise a diaphragm of a patient and, more particularly, to a medical stimulation system to stimulate a phrenic nerve to exercise a diaphragm of a patient to reduce the time necessary to wean the patient from a mechanical ventilator (MV), and methods of operation thereof.

BACKGROUND OF THE PRESENT SYSTEM

Each year tens of thousands of patients require mechanical ventilation (MV) in a hospital intensive care unit (ICU) setting for a variety of reasons. Costs for a patient in the IOU are approximately 4 times greater than the costs for a patient not in the ICU. Much of the added costs are related to mechanical ventilation. There are 2.7 mechanical ventilator patients per 1,000 of population. MV is an inpatient procedure that may consume more health dollars annually when compared with other inpatient procedures. Unfortunately, the number of critically ill patients requiring MV is increasing by about 5.5% each year.

Unfortunately, patients who have been mechanically ventilated may be difficult to wean off of the MV because their diaphragm may become weakened from lack of use. The longer a patient requires MV the more susceptible the patient is to the complications of MV and the longer the patient must remain in the ICU. There are also substantial expenses to providing MV to a patient. It is therefore desirable to shorten the time required for ventilation support.

Once a patient is found to no longer require this artificial breathing assistance, the patient must be weaned from the ventilator before the patient may sustain him/herself with normal breathing. Difficulties in discontinuing MV support are encountered in a significant portion (reputed to be as high as 20%-25%) of the mechanically ventilated patients and 40% of time spent in the intensive care unit can be devoted to weaning from MV.

Ventilator-Induced Diaphragm Disuse (VIDD) appears to be a major cause of MV weaning problems. It has been found that the diaphragm rapidly atrophies, losing its ability to perform when its function has been taken over by MV. The effects of 18 to 69 hours of MV and complete diaphragmatic inactivity result in marked atrophy of human diaphragm myofibers. These findings are consistent with increased diaphragmatic proteolysis during inactivity. The diaphragm may atrophy at a rate of 6% per day of MV.

As compared with diaphragm-biopsy specimens from controls, specimens from case subjects showed decreased cross-sectional areas of slow-twitch and fast-twitch fibers of 57% (P=0.001) and 53% (P=0.01), respectively, decreased glutathione concentration of 23% (P=0.01), increased active caspase-3 expression of 100% (P=0.05), a 200% higher ratio of atrogin-1 messenger RNA (mRNA) transcripts to MBD4 (a housekeeping gene) (P=0.002), and a 590% higher ratio of MuRF-1 mRNA transcripts to MBD4 (P=0.001).

Accordingly, embodiments of the present system may overcome these and other disadvantages of mechanically ventilating a patient.

SUMMARY OF THE PRESENT SYSTEM

The system(s), device(s), method(s), arrangements(s), user interface(s), computer program(s), processes, etc. (hereinafter each of which will be referred to as system, unless the context indicates otherwise), described herein address problems in prior art systems.

In accordance with the embodiments of the present system, a method, apparatus, and system (collectively "system") are provided for reducing Ventilator-induced diaphragm dysfunction (VIDD) in a patient receiving ventilation support from an MV. The system involves monitoring the forced breathing cycle of the patient and stimulating the diaphragm of the patient, such that it does respiratory work while the patient is otherwise mechanically ventilated.

In this regard, stimulation may be implemented in any suitable way including percutaneous or transcutaneous stimulation of the phrenic nerve, direct or indirect stimulation of the phrenic nerve via electrode or other methods (e.g., via concentrated ultrasound or magnetic stimulation) or using other methods which may stimulate the diaphragm to do respiratory work. Signals employed by embodiments of the present system may be transmitted via wired and/or wireless methods.

For example, it is envisioned that the diaphragm can be stimulated to do respiratory work by concurrent stimulation with the ventilator (e.g., the ventilator forces a breath with air at positive pressure and the stimulation causes the diaphragm to force (draw) a breath with negative pressure), in conjunction with the ventilator (e.g., one or more of low level, medium level and high level stimulation in conjunction with each or selected ventilator breaths), or any other suitable coordination.

In accordance with embodiments of the present system, there is disclosed an apparatus for reducing ventilation induced diaphragm disuse in a patient receiving ventilation support from a mechanical ventilator (MV), including: an electrode array of first and second types and comprising a plurality of electrodes configured to stimulate a phrenic nerve of the patient; and at least one controller configured to: identify a type of electrode array from at least two different types, and generate a stimulus signal for stimulating a phrenic nerve of the patient based upon the identity of the electrode type. It is envisioned that the at least one controller may be further configured to determine a jumper setting to identify the type of electrode array. The at least one controller may be further configured to control an amplitude of the stimulus signal in accordance with the identified type of electrode array.

It is also envisioned that the at least one controller may be further configured to obtain breathing cycle information indicative of a breathing cycle of the MV. Further, the at least one controller may be further configured to control a repetition of the stimulus signal in accordance with the breathing cycle information. The at least one controller may be further configured to identify an identifier (ID) of a sensor which transmits the breathing cycle information. A display may be operatively coupled to the at least one controller. The at least one controller may be further configured to: determine a battery type of the identified sensor as one of a rechargeable or non-rechargeable battery based on the identifier (ID), determine an operating state of the rechargeable or non-rechargeable battery, and provide an indication on the display of the battery type and the operating state.

In accordance with embodiments of the present system, there is disclosed a method for reducing ventilation induced diaphragm disuse in a patient receiving ventilation support from a mechanical ventilator (MV), the method comprising acts of: a processor identifying a type of electrode array coupled to a patient from at least two different possible electrode types, and generating a stimulus signal for stimulating a phrenic nerve of the patient based upon the identification of the electrode type. It is envisioned that the processor may further perform one or more acts of determining a jumper setting to identify the type of electrode array, controlling an amplitude of the stimulus signal in accordance with the identified type of electrode array, obtaining breathing cycle information indicative of a breathing cycle of the MV, and controlling a repetition of the stimulus signal in accordance with the breathing cycle information. Further, the processor may perform an act of identifying an identifier (ID) of a sensor which transmits the breathing cycle information. It is also envisioned that the processor may perform acts of: determining a battery type of the identified sensor as one of a rechargeable or non-rechargeable battery based on the identifier (ID), determining an operating state of the rechargeable or non-rechargeable battery, and providing an indication of the battery type and the operating state.

In accordance with embodiments of the present system, there is disclosed a non-transitory computer readable medium comprising computer instructions which, when executed by a processor, configure the processor to perform a method for reducing ventilation induced diaphragm disuse in a patient receiving ventilation support from a mechanical ventilator (MV), the method comprising acts of: identifying a type of electrode array coupled to a patient from at least two different possible electrode types, and generating a stimulus signal for stimulating a phrenic nerve of the patient based upon the identification of the electrode type. It is envisioned that the method may include one or more acts of determining a jumper setting to identify the type of electrode array, controlling an amplitude of the stimulus signal in accordance with the identified type of electrode array, obtaining breathing cycle information indicative of a breathing cycle of the MV, and controlling a repetition of the stimulus signal in accordance with the breathing cycle information.

It is also envisioned that the method may include acts of: identifying an identifier (ID) of a sensor which transmits the breathing cycle information, determining a battery type of the identified sensor as one of a rechargeable or non-rechargeable battery based on the identifier (ID), determining an operating state of the rechargeable or non-rechargeable battery, and providing an indication of the battery type and the operating state.

BRIEF DESCRIPTION OF THE DRAWINGS

The present invention is explained in further detail in the following exemplary embodiments and with reference to the figures, where identical or similar elements are partly indicated by the same or similar reference numerals, and the features of various exemplary embodiments being combinable. In the drawings:

FIG. 5 shows a bottom planar view of a portion of a transcutaneous multi-electrode array (e.g., a transcutaneous array) in accordance with embodiments of the present system;

FIG. 6 shows a cross-sectional view of a portion of the multi-electrode array of FIG. 5 taken along lines 6-6 of FIG. 5 in accordance with embodiments of the present system;

FIG. 7 shows a top planar view of a portion of a transcutaneous multi-electrode array in accordance with embodiments of the present system;

FIG. 8 shows a side planar view of a portion of a percutaneous multi-electrode array (e.g., a percutaneous array) hereinafter in accordance with embodiments of the present system;

FIG. 9 shows a cross-sectional view of a portion of the percutaneous multi-electrode array of FIG. 8 taken along lines 9-9 of FIG. 8 in accordance with embodiments of the present system;

FIG. 10 shows a front perspective view of a portion of an electrode element of the multi-electrode percutaneous array coupled to a lead in accordance with embodiments of the present system;

FIG. 16A shows a block diagram of an anode and cathode selection in a multi-electrode array in accordance with embodiments of the present system;

FIG. 16B shows a block diagram of an anode and cathode selection in a multi-electrode array in accordance with embodiments of the present system;

FIG. 16C shows a block diagram of an anode and cathode selections in a multi-electrode array in accordance with embodiments of the present system;

FIG. 16D shows a block diagram of an anode and cathode selections in a multi-electrode array in accordance with embodiments of the present system;

FIG. 17 shows a block diagram of an anode and cathode selection in a multi-electrode array in accordance with embodiments of the present system;

FIG. 20 shows a top planar view of a portion of the sensor patch 1900 of FIG. 19 in accordance with embodiments of the present system;

FIG. 21 shows a front side view of a portion of the sensor patch of FIG. 20 in accordance with embodiments of the present system;

FIG. 22 shows a bottom planar view of a portion of the sensor patch of FIG. 19 in accordance with embodiments of the present system;

DETAILED DESCRIPTION OF THE PRESENT SYSTEM

Figure 1A:
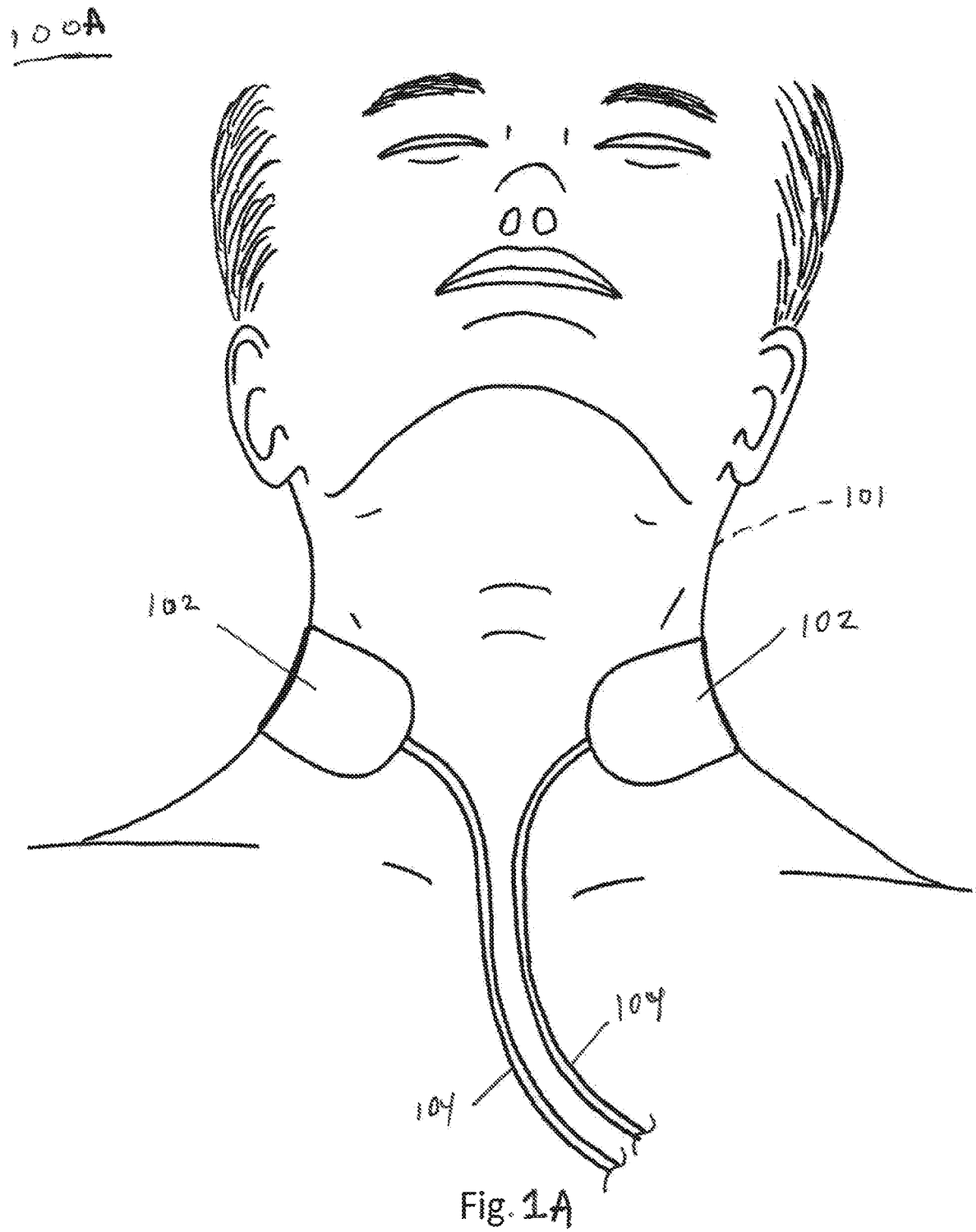
FIG. 1A shows a front view of a portion of transcutaneous or surface electrode arrays attached on each side of a neck of a patient in accordance with embodiments of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well-known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

Embodiments of the present system may employ a phrenic nerve stimulator (PNS) to temporarily trigger the diaphragm of a user (hereinafter patient for the sake of clarity) to exercise itself while the patient is on the support of a mechanical ventilator (MV) which may assist in weaning the patient from the MV. This may be accomplished by stimulation of the diaphragm, e.g., via direct stimulation of the phrenic nerve, in desired coordination with the ventilator forced-breathing cycle. Any appropriate source of stimulation signals may be used in accordance with embodiments of the present system and it is anticipated that such a source may be optimized for this application in practice. References are made below to particular systems involving stimulation of the phrenic nerve which may be performed through the skin either with an electrode positioned near the nerve (percutaneous) or positioned on the skin (transcutaneous). It should be expressly understood, however, that embodiments of the present system are not limited to any specific system.

Using a Stimulator for Mechanical Ventilator Weaning

The diaphragm is a large muscle that separates the thoracic and the abdominal cavities and rhythmically contracts and relaxes during normal operation, altering the volume of the thoracic cavity and the lungs, producing inspiration and expiration.

The diaphragm provides approximately 45% of the energy for the lungs to inflate, with the intercostal and accessory muscles accounting for the rest. When the diaphragm contracts, moving down, and the intercostal and accessory muscles expand the thoracic cavity, a negative pressure is created inside the lungs and an inhalation mixture such as ambient air with for example 20% of oxygen content is drawn in. This process may be known as an inspiratory phase or inspiratory period of a breath. When the muscles relax, the air with a much higher concentration of carbon dioxide than it contained when it was inhaled into the lungs is exhaled from the lungs and this process may be referred to as an expiratory phase or expiratory period of a breath. This rhythmic cycle forms the breathing cycle.

A mechanical ventilator (MV) may provide an artificial method for a patient to breathe when the patient's lungs cannot breathe on their own. This may be due to brain or brain stem lesions, stroke, trauma, tumors, lung disorders, acute respiratory failure, heart issues, direct injury to the lungs due to accidents, during surgery, when the patient is sedated, or has taken depressant drugs, etc. MVs are universally used in hospitals all over the world. MVs provide the oxygen demands by pumping an inhalation mixture of air into the lungs to create an artificial inspiratory phase of a breath. With the interruption of pumping pressure from the MV, the air with carbon dioxide is expelled out of the lungs due to the elastic recoil of the diaphragm and the chest wall, creating an expiratory phase of a breath. Repeated cycles of the inspiratory and expiratory phases generate the normal breathing pattern to maintain the patient alive and with the proper respiratory requirements.

MVs are normally used for short periods of time (a few days) but in cases it may be used for weeks, months, or even years. When a patient is able return to spontaneous breathing (e.g., to breathe on his/her own) and to be disconnected from the ventilator, a weaning-off period (e.g., a weaning) is, in most cases, necessary. Approximately 10-15% of patients require 24 to 72 hours of weaning, 5-10% of the patients require a gradual weaning over an extended period of time, and 1% of patients become chronically dependent on the MV, for example due to the diaphragm having lost its strength.

Considering that the weaning period may be substantial compared to the time the patient needs the mechanical ventilator, costs can be quite high. Accordingly, embodiments of the present system may greatly reduce these costs by shortening the weaning period or even eliminating it. This can be accomplished by using a stimulator operating in accordance with embodiments of the present system such as phrenic neurostimulator (PNS) (also referred to herein as a breathing pacemaker, a phrenic pacemaker, a diaphragmatic pacemaker, a Temporary Diaphragmatic Stimulator (TDS), etc.), which is a neurostimulator that may stimulate the phrenic nerve so the diaphragm of a patient can contract on its own for example using electrical stimuli such as an electrical current that may be transmitted to the phrenic nerves of the patient to induce this contraction. In accordance with embodiments of the present system, this stimulation may be used to prevent atrophy and/or to provide breathing support as may be discussed below.

It is appreciated that the electrical current necessary to produce a discernible movement of the diaphragm has been found to remain unchanged over an average time span of 61 months. Tidal volumes equaled or exceeded basal requirements as calculated by the Radford nomogram, arterial blood gases were normal and diaphragm acceleration remains low indicating preservation of slow-twitch muscle fibers.

PNSs may be chronically implanted in patients with Congenital Central Hypoventilation Syndrome or CCHS (or Ondine's curse), spinal cord injury, diaphragmatic paralysis or other diagnoses in which the patient cannot breathe on his/her own. Patients may need the breathing or diaphragmatic pacemaker (hereinafter both of which may be referred to as pacemaker for the sake of clarity) during the night (CCHS patients) or continuously (spinal cord injury patients and some CCHS patients). Such neurostimulators, or any other neurostimulator, may be used in accordance with embodiments of the present system and such neurostimulators may be referred to herein as a Temporary Diaphragmatic Stimulator (TDS).

As used herein, and for the sake of clarity, it will be assumed that a PNS when used with an MV which substantially provides breathing support to a patient may be referred to as a TDS. In this case, the TDS may be operative to stimulate the phrenic nerves of the patient so as to prevent atrophy together with the breathing support which is provided by the MV.

A PNS when not used with an MV may be operative to substantially supply breathing support to a patient independently of the MV. More particularly, the PNS may operate independently of the MV, to stimulate phrenic nerves to drive the diaphragm for every breath and in the inspiratory phase of all breaths so as to provide breathing support to a patient. In contrast, a TDS may be employed with an MV and may stimulate the phrenic nerves either in the inspiratory phase or in the expiratory phase (depending on the selected mode of operation as will be described below), and may stimulate the phrenic nerves to prevent disuse of the diaphragm while the patient is supported by the MV and cannot breathe on his/her own. Thus, while an MV may provide substantially all the ventilatory support, the TDS may stimulate phrenic nerves to condition the diaphragm so as to prevent atrophy of the diaphragm as opposed to using only the MV to breathe.

Figure 34A:
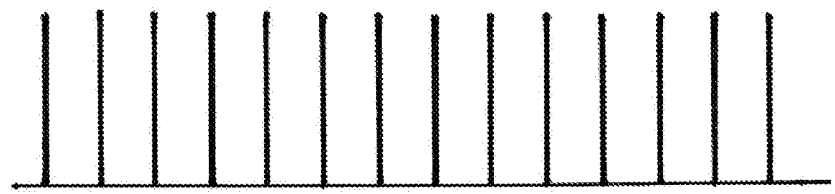
FIG. 34A shows a portion of a stimulus a pulse train that may be provided to a TDS in accordance with embodiments of the present system.
Figure 34B:
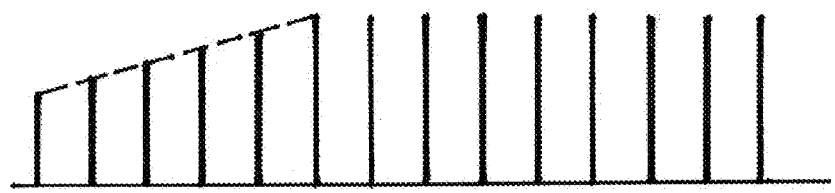
FIG. 34B shows a portion of a stimulus a pulse train that may be provided to a TDS in accordance with embodiments of the present system.
Figure 34C:
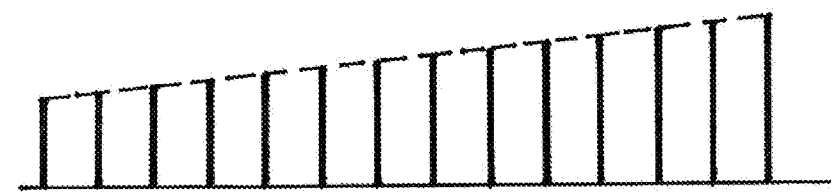
FIG. 34C shows a portion of a stimulus a pulse train that may be provided to a TDS in accordance with embodiments of the present system.
Figure 34D:
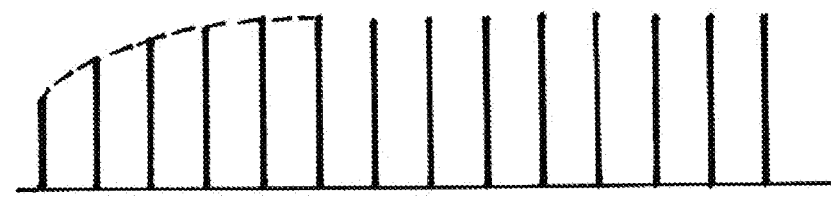
FIG. 34D shows a portion of a stimulus a pulse train that may be provided to a TDS in accordance with embodiments of the present system.
Figure 34E:
FIG. 34E shows a portion of a stimulus a pulse train that may be provided to a TDS in accordance with embodiments of the present system.

A TDS operating in accordance with embodiments of the present system may generate electrical stimulus pulses that are sent to the diaphragm via the phrenic nerves of the patient as a pulse train. The pulse train may contain a certain number of pulses all with the same amplitude. FIG. 34A shows a pulse train having all pulses with a constant amplitude. Optionally, the amplitude of the pulse train may gradually increase from a minimum value to a maximum value. This rate of change from one pulse to the next, called slope, may be linear in which the amplitude difference or increment from one pulse to the next is the same for all other pulses, or may be non-linear, in which the amplitude difference or increment from one pulse to the next may gradually vary from pulse to pulse. Non-linear slopes may have different shapes, e.g., hyperbolic, or others. The slope may affect all pulses of the pulse train or may affect only a portion of the pulse train. For example, the slope may be present in a portion of the pulses and not be present in the remaining portion of the train. FIG. 34B shows a pulse train with a linear slope affecting only the first portion of the pulses and with no slope in the remaining pulses. FIG. 34C shows a pulse train with a linear slope affecting all the pulses of the train. FIG. 34D shows a pulse train with a non-linear slope, in this case a hyperbolic curve affecting a portion of the pulses of the pulse train. FIG. 34E shows a pulse train with a non-linear slope, in this case illustratively a hyperbolic curve, affecting all the pulses of the pulse train. In accordance with embodiments of the present system, the pulse train is utilized to stimulate the phrenic nerve while the patient is otherwise ventilated by a MV. For example, during the inspiratory phase, electrical stimuli in a form of a pulse train provided to the phrenic nerve as described herein may be utilized to contract the diaphragm. During the expiratory phase, absence of stimuli may allow the diaphragm to relax.

In accordance with embodiments of the present system, the TDS may be used to wean patients from ventilatory support provided by an MV. The TDS does not have to be chronically implanted but may be used acutely (i.e., temporarily), while the patient requires ventilatory support. Accordingly, temporary implantable electrodes may be inserted in a lower neck area at or in proximity to the phrenic nerve so that the diaphragm may be stimulated. The implantable electrodes may be placed through a catheter which may be guided using any suitable guidance system such as an ultrasound, fluoroscopy or MRI guidance systems. In accordance with yet other embodiments, it is envisioned that surface electrodes may be placed on the skin of the patient rather than, or in addition to, the implantable electrodes. After the patient is removed from the MV and the weaning period is over, the electrodes may be removed without any damage to the phrenic nerve.

When the MV pumps air into the lungs of the patient, positive pressure inside the lungs may force the diaphragm to move downwards and may cause the thoracic and abdominal cavities of the patient to expand. This involuntary movement is caused only by the air pressure of the MV, and not by muscle contraction. This lack of work by the diaphragm, causes the diaphragm muscle fibers to atrophy. Studies show that diaphragm begins atrophying at about 6 to 18 hours after MV begins.

A TDS in accordance with embodiments of the present system may supply temporary stimulation of the diaphragm to prevent atrophy of the diaphragm while the patient requires ventilator support from an MV. Studies also show that 40% of the time the patient is on the MV is for weaning. If the diaphragm can also be stimulated by electrical stimuli, the conditioning phase could begin while still on the MV thus preventing or reducing the time required for weaning. This conditioning or weaning period can be greatly reduced compared to physician-directed weaning, or even eliminated if the diaphragm does not atrophy. When the patient is ready to be removed from the MV, the patient's respiratory system may be able to start on its own for its ventilation needs and keep proper gas exchange within the lungs.

This reduces the treatment period while the patient is in the ICU, reduces the risks normally associated with the MV (infections, etc.), better utilizes the beds by freeing them sooner to other patients, the patient is discharged sooner, and greatly reduces costs to the patient, to the hospital, and to the insurance company. However, for proper diaphragm conditioning, the MV and the TDS may be synchronized and operate at the same time. Accordingly, the TDS may be configured to detect a respiratory pattern and may be operative to stimulate the diaphragm of a patient on ventilator support.

In accordance with embodiments of the present system, there are several methods in which a TDS may be operative with an MV to control some degree of contraction of the diaphragm while the patient is otherwise provided with a ventilator-induced breath. One method is to stimulate the diaphragm with a minimum contraction such that it doesn't disturb the operation or the settings of the MV. Another method is to work at the same time with the MV, alternately generating shallow breaths or full breaths to the patient. Another method is to stimulate at the same time with the MV to provide support to the MV breath. A variety of possible modes of operation is described herein below.

Unfortunately, ventilator manufacturers don't provide a common interface on MVs to allow for control of a remote device. Further, even when an interface to an external device is provided, it may employ a proprietary protocol which may be unknown to all but the manufacturer of the corresponding MVs so as to make it difficult, or impossible, to interact with these MVs via the interface. Accordingly, in order to interface with MV, the TDS would have to recognize the protocols of all the different MV models to properly interface with any of them. This would make the hardware and the software of the device and operation more complicated (e.g., including steps such as "select MV, model number," etc.). In addition, a custom interface cable for each ventilator would be required, which would make the system more expensive and complicated to operate. All the cables would have to be available when a patient is connected to a MV. If the patient is switched to another MV, another cable would have to be used, complicating the process.

Accordingly, embodiments of the present system may employ a much simpler approach to interface with an MV. For example, it is envisioned that embodiments of the present system may determine when an MV begins a cycle such as a breath cycle to properly synchronize it with a pacemaker operating in accordance with embodiments of the present system.

In accordance with embodiments of the present system, two stimulating electrodes or two stimulating patches for example as described in FIGS. 1A, 1B, 1C and 1D may be used to stimulate the phrenic nerves of a patient. Further, two sensing patches as for example described in FIGS. 19 and 20 may be used to detect the ventilatory pattern generated by the MV. The sensing patches may be placed on a chest of a patient as described below with reference to FIG. 19 and may provide a feedback signal to a controller of the system. The controller may control the overall operation of the system and may drive the two stimulating electrodes and/or two stimulating patches. For this application, two types of stimulation are now described: Transcutaneous Stimulation and Percutaneous Stimulation.

Transcutaneous Stimulation

In accordance with embodiments of the present system, transcutaneous stimulation or surface stimulation may be accomplished by using a surface electrode array for example embedded in an adhesive patch placed on each side of the neck (patient) near the area where the phrenic nerve is located. FIG. 1A shows a front view 100A of a portion of surface electrode arrays 102 attached on each side of a neck of a patient 101. The two surface electrode arrays 102 may include electrodes (e.g., an electrode element) for example having a semispherical shape (other shapes are also envisioned) such as a bump on a surface that contacts the skin to create at least one small dimple at a contact surface of the skin for better electrical contact. The surface electrode arrays 102 may be attached to the skin of the patient 101 using any suitable method such as adhesives, gels, etc. such that the electrodes are electrically and mechanically coupled to the skin of the patient 101. Each surface electrode array 102 may include an electrode cable 104 or may operate using wireless methods such as wireless RF methods. The shape and size of the surface electrode arrays 102 may be varied. For example, FIG. 1A shows a front view 100A of the surface electrode arrays 102 having an elongated shape attached on each side of the neck of the patient 101 in accordance with embodiments of the present system.

Percutaneous Stimulation

Percutaneous stimulation may be accomplished by using an electrode array with a tubular shape, inserted through the skin, on each side of the neck, where the phrenic nerve is located.

Figure 1B:
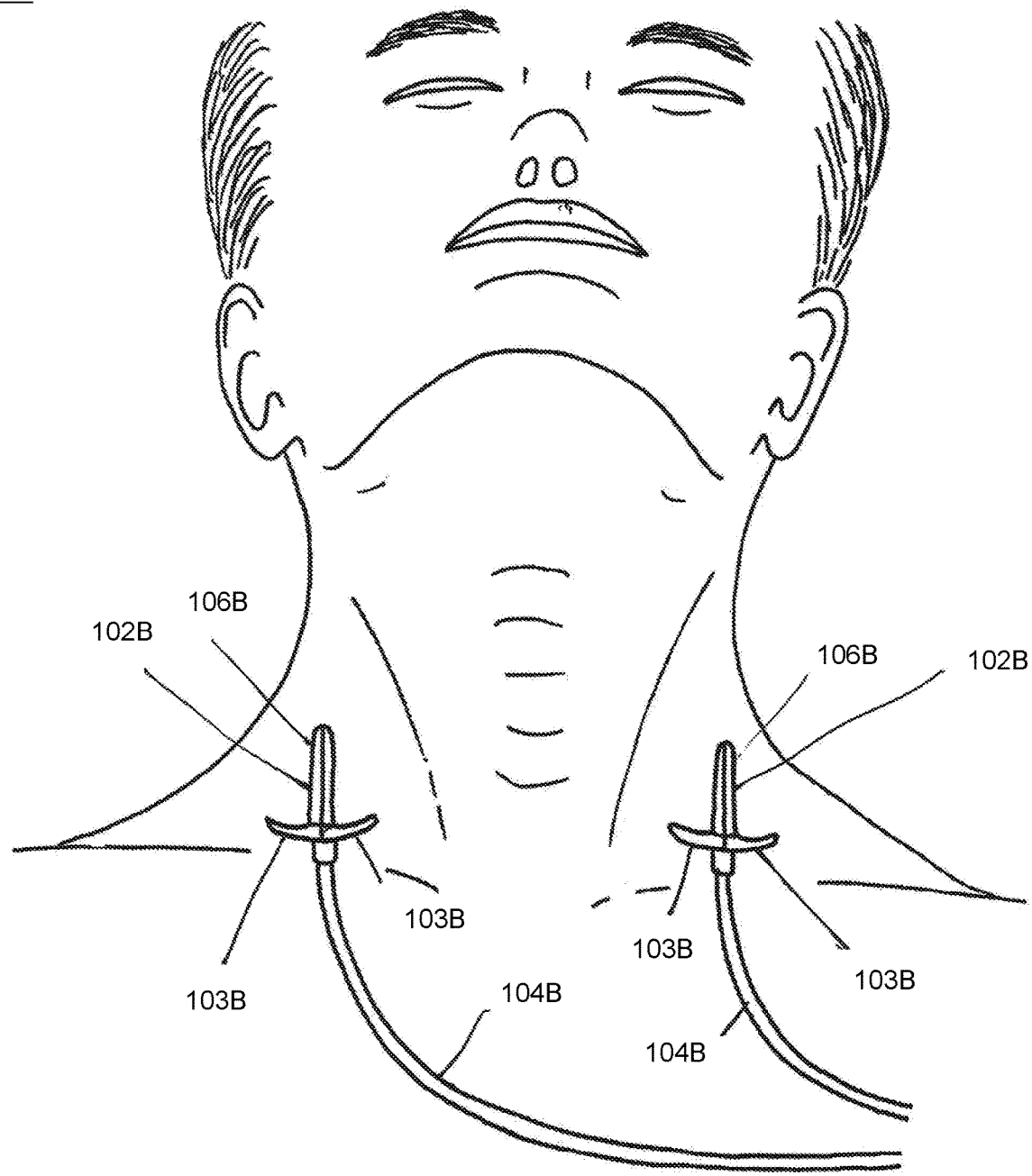
FIG. 1B shows a front view of the percutaneous electrode arrays having an elongated shape attached on each side of the neck of the patient in accordance with embodiments of the present system.
Figure 1C:
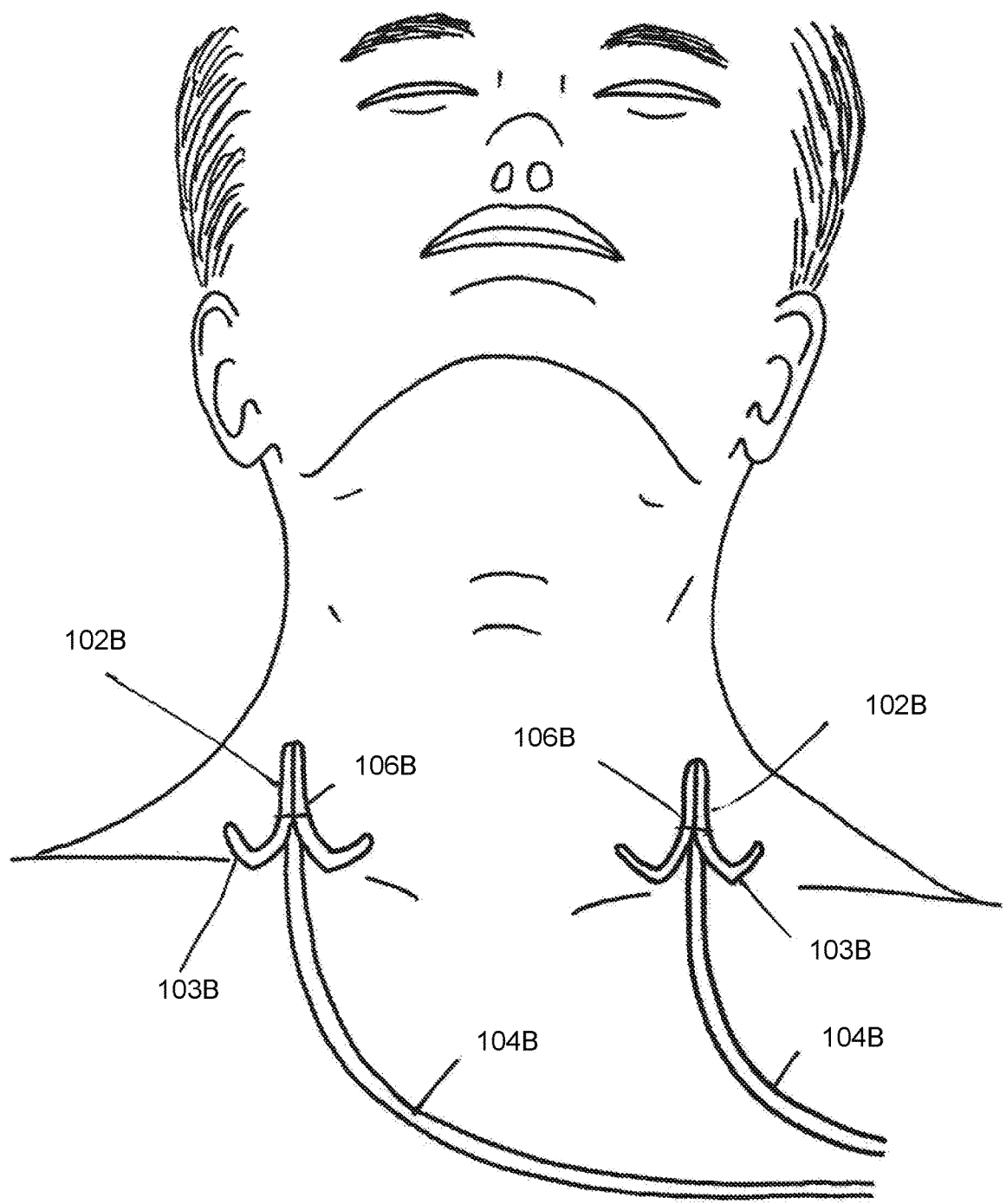
FIG. 1C shows a front view of a portion of percutaneous electrode arrays attached on each side of a neck of the patient in accordance with embodiments of the present system.

FIG. 1B shows a front view 100B of a portion of percutaneous electrode arrays 102B coupled to an electrode cable 104B which may couple a corresponding percutaneous electrode array to a stimulator to generate a drive signal to drive the electrode array. In accordance with embodiments of the present system, the electrode array 102B may be coupled to the stimulator via wired or wireless methods. As shown, the electrode array 102B may be inserted on each side of a neck of the patient 101 in accordance with embodiments of the present system. The two percutaneous electrode arrays 102B may have a tubular shape and may for example be inserted into position on a patient via for example an introducer 106B although other systems, such as a catheter, etc. may also be suitably utilized for insertion of the electrode arrays 102B. Introducers may be used to introduce and tunnel catheters or electrodes into the body. Some like the one illustratively shown may be flexible and may be peeled away when removed. The introducer 106B may include positioning members such as handles or tabs 103B of the introducer to help position the introducers 106B to assist in insertion and positioning the percutaneous electrode arrays 102B and to separate the two halves when the introducer 106B is removed. After the electrode array 102B is positioned properly, the peel-away introducer is pulled out from the body and peeled away, i.e., separated in half through a seam or groove along its body. FIG. 1C shows a front view 100C of a portion of the percutaneous electrode arrays 102B as the introducer 106B is peeled away in accordance with embodiments of the present system.

Figure 1D:
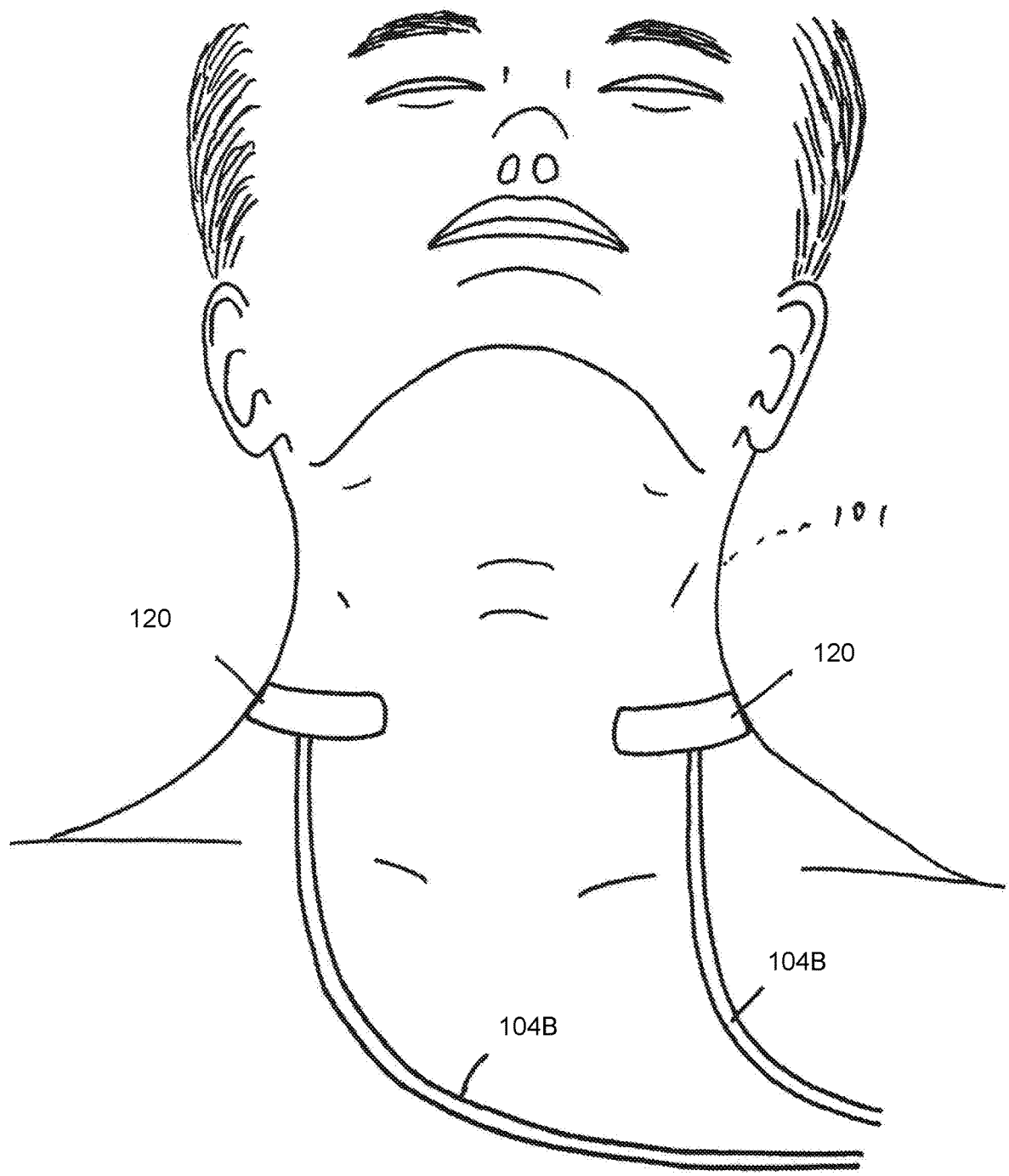
FIG. 1D shows a front view of a portion of the percutaneous electrode arrays attached on each side of a neck of the patient in accordance with embodiments of the present system.

FIG. 1D shows a front view 100D after the percutaneous electrode arrays 1026 are inserted on each side of a neck of the patient 101 and the introducer is removed. As shown, a covering such as adhesive tape 120 is positioned to hold the electrode arrays 1026 in place in accordance with embodiments of the present system.

Application of Transcutaneous Electrodes

For transcutaneous stimulation, the skin in the neck area may be cleaned and a stimulation patch including at least one electrode such as may be included in an electrode array may be placed in the neck area where the phrenic nerve lies. This technique may further be used to evaluate the conduction of the phrenic nerve by using a needle or a thimble electrode or a bipolar electrode probe on the neck, normally used in electromyography (EMG) tests, Phrenic Nerve Conduction Tests (PNCT) or others. Since there are two phrenic nerves, two patches should be placed with at least one on each side of the neck. This should be done preferably at the bedside as soon as possible after MV begins or even before to prep the patient for MV. The stimulation patches may be disposable. After the treatment is finished or during treatment, the stimulation patches may be removed and disposed of and replaced with new stimulation patches as may be required.

Application of Percutaneous Electrodes

For percutaneous stimulation, at least one electrode for stimulating the phrenic nerve may be inserted through the skin on each side of the neck. The electrode insertion may be performed at the bedside in the ICU as soon as possible after MV begins or even before to prep the patient for MV. The patient may have a local anesthetic applied to the skin in the lower neck region. Under sterile conditions, the electrodes for stimulating the phrenic nerve may be placed at, or adjacent to, the phrenic nerve, one on each side of the neck. To accomplish this, a small incision in the skin may be opened, each electrode (e.g., including a plurality of electrodes to form an electrode array) may be inserted for example in a peel-away introducer by tunneling through the small incision to a desired location (e.g., see FIGS. 1B-1D). In this regard, electrode placement may be performed under ultrasound guidance, e.g., ultrasound imaging to find the phrenic nerve and/or the anterior scalene muscle which the phrenic nerve transverses. Ultrasound guidance may also be used to monitor diaphragm excursion. After each electrode is fully inserted, the introducer may be drawn out, leaving the electrodes in place. After the introducer is fully removed from the subcutaneous tunnel, the introducer may be peeled away so that it can be removed completely from the electrode cable. Electrode leads such as an electrode cable may be secured to the skin on the neck using any suitable method such as a suture, adhesives, etc. (e.g., see, FIG. 1D), and an antibacterial ointment may be applied to prevent infection as may be desired.

The advantages of the transcutaneous stimulation technique include: a) noninvasive, b) no risk of infection or injury to blood vessels or nerves, and c) simplicity of application. The disadvantages include: a) inadvertent stimulation of adjacent nerves, b) significantly higher stimulation threshold, and c) easier for the patch array to be dislodged.

The advantages of the percutaneous technique include: a) more focused application of the stimulation, b) significantly lower stimulation threshold, c) lower probability of incidental stimulation of adjacent nerves, and d) lower chance of dislodging the electrode array. The disadvantages include: a) requires more expertise to place the device, and b) potential of introducing infection or injury to adjacent blood vessels or nerves.

To make placement of the transcutaneous or percutaneous arrays easier, instead of an electrode with two contacts, i.e., one cathode (also known as stimulating electrode) and one anode (also known as indifferent electrode), a multi-electrode array containing a plurality of electrode elements can be substituted for an electrode with two contacts.

Figure 2:
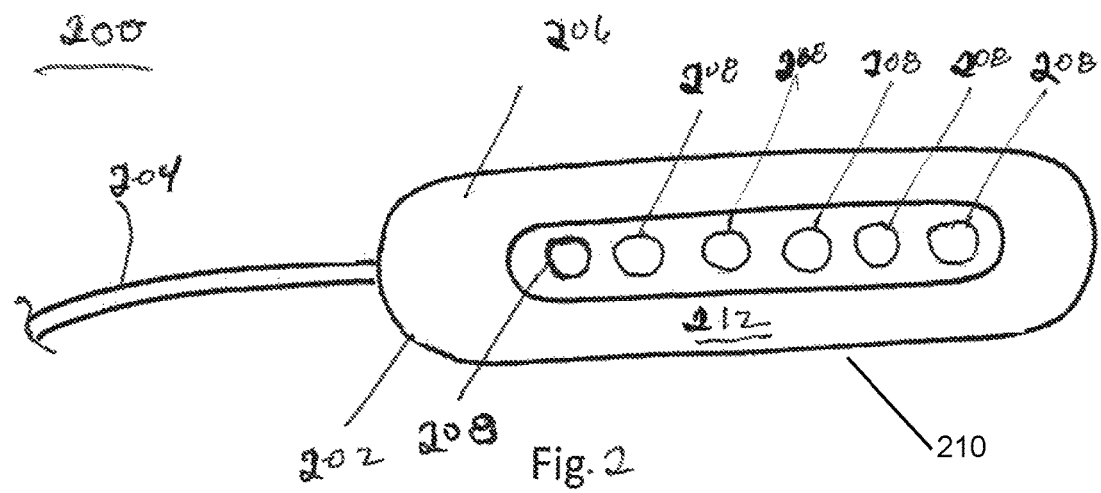
FIG. 2 shows a bottom planar view of a portion of a multi-electrode array which is suitable for transcutaneous use in accordance with embodiments of the present system.
Figure 3:
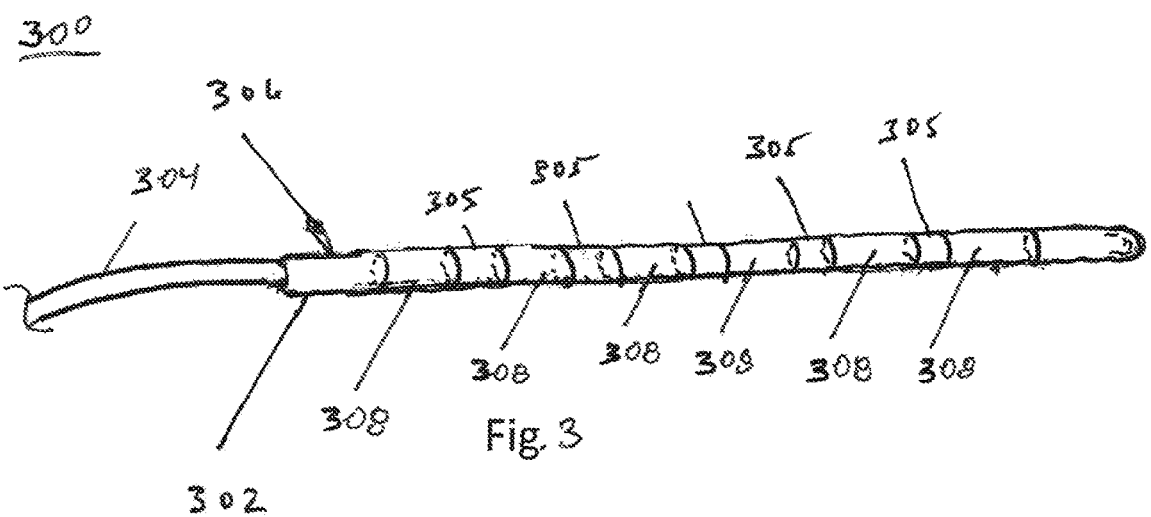
FIG. 3 shows a portion of multi-electrode array suitable for percutaneous use in accordance with embodiments of the present system.

A multi-electrode array including a plurality of electrodes is shown and described below for example with reference to FIGS. 2 and 3, wherein FIG. 2 shows a bottom planar view of a portion of a multi-electrode array 200 which is suitable for transcutaneous use in accordance with embodiments of the present system; and FIG. 3 shows a portion of multi-electrode array 300 suitable for percutaneous use in accordance with embodiments of the present system.

Referring to FIG. 2, the multi-electrode array 200 may include a surface electrode array 202 having a substrate 206 which may be flexible and a plurality of electrodes 208 (e.g., electrode elements). The electrodes 208 may be coupled to an electrode cable 204 which may include at least one lead (e.g., an anode lead and/or a cathode lead) and will be discussed in detail herein. The substrate 206 may be formed from any suitable material such as a flexible plastic or silicone and may have upper and lower major surfaces 210 (e.g., on a backside) and 212, respectively. The electrodes 208 may be situated adjacent to or on the lower major surface 212. The substrate 206 may be formed from a suitable material and should have a size and a shape to permit sufficient mechanical and electrical coupling to a patient using a desired coupling method such as adhesive, tape, gels, etc.)

By using a multi-electrode array 200, the position of the multi-electrode array 200 may not be critical as it is when using a single set of electrodes (e.g., an anode and a cathode pair which may be referred to as an electrode pair) as long as the multi-electrode array 200 is placed near, or at, the phrenic nerve. Each electrode 208 (e.g., an electrode element) may function as an anode or a cathode element. The exact position of the electrode 208 placement will be determined when applied stimulation results in appropriate diaphragm movement as determined by any suitable method such as: ultrasonic detection of diaphragm excursion, tidal volume measurement, spirometry, fluoroscopy, manual palpation, visual observation of the abdominal area or other methods. Optionally, the anode or indifferent electrode (or one or more of the selectable anodes) may be a conductive patch formed separate from the multi-electrode array 200 and positioned on the skin as used in many electrotherapies.

With reference to FIG. 3, the multi-electrode array 300 may include a percutaneous electrode array 302 having a body 306, electrode elements 308, and an electrode cable 304 including a plurality of leads coupled to corresponding electrode elements 308. The body 306 may be shaped as an elongated cylinder. The electrode elements 308 may form rings situated about the body 306 and fitting flush with an external periphery of the body 306. Each electrode element 308 may be coupled to corresponding lead of the plurality of leads. The body 306 may be formed from a non-conductive material (e.g., plastic, silastic, etc.) such that adjacent electrode elements 308 may be electrically isolated from each other by isolation areas 305.

Figure 4:
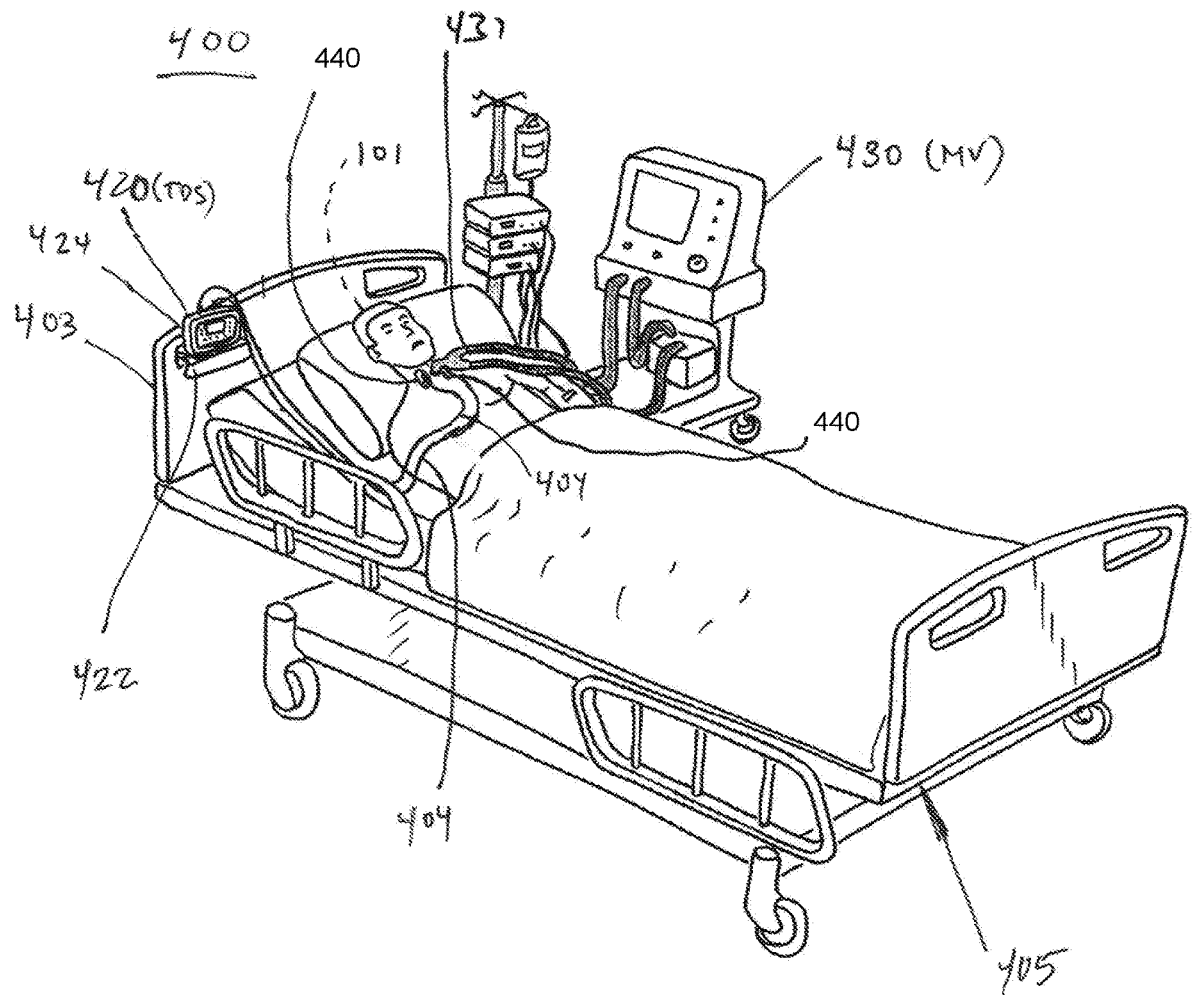
FIG. 4 shows a perspective view of a stimulator such as a TDS mounted to a bed rail of a patient support platform supporting a patient in accordance with embodiments of the present system.

FIG. 4 shows a perspective view 400 of a stimulator such as a TDS 420 mounted to a headboard 403 of a patient support platform, such as a bed 405, supporting a patient 101 in accordance with embodiments of the present system. Any suitable coupler, such as a mounting bracket 422, may couple the TDS 420 to the bed 405 such as via the headboard 403, a bed rail, etc. It is envisioned that the mounting bracket 422 may be provided with a quick disconnect feature which allows for a quick removal of the TDS, which may be useful when the patient has to be bathed, turned, or moved to another location such as to undergo a certain therapy. The TDS 420 may include a body 424 in which at least one controller (e.g., including a logic device such a microprocessor, a processor, one or more logic gates, circuits, etc.) for controlling the overall operation of the TDS 420 may be located. The TDS 420 may be coupled to the headboard 403 and may be easily decoupled and moved to facilitate patient 101 movement such as may be required when turning and/or bathing the patient 101 or when performing other treatments or diagnostic tests upon the patient 101. Optionally, the TDS 420 may be mounted on an equipment cart near the bed 405 of the patient 101. The TDS 420 may be coupled to multi-electrode arrays 440 (or other suitable electrodes) via one or more electrode cables 404 which may be of sufficient length to minimize the possibility of the multi-electrode arrays 440 from being dislodged. The multi-electrode arrays 440 may be similar to the multi-electrode arrays 200 or 300 and may include any number of electrode elements (e.g., electrodes 208 or 308).

The patient 101 may be coupled to an MV 430 via tubing 431 so as to receive a breathing gas mixture from the MV 430 sufficient to support ventilation of the patient 101. Connected to the patient, the MV may have a dual-limb ventilator tube comprising two tubes, one each for the inspiratory and the expiratory circuits connected to one tube with a Y connection or may have only a single tube for both circuits. The TDS 420 may be coupled to the MV 430 so as to determine an operative state of the MV 430 using any suitable method such as wired, wireless, pneumatic, etc., methods.

FIG. 5 shows a bottom planar view of a portion of a transcutaneous multi-electrode array 500 (e.g., a transcutaneous array) in accordance with embodiments of the present system; FIG. 6 shows a cross-sectional view of a portion of the transcutaneous multi-electrode array 500 of FIG. 5 taken along lines 6-6 of FIG. 5 in accordance with embodiments of the present system; and FIG. 7 shows a top planar view of a portion of the transcutaneous multi-electrode array 500 in accordance with embodiments of the present system.

With reference to FIGS. 5 and 6, the transcutaneous multi-electrode array 500 may include a substrate layer 506 which may support a plurality of electrode elements 508 and an adhesive layer 516. The adhesive layer 516 may provide adhesion to the patient. It is envisioned that the electrode elements 508 are affixed and/or embedded to the substrate layer 506. The electrode elements 508 may be situated in an array of a plurality of electrode elements 508 (e.g., five, six, seven, etc.) and may be aligned in an island 514 centered within an adhesive layer 516 deposited upon a lower major surface 512. However, it also envisioned that the adhesive layer 516 may be deposited upon a substantial portion of the lower major surface 512 so as to couple the electrode elements 508 to the lower major surface 512 of the substrate layer 506.

In accordance with embodiments of the present system, each of the electrode elements 508 may have any suitable shape such as flat circular shape or a semispherical shape (as shown) and with a radius ($R_E$) larger than a thickness ($T_E$) of the adhesive layer 516 to enhance contact with the skin (e.g., a dermal layer) of the patient by increasing pressure on the electrode elements 508 when they contact the skin of the patient thereby, enhancing electrical coupling of the electrode to the skin of the patient.

Each of the electrode elements 508 may include at least one protrusion. A corresponding dimple is formed on the skin at points of contact between the protrusion and the skin thereby enhancing electrical coupling with the skin of a patient such as shown in FIG. 6. In accordance with embodiments of the present system, the electrode material should be a material that is biocompatible to resist damage to the electrode and the patient. For example, the electrode elements 508 may be formed from platinum, platinum/Iridium alloy, iridium oxide or other materials with or without a coating (e.g., a double-layer coating such as titanium nitride, carbon nanotubes, etc.) that prevent electrode damage (i.e., dissolution) or tissue damage due to reaction products. Each electrode element 508 may include a corresponding lead 518 coupled thereto. These leads 518 may be referred to as drive leads (E (n)), where n is an integer from 1 through the maximum number of electrode elements 508 which is 6 in the illustrative embodiment shown. Thus, the leads 518 may be referred to as lead E1 through E6 in the present embodiments.

The leads 518 may be secured by a band 520 (e.g., a ring, a knot, a grommet, an adhesive, epoxy, etc.) so as to form a strain relief to prevent damage to individual leads 518 during placement and use. The secured leads 518 may then form at least one electrode cable 504 such that the electrode cable 504 which may exit beyond an external periphery of the substrate layer 506. The electrode cable 504 may then be coupled on an opposite side to an electrode array connector 533 (i.e., a multi-pin connector (MPC)) which may be configured to be coupled to a stimulator operating in accordance with embodiments of the present system.

A pin diagram of the electrode array connector which may be similar to the electrode array connector 533, is illustratively described with reference to FIG. 11.

Each electrode element 508 may be configured to contact the skin of the patient 101 and may be coupled to one of the corresponding leads 518 using any suitable method such as adhesives, welds, bonds, etc. Any suitable method may be used to fabricate all or a portion of the electrode array 500 such as three-dimensional (3D) printing, metal deposition, flexboard (i.e., flexible printed circuit board (PCB)), layering of flexible layers, injection molding, and/or combinations thereof. However, it is also envisioned that the electrode array 500 may be formed, at least in part, by layering sheets upon each other.

One or more of the leads 518, the electrode elements 508, the band 520, and the at least one electrode cable 504 may be secured to the substrate layer 506 and/or to each other by the adhesive layer 516.

FIG. 8 shows a side planar view of a portion of a percutaneous multi-electrode array 800 (e.g., a percutaneous array) hereinafter in accordance with embodiments of the present system; FIG. 9 shows a cross-sectional view of a portion of the multi-electrode array 800 of FIG. 8 taken along lines 9-9 of FIG. 8 in accordance with embodiments of the present system; and FIG. 10 shows a front perspective view of a portion of an electrode element 808 of the multi-electrode array 800 coupled to a lead 818 in accordance with embodiments of the present system. For example, an electrode element 808 may be welded to the lead 818 (e.g., welded at one or more places to ensure a good electrical connection.)

In the figures, the leads 818 may be identified by the electrode element 808 to which they are coupled to. Thus, assuming that there N=6 electrode elements in the present example, each electrode element 818 may have an identification E(n), where n equals 1 to N, then an $n^{th}$ electrode element 808(n) may be coupled to an $n^{th}$ lead 808(n). Thus, electrode element 808(1) may be coupled to lead E(1) (or E1), and electrode element 808(2) may be coupled to lead E(2), and an $N^{th}$ electrode element 808(N) may be coupled to lead E(N).

With reference to FIGS. 8 and 9, the percutaneous multi-electrode array 800 may include a body 806 having a cylindrical shape with first and second ends 807 and 809, respectively. The body 806 may have a length and diameter suitable for subcutaneous insertion within a body of a patient. At least one of the ends such as the first end 807 may be rounded or otherwise shaped so as to be easily navigated and positioned within a catheter which may be inserted percutaneously within the patient.

A plurality of electrode elements 808 may be extended about an outer periphery of the body 806 so as to form a conductive ring or annular shape and may for example be equally spaced apart from each other.

Each of the electrode elements 808 may be coupled to a corresponding lead 818 which may extend from an electrode cable 804. The electrode cable 804 may be coupled at on opposite end to an electrode array connector 833 which may be similar to electrode array connector 533 (i.e., an MPC). The body 806 may include depressions on an outer periphery to accept the electrode elements 808 or may have a smooth outer periphery.

With reference to FIG. 9, the electrode elements 808 may fit substantially flush with an outer periphery of the body 806 for easy insertion and removal to/from the patient. Each electrode element 808 may be coupled to a corresponding lead (wire) 818 using any suitable method such as welding, adhesives, bonds, pressure fits, etc. Any suitable method may be employed to fabricate the multi-electrode array 800, or portions thereof, such as 3D printing, metal deposition, flexible printed circuit board (or commonly known as flex board), and others.

With reference to FIG. 10, the leads 818 may be formed from any suitable conductive wire (e.g., copper, silver, stainless steel, solid or stranded, etc.) material and may be coupled to a corresponding electrode element 808 at or adjacent to an end of the corresponding lead 818. In accordance with embodiments of the present system, a stranded lead with many strands may be utilized to ensure redundancy in the connection to each of the electrode elements in case one or more of the strands fails during use.

Referring back to FIG. 8, a plurality (e.g., all) of the leads 818 may be secured at or adjacent to the second end 809 of the body 806 and/or to each other using any suitable coupling method and enter the at least one electrode cable 804. A coupler may be coupled to one or more of the leads 818 and/or the electrode cable 804 to form a strain relief. Further, the body 806 may include cutouts, notches, and/or vias through which one or more of the leads 818 and the electrode cable 804 may run.

In both transcutaneous and percutaneous array types (e.g., FIGS. 5 and 8), the electrode cable may branch into a plurality of leads which may end in a multi-pin connector (MPC) which may be configured to be connected with a controller of the system as illustratively described herein below. For the sake of clarity and as discussed herein, it is illustratively shown having an array that includes six (6) electrode elements. However, other numbers of electrode elements are also envisioned. Because of various differences between operational requirements of array types such as differences in drive signals (e.g., transcutaneous array types may require drive signals with greater current amplitude levels and/or wider pulses than that of percutaneous array types), it may be desirable to distinguish an array type employed by the present system using the MPC of the multi-electrode array.

Figure 11:
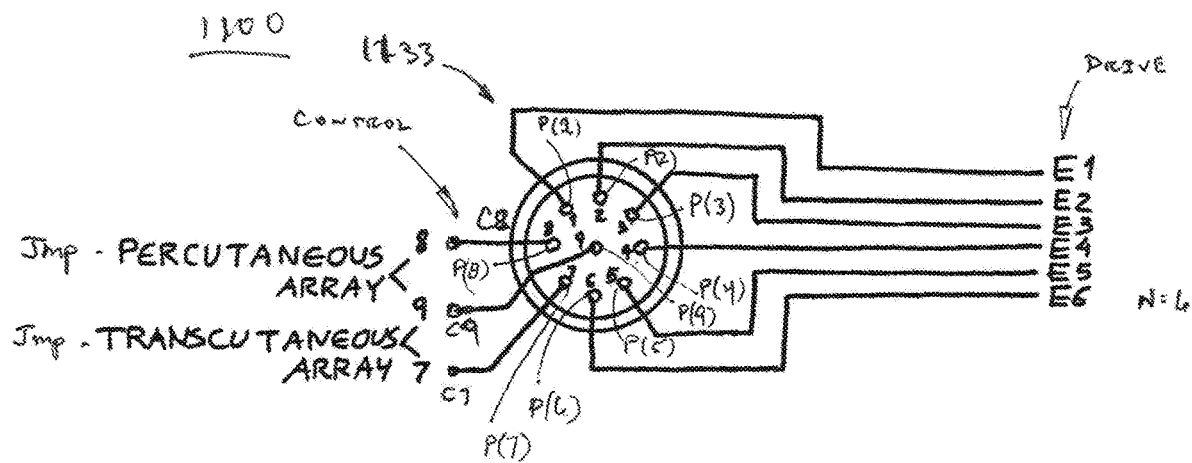
FIG. 11 shows a schematic diagram of a portion an electrode array connector including 9 pins in accordance with embodiments of the present system.

FIG. 11 shows a schematic diagram of a portion an electrode array connector 1133 which may be an MPC as discussed including 9 pins in accordance with embodiments of the present system. In accordance with embodiments of the present system, the electrode array connector may be configured to distinguish transcutaneous and percutaneous multi-electrode arrays with which it may be used using a jumper or other setting. The electrode array connector 1133 may include a plurality of pins P wherein each pin (P) may be identified by pin number (P(i), where i=1 through max number of pins such as P(1) through P(9) in the present illustrative embodiments. Pins P(1) through P(N), where N is equal to the maximum number of electrode elements such as 6 in the present embodiments may be designated as drive pins. Additionally, three additional pins (e.g. pins P(N+1), P(N+2), and P(N+3) (e.g., pins P(7), P(8), and P(9), respectively, which are respectively coupled to leads C(7), C(8), and C(9)) may be designated as control pins and may be used for encoding purposes such as for identifying an array type (e.g., transcutaneous and percutaneous array types in the present examples) being used with the multi-pin connector 1100. Accordingly, a single electrode array connector 1133 may be employed regardless of an array type being employed. Each of the drive pins P(n) through P(N) (e.g., P(1) through P(6) in the present embodiments) may be coupled to a corresponding $n^{th}$ electrode element via an $n^{th}$ lead. Thus, pin P(1) may be coupled to lead E(1), and pin P(2) may be coupled to lead E(2), and an $N^{th}$ pin P(N) may be coupled to lead E(N), as shown. Leads E(1) through E(N) may be referred to as drive leads and leads C(1) through C(3) may be referred to as control leads. Other pins and/or different pinouts may be used for other functions, features or circuits. For example, other circuits may be included with (e.g., adhered to, embedded into) the multi-electrode array such as embedded into the substrate layer, such as a pulse oximeter, temperature sensor, and/or other circuitry and be provided a connection to the present system via the MPC.

The electrode array connector 1133 may be configured to be coupled to corresponding pins of an interface port of a stimulator as described herein. It is further envisioned that a locking mechanism may be provided to lock the electrode array connector to an interface port of a stimulator if desired.

While exemplary jumper settings are illustratively described, however, it should be understood that other jumper settings may also be used. In yet further embodiments, it is assumed that there may be two jumpers which may be decoupled from each other to identify a first array type (e.g., a percutaneous array) and coupled to each other to identify a second array type (e.g., a transcutaneous array). However, in the present embodiments, it will be assumed that in transcutaneous array type, a jumper (Jmp) inside the connector connects pins P(7) and P(9) and pin P(8) is unconnected. In percutaneous arrays, a jumper inside the connector connects pins P(8) and P(9) and pin P(7) is unconnected.

Figure 12:
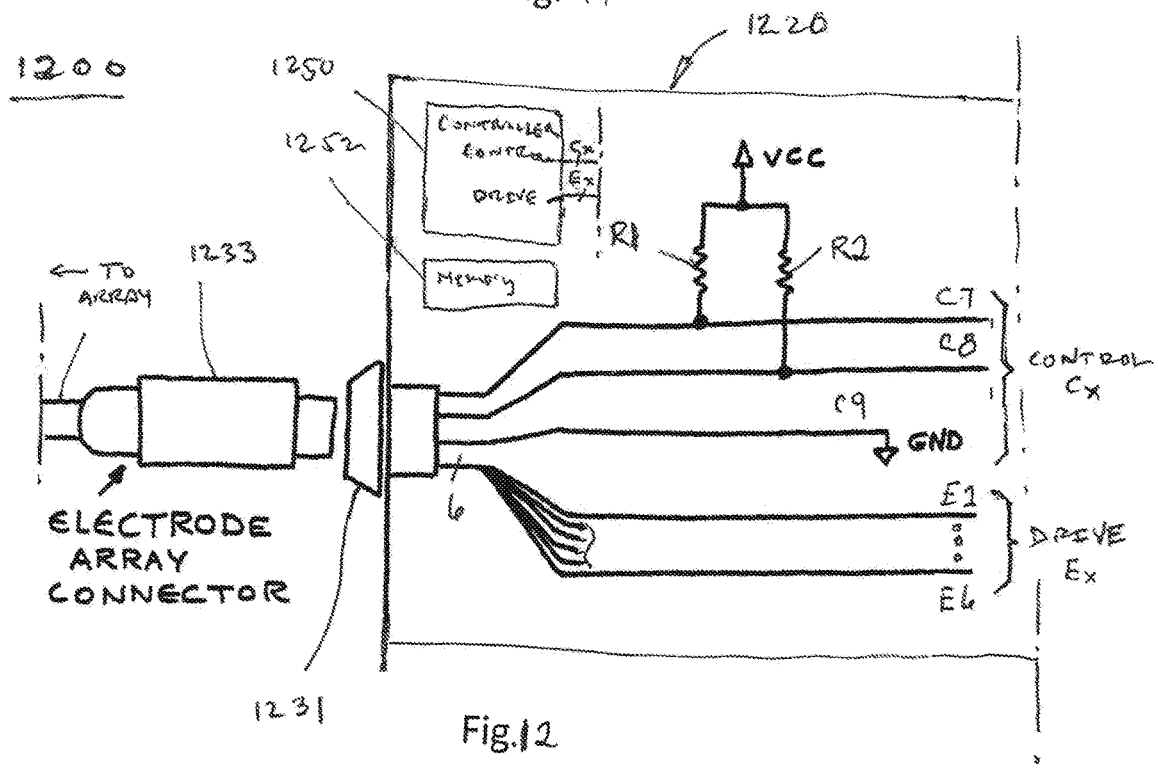
FIG. 12 shows a schematic block diagram of a circuit of a stimulator in accordance with embodiments of the present system.

FIG. 12 shows a schematic block diagram of a circuit 1200 of a stimulator 1220 in accordance with embodiments of the present system. The stimulator 1220 may include one or more of a controller 1250 (e.g., a processor), a memory 1252, an interface port 1231, leads E1 through E6 (generally Ex) and C7 through C9 (generally Cx), resistors R1 and R2, and a positive voltage source Vcc. The leads Ex may be referred to as drive leads and the leads Cx may be referred to as control leads. In accordance with embodiments of the present system, the controller 1250 may control the overall operation of the stimulator 1220. The controller 1250 may read information from the memory 1252 and may store information generated by the stimulator 1220 in the memory 1252.

The interface port 1231 may be configured to be coupled to an electrode array connector 1233 (e.g., an MPC) which may include corresponding control leads Cx and drive leads Ex. During operation, the controller 1250 may be configured to determine an array type of an array that is connected to the interface port 1231 of the stimulator 1220 using any suitable method such as sampling (sensor) signals from the control leads Cx.

The determined array type may be selected from a plurality of array types (e.g., a percutaneous array type or a transcutaneous array type) in the present embodiments. Thereafter, the controller may be configured to generate drive signals to drive the determined array type in accordance with settings for the determined array type. These settings may be stored in a memory of the system as array type information (ATI) and may include information related to signals patterns, amplitude, timing, etc. For example, a stimulus intensity and/or amplitude may be set based on the determined array type. For example, a transcutaneous electrode may require more energy (higher amplitude, wider amplitude range, higher frequency of pulses, longer pulse width, etc.) to go through skin and other tissues to stimulate the phrenic nerve as compared to a percutaneous electrode. These and/or other parameters may be optimized based on the electrode type. Further, these signals may be set by the ATI and be generated based upon a determined mode of operation as discussed herein. After generating the drive signals, they may be transferred to corresponding drive leads Ex (e.g., E1 through E9). The ATI may be stored in any format such as in an array type mode (ATM) table which defines a method to detect an array type and a mode of operation based upon signals received from the control leads Cx is shown in Table 1 below.

TABLE 1

Array Type Mode (ATM) Table

Control Leads
0 = low
1 = high

| C7 ("A" signal) | C8 ("B" signal) | Array Type | Stimulator Mode | Notes |
|---|---|---|---|---|
| 0 | 0 | NC (no connection) No array connected | Off | No drive signals generated in off mode |
| 0 | 1 | transcutaneous array | transcutaneous | Obtain transcutaneous signal settings to drive transcutaneous array |
| 1 | 0 | percutaneous array | percutaneous | Obtain percutaneous signal settings to drive percutaneous array |

Illustratively, resistors R1 and R2 may be each be coupled to control wire C7 and C8 (coming from connector pins 7 and 8 respectively), respectively, pulling up these two digital lines to a higher voltage (or a digital high state=1). Pin 9 may be coupled to a ground circuit such as a ground circuit of the printed circuit board (PCB) via lead C9.

Assuming that the electrode array connector 1233 may have a jumper configuration as illustrated by the electrode array connector 1133 shown in FIG. 11, array type modes (ATMs) (e.g., operational modes based upon an array type) may be defined by the system and/or user and may be detected by the controller 1250 through an analysis of signals input from the control leads Cx (e.g., C7 through C9 in the present embodiments). With regard to the control leads Cx, a signal sensed from lead C7 may be referred to as "A" signal and a signal sensed from lead C8 may be referred to as a "B" signal.

With reference to FIG. 12 and Table 1, when an array is not connected to the interface port 1231 of the stimulator 1220, neither of the control leads C7 and C9 are coupled to ground (e.g., there is no connection (NC)). Accordingly, both of the controls leads C7 and C8 (e.g., which are digital signals) may be driven to a digital high state by Vcc. In accordance with embodiments of the present system, the controller 1250 may sense that both of the control leads C7 and C8 are at digital high states (e.g., "A"=1 and B=1) and may refer to the ATI and determine that no array is connected and that a stimulator ATM should be off.

However, when an electrode array connector of a transcutaneous array type is connected to the interface port 1231 of the stimulator 1220, lead C7 may be jumped to lead C9 (ground) which may pull down the voltage within the lead C7 such that it will be at a digital low state (e.g., at a ground assertion level). However, as lead C8 is not jumped to lead C9 (ground), its signal may be pulled up to a digital high state by Vcc. Accordingly, the B signal, coming from lead C8 will be at a digital high state because it's unconnected. Thus, in this case A=0 and B=1. Accordingly, the controller 1250 may sense that A=0 and B=1 and may refer to the ATI and determine that a transcutaneous array is connected and that a stimulator ATM should set to a transcutaneous mode.

However, when an electrode array connector of a percutaneous array type is connected to the interface port 1231 of the stimulator 1220, the corresponding lead C8 may be jumped to lead C9 which may pull down the voltage within the lead C8 such that it will be at a digital low state ((e.g., at a ground assertion level). However, as lead C7 is not jumped to lead C9 (ground)), its signal may be pulled up to a digital high state by Vcc. Accordingly, a signal, coming from lead C7, will be at a digital high state because it's unconnected. Thus, in this case A=1 and B=0. Accordingly, the controller 1250 may sense that A=1 and B=0 and may refer to the ATI and determine that a percutaneous array is connected and that a stimulator ATM should set to a percutaneous mode.

Figure 13:
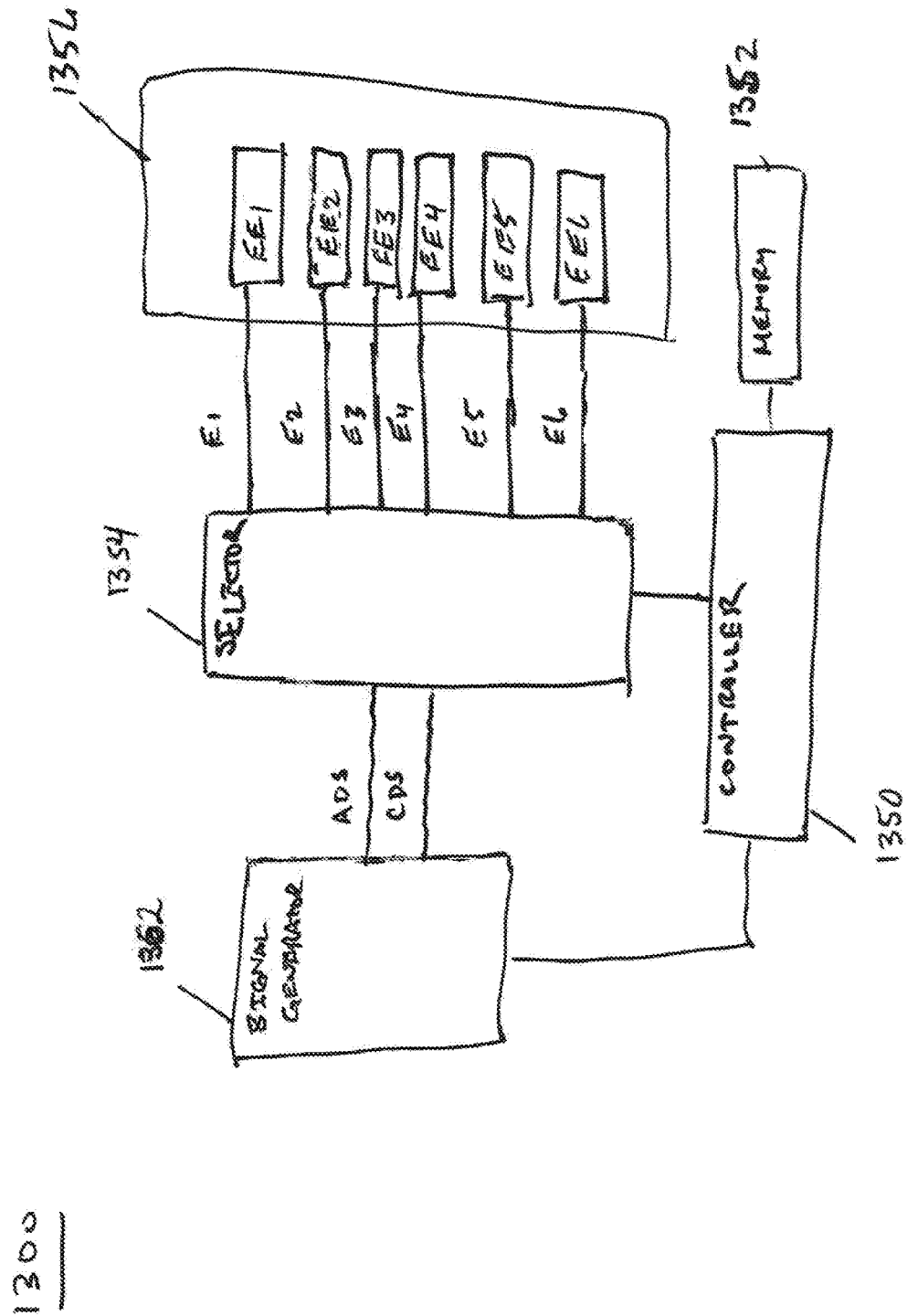
FIG. 13 shows a schematic block diagram of a portion of a stimulator in accordance with embodiments of the present system.

With regard to the electrode elements which are configured to form the array of electrode elements, these electrode elements may be driven by signals generated by a controller of the system to function as an anode, cathode, or neutral (e.g., no connection NC). Accordingly, an electrode combination may be formed by at least one electrode element driven as an anode and at least one electrode element driven as a cathode. This is illustrated with reference to FIG. 13 which shows a schematic block diagram of a portion of a stimulator 1300 in accordance with embodiments of the present system. The stimulator 1300 may include one or more of a controller 1350, a memory 1352, a signal generator 1362, a selector 1354, and an array of electrode elements 1356.

The array of electrode elements 1356 may include a plurality of electrode elements EE1 through EE6 (generally EEx) (e.g., EE(1) through EE(N), where N=6 in the present embodiments) arranged to form the array. Each EE1 through EE6 may be coupled to the selector 1354 via a corresponding lead E1 through E6, respectively, so as to receive drive signals from the selector. The controller 1350 may control the overall operation of the stimulator 1300 and may obtain operating instructions which may be stored in the memory 1352.

The signal generator 1362 may generate signals under the control of the controller 1350 and provide these signals to the selector 1354. These signals may include drive signals to drive the electrode elements EEx. The signal generator 1362 may form a single drive signal which may be split into anode and cathode drive signals or may form two separate signals: an anode drive signal (ADS) and a cathode drive signal (CDS).

The selector 1354 may be operative under the control of the controller 1350 to switch the signals received from the signal generator 1362 and selectively provide these signals to a selected one or more of the electrode elements EEx. The selector 1354 may include digital switches, analog switches, etc. for example as described herein. During operation, the electrode elements EEx, may be selected to be an anode, a cathode, or not connected (e.g., NC). It is envisioned further that more than one anode and more than one cathode may be selected.

In accordance with embodiments of the present system, to select the electrode combination, each of the electrode elements (e.g., the six electrode elements EE1 through EE6 in the present example) may be connected to a selector circuit (e.g., in a printed circuit board (PCB)) including a plurality of switches (e.g., analog switches, digital switches, solid-state switches, etc.) for example each with three positions: C—Cathode, A—Anode and NC—no connection. This selector circuit may include circuitry which may be similar to circuitry in the selector 1354 when the selector illustratively may include analog switches, digital switches and/or other circuitry, such as a multiplexer. The selector circuit may further include an anode circuit, a cathode circuit, and a no connection NC circuit. These circuits may be formed on a printed circuit board (PCB).

Figure 14:
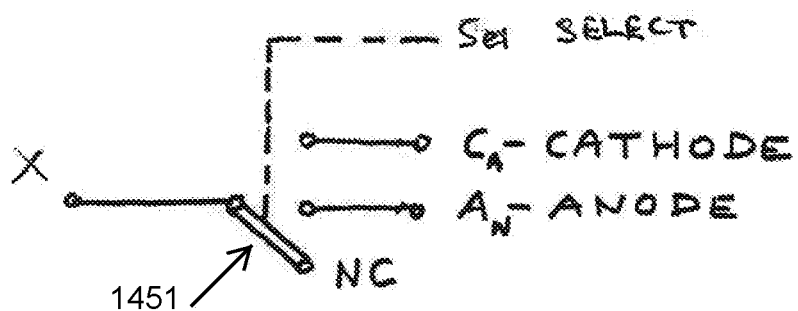
FIG. 14 shows a block diagram of a portion of an analog switch operating in accordance with embodiments of the present system.

FIG. 14 shows a block diagram of a portion of a switch 1400 such as an analog switch operating in accordance with embodiments of the present system. The switch 1400 may include anode "AN" contacts coupled to an anode circuit (e.g., in the printed circuit board (PCB)), cathode "CA" contacts may be connected to a cathode circuit (e.g., in the printed circuit board (PCB)), and the "NC" pins may be left unconnected (e.g., floating). A common contact X of each of analog switch may be coupled to the leads Ex (e.g., E1-E6) coming from each corresponding electrode element (e.g., EE1 through EE6 in the present embodiments).

Figure 15:
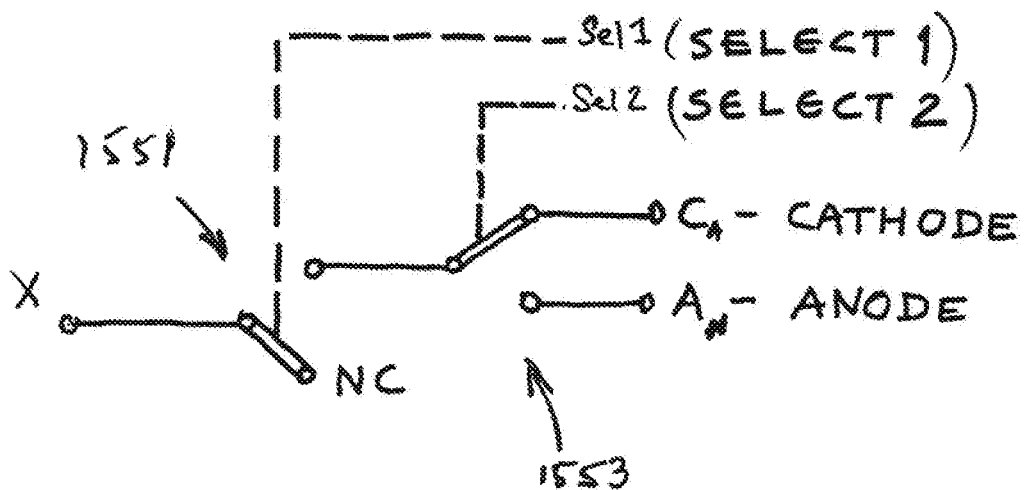
FIG. 15 shows a block diagram of a portion of an analog switch operating in accordance with embodiments of the present system.

Other selector circuits performing the same or similar function may also be suitably used. For the sake of clarity, FIG. 14 shows an analog switch 1400 having three positions (e.g., a three-pole switch). The analog switch 1400 may include a first pole switch 1451 having a selector contact Sel1 for receiving a select signal for driving a select circuit of the switch 1451. However, in accordance with embodiments of the present system, an analog switch may be formed using a circuit that may include two two-pole switches (e.g., analog switches) as shown FIG. 15 which shows a block diagram of a portion of an analog switch 1500 operating in accordance with embodiments of the present system. The analog switch 1500 may include first and second two-pole switches 1551 and 1553, respectively, each having a selector contacts Sel1 and Sel2, respectively, for receiving a select signal for driving a select circuit of the corresponding two-pole switch 1551 and 1553. Accordingly, a controller of the system may generate select signals to drive the selector circuit(s) as may be required for each analog switch. It is further envisioned that the selector may include any other suitable circuits performing similar functions as those performed by the selector in accordance with embodiments of the present system. Switches of the selector circuit may be controlled by a controller which may include any suitable logic device such as a microcontroller, a Field Programmable Gate Array (FPGA) or any other analog/digital control circuit by selecting one of the three corresponding positions, cathode, (C), anode (A), or no connection (NC).

During operation, a user such as a clinician may select at least one of the electrode elements as a cathode, and may select at least one of the electrode elements (e.g., hereinafter electrodes the sake of clarity) as an anode. However, in yet other embodiments, this selection may be performed automatically by the system alone and/or together with the user. The selection may be based upon a determination of an electrode combination that provides for example better stimulus at a lower threshold amplitude. This selection can be performed manually, automatically or in a combined form. A comparison of illustrative electrode combinations is shown with reference to FIGS. 16A through 16D, wherein FIG. 16A shows a block diagram 1600A of an anode and cathode selection in a multi-electrode array 1601A in accordance with embodiments of the present system; FIG. 16B shows a block diagram 1600B of an anode and cathode selection in a multi-electrode array 1601B in accordance with embodiments of the present system; FIG. 16C shows a block diagram 1600C of an anode and cathode selection in a multi-electrode array 1601C in accordance with embodiments of the present system; and FIG. 16D shows a block diagram 1600D of an anode and cathode selections in a multi-electrode array 1601D in accordance with embodiments of the present system. The multi-electrode arrays 1601A through 1601D may be similar to each other and electrodes (e.g., electrode elements) are numbered sequentially from 1 to 6.

It is envisioned that the cathode/anode order may be reversed and/or that other combinations may be provided. For example, the cathode may be electrode 2 and the anode may be electrode 5, but reversing the position, i.e., electrode 2 as anode and electrode 5 as cathode, may give better response depending on how close the cathode is to the phrenic nerve. It is further envisioned that more than one electrode may have the same function. In other words, there may be more than one anode and/or cathode as shown illustratively in FIG. 16C wherein electrode 2 is selected as a cathode and electrodes 5 and 6 are selected as an anode. For example, electrodes 2 and 3 may be selected as a cathode and electrode 5 as cathode. Similarly, electrodes 2 and 3 may be selected as the cathode and electrodes 4, 5 and 6 may be selected as anodes. It is envisioned that other combinations of electrode configurations may be selected in accordance with embodiments of the present system.

In accordance with embodiments of the present system the cathode and anode may be driven as a stimulating electrode (e.g., electrode element) as follows. For example, in a first case for proper stimulation of peripheral nerves, the preferential direction of a stimulus current may be by flowing current at the cathode (e.g., the negative electrode is used as a stimulating electrode) because it reduces voltage outside a neuronal cell membrane which causes depolarization and an action potential. When the cathode is used as the stimulating electrode, there may be a lower stimulus current required to elicit a motor response. A distance between the anode and an adjacent cathode may not be significant to the resulting stimulation and diaphragm contraction but having several electrodes to choose from may allow for a better return current path (e.g., may reduce the stimulation current and/or collateral stimulation, i.e., sensation, contraction or twitches in other muscles caused by the stimulation).

In accordance with embodiments of the present system, an electrode pair testing method (EPTM) to determine an electrode pair that generates proper stimulation, may be performed as follows:

Start with a first electrode pair (e.g., electrode 1 as the cathode and electrode 6 as the anode). Increase stimulation amplitude until a contraction is visible. If the stimulation achieves a discernible contraction, this electrode pair may be selected. If there is collateral stimulation then select another electrode pair using any suitable method such as by selecting another cathode such as by deselecting a current cathode (e.g., electrode 1 in current example) and selecting another electrode (e.g., electrode 2 in the current example) as the cathode. Thereafter, stimulation may be performed again. If no contraction is visible or discernible, select the next electrode as cathode, and so on, until at least one electrode pair is found to generate a good contraction without collateral stimulation or with reduced collateral stimulation. Reversing the electrodes forming the cathode/anode pair may improve stimulation results and may be performed on any one or more of the selected electrode pairs. Further, a next electrode (e.g., for selection as a cathode or electrode) may be selected from a next adjacent electrode or another. For example, illustratively, electrode selection may follow an order of electrodes 1 through 6 or vice versa.

With an array of 6 electrodes, a plurality electrode pair of combinations is possible. For example, with just with one electrode as a cathode and one electrode as an anode, 30 combinations are possible. With a plurality of electrodes as cathodes or anodes, the number of combinations is much greater. For example, Table 2 illustrates all electrode pair combinations for six electrodes which may be selected by embodiments of the present system.

TABLE 2

| Configuration | Combinations |
|---|---|
| One cathode, one anode | 30 |
| Two cathodes, one anode | 60 |
| Three cathodes, one anode | 60 |
| Four cathodes, one anode | 30 |
| Five cathodes, one anode | 6 |
| Two anodes, one cathode | 60 |
| Two anodes, two cathodes | 90 |
| Two anodes, three cathodes | 60 |
| Two anodes, four cathodes | 15 |
| Three anodes, one cathode | 60 |
| Three anodes, two cathodes | 60 |
| Three anodes, three cathodes | 20 |
| Four anodes, one cathode | 30 |
| Four anodes, two cathodes | 15 |
| Five anodes, one cathode | 6 |
| TOTAL | 602 |

During operation, testing all the different combinations may not be feasible because of time constrains. Accordingly, a method to expedite the selection of the electrodes is provided by a method of FIG. 17 which shows a block diagram 1700 of an anode and cathode selection in a multi-electrode array 1701 in accordance with embodiments of the present system.

With reference to FIG. 17, the electrode array 1701 includes a plurality of electrodes numbered from 1 to 6. In accordance with embodiments of the present system, a method to select electrode pairs is as follows: the electrode array 1701 may be divided into two regions: electrodes 1 to 4 and electrodes 3 to 6.

As the phrenic nerve is going to cross over the anterior surface of the anterior scalene muscle running diagonally, chances are that one of the two regions of the array will be closer to the nerve than the other.

During use, testing (e.g., in accordance with the EPTM discussed above) can start with electrodes 1 (cathode) and 4 (anode). The stimulus amplitude can be set to a value that typically generates a contraction that is visible and/or measurable, although it doesn't have to generate a full-breath contraction. The desired contraction may be some contraction that is visible and/or can be measurable (e.g., through use of a motion sensor). The desired contraction can be adjusted (e.g., increased or decreased) by adjusting the stimulus amplitude, frequency, pulse-width, etc.) after the desired electrode combination is determined.

In the event where this combination does not produce the desired contraction of the diaphragm and/or produces a contraction of the diaphragm together with collateral muscle movement (i.e., contraction of muscles other than the diaphragm), then electrodes 3 (anode) and 6 (cathode) may be tested next. Once it's determined which half of the array gives the better stimulation, for example as determined by observing the contractions of the diaphragm caused by the stimulation, by visual observation, through use of a sensor patch as described herein, palpation, using ultrasounds, fluoroscopy, etc., then testing can focus on the electrodes of that particular region of the electrode array, as follows: For example, if it is determined that electrode pair 1-4 gives better stimulation than electrode pair 3-6, then the system or the clinician (for example by pressing a key that selects the next pair of electrodes of the same group) may proceed testing electrodes within that particular region (e.g., in the region of electrode pair 1-4) of the electrode array such as electrode pairs 1-3, then 1-2, then 2-3, then 2-4, and then 3-4. If, on the other hand, the electrode pair 3-6 is determined to give better stimulation than electrode pair 1-4, the system or the clinician may proceed to test electrodes of that particular region of the electrode array as follows: electrode pairs 3-5, then 4-5, then 3-4, then 4-6, then 5-6. The testing may also include inversion of which electrode gives a better response as an anode or cathode. This, as well as other, electrode pair test patterns may be stored in a memory of the system and obtained during testing and may be updated by the system and/or user.

This way, the number of initial combinations may be limited to a desired number of combinations (e.g., six or twelve if all combinations of both groups are tested in the present illustrative embodiment with six electrodes although other numbers are also envisioned) as opposed to the maximum number of combination pairs (e.g., 30, etc.) for a given number of electrodes in an electrode array. This may reduce the time required for testing and/or a load on system resources.

In accordance with embodiments of the present system, testing may be performed automatically. For example, a given stimulus amplitude may drive each pair of electrodes and sensor patches may detect a resulting contraction. In a case wherein no contraction or an insufficient contraction is detected, the next electrode pair may be tested. As the maximum number of electrode combinations is very large, it is envisioned that the clinician may limit the electrode configuration to a given number. For example, the electrode groups used during stimulation may be limited just to one or two cathodes and one and two anodes. It is also envisioned that other limitations may be suitably applied by the clinician.

The electrode stimulus of each side of a patient may be manually adjusted using a user interface (UI) so that the patient experiences minimal if any, discomfort from the stimulation, a stimulation that produces a desired contractual level (e.g., a minimum contraction), and does not cause contraction in other muscles.

The stimulator may be capable of stimulating for example in five different stimulation modes (SMs) as will be discussed below although other modes of operation are also envisioned. After the electrode combination that provides better results is determined (e.g., better contraction of the diaphragm and/or little or no collateral contraction of collateral muscles), three amplitudes for example may be established to support different modes of operation as described herein with reference to FIGS. 18A-18D, 29-31 and 35-36.

It is envisioned that the different modes may be selected based on the respiratory status and condition of the patient, the treatment the patient is on, the length of time the patient is on the MV or is expected to be on the MV, the types of MV modes that can be used concurrently with the TDS based on the patient's condition and treatment, and other factors. The flexibility of selecting one of the five different modes and the adjustment of the amplitudes, frequency, pulse width, etc., corresponding to either smaller or stronger contraction allows for the clinician and/or system to better adjust the right pacing treatment for the patient. Of the modes usually available in all MVs—Assist control (AC), Pressure Control (PC), Pressure Support Ventilation (PSV) and SIMV (Synchronized Intermittent Mandatory Ventilation)—the respiratory therapist or clinician may select which one best fits the patient status condition and the desired treatment.

Figure 18A:
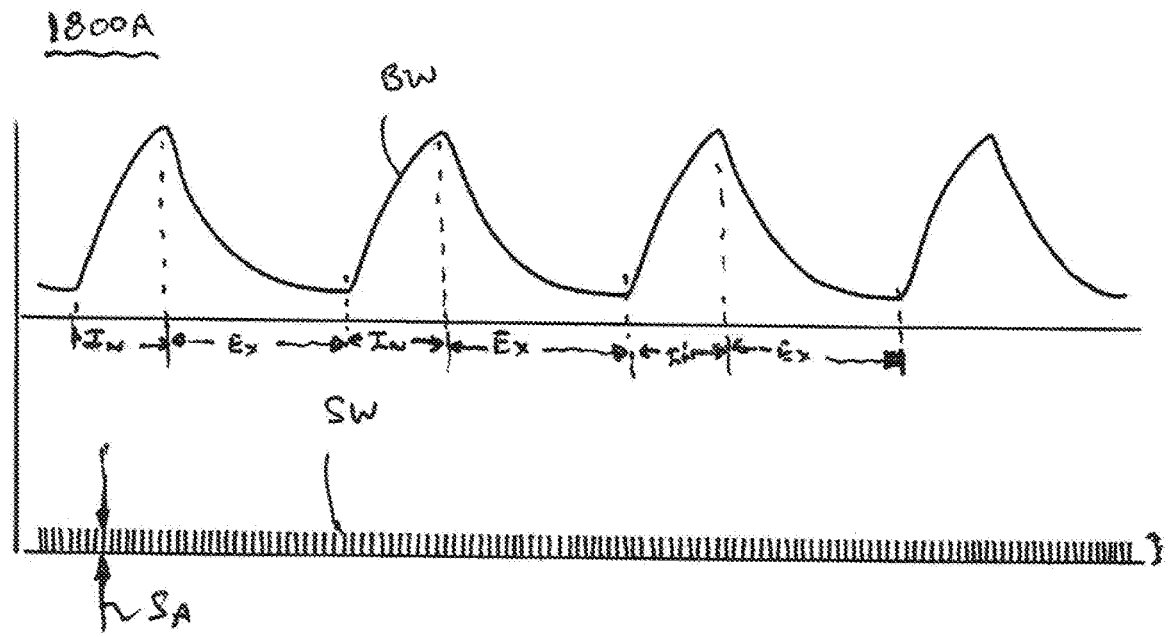
FIG. 18A shows a graph of a breathing waveform (BW) and a corresponding stimulation waveform SW in accordance with embodiments of the present system.
Figure 18B:
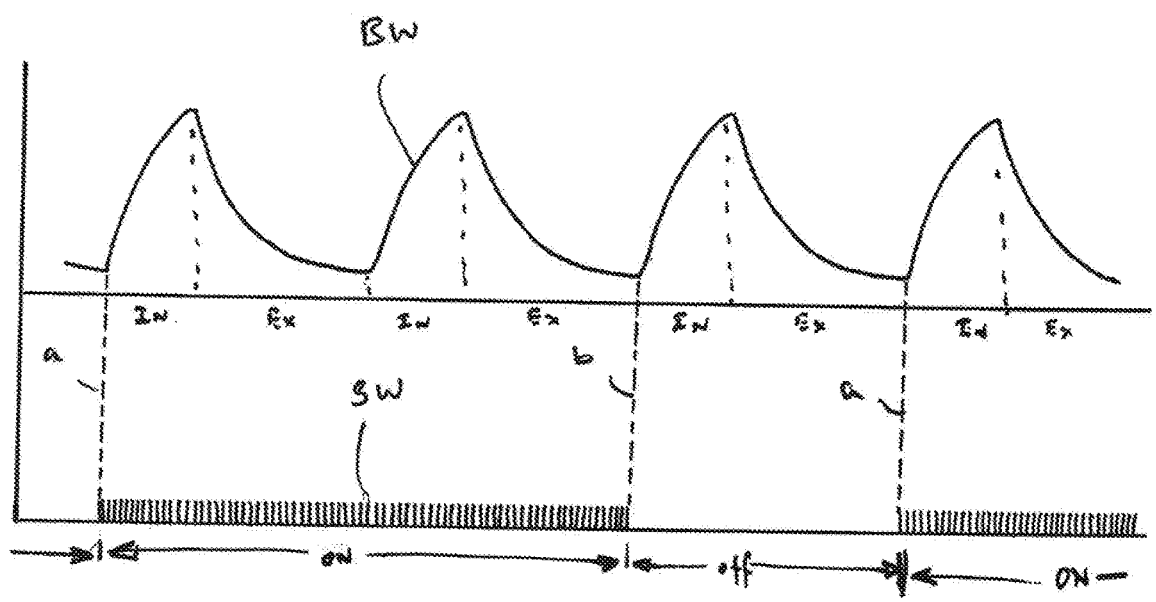
FIG. 18B shows a graph of a breathing waveform BW and a corresponding stimulation waveform SW in accordance with embodiments of the present system.
Figure 18C:
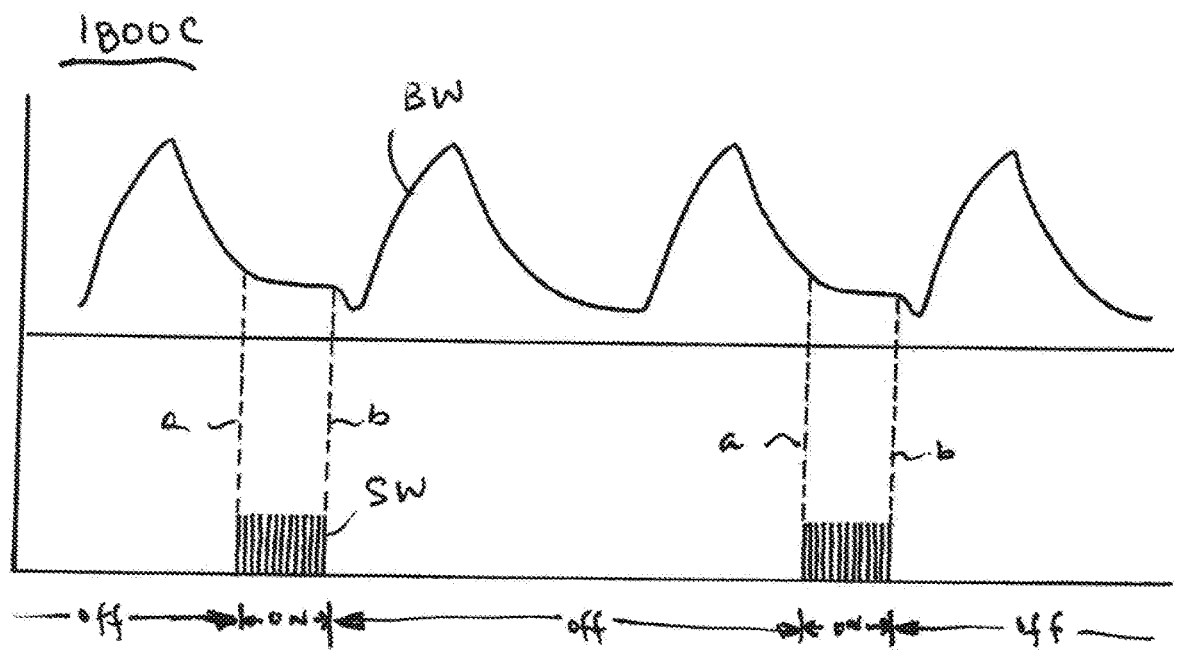
FIG. 18C shows a graph of a breathing waveform BW and a corresponding stimulation waveform SW in accordance with embodiments of the present system.
Figure 18D:
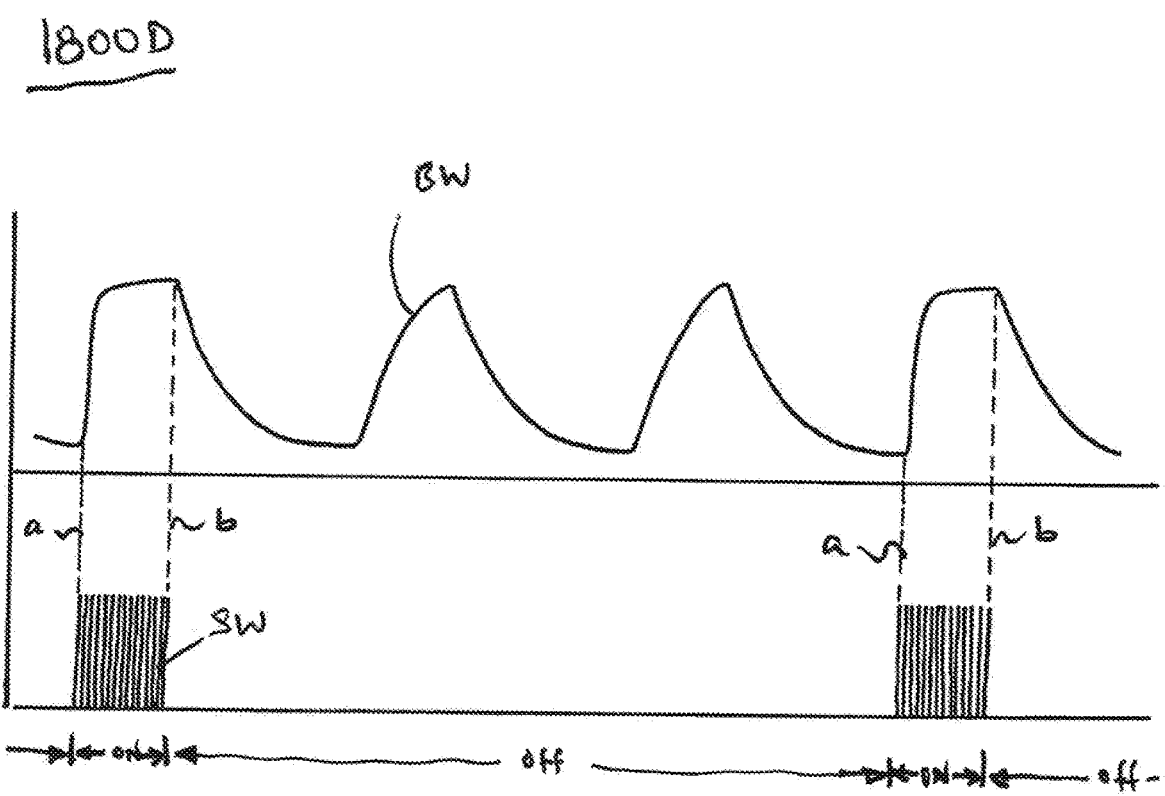
FIG. 18D shows a graph of a breathing waveform BW and a corresponding stimulation waveform SW in accordance with embodiments of the present system.
Figure 29:
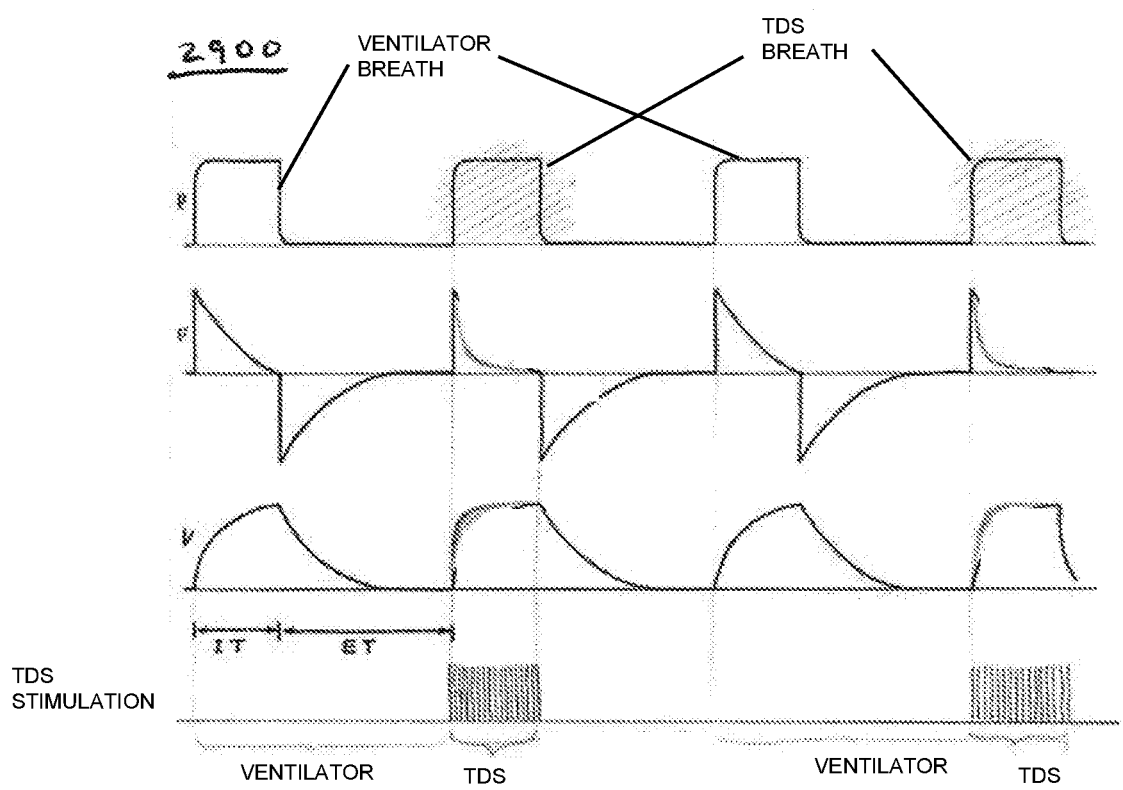
FIG. 29 is a graph of breathing and stimulus waveforms which illustrate adjustment of each of a mechanical ventilator (MV) and a Temporary Diaphragmatic Stimulator (TDS) to half of a desired respiratory rate such that together the desired respiratory rate is provided to a patient for proper oxygenation/ventilation in accordance with embodiments of the present system.
Figure 30:
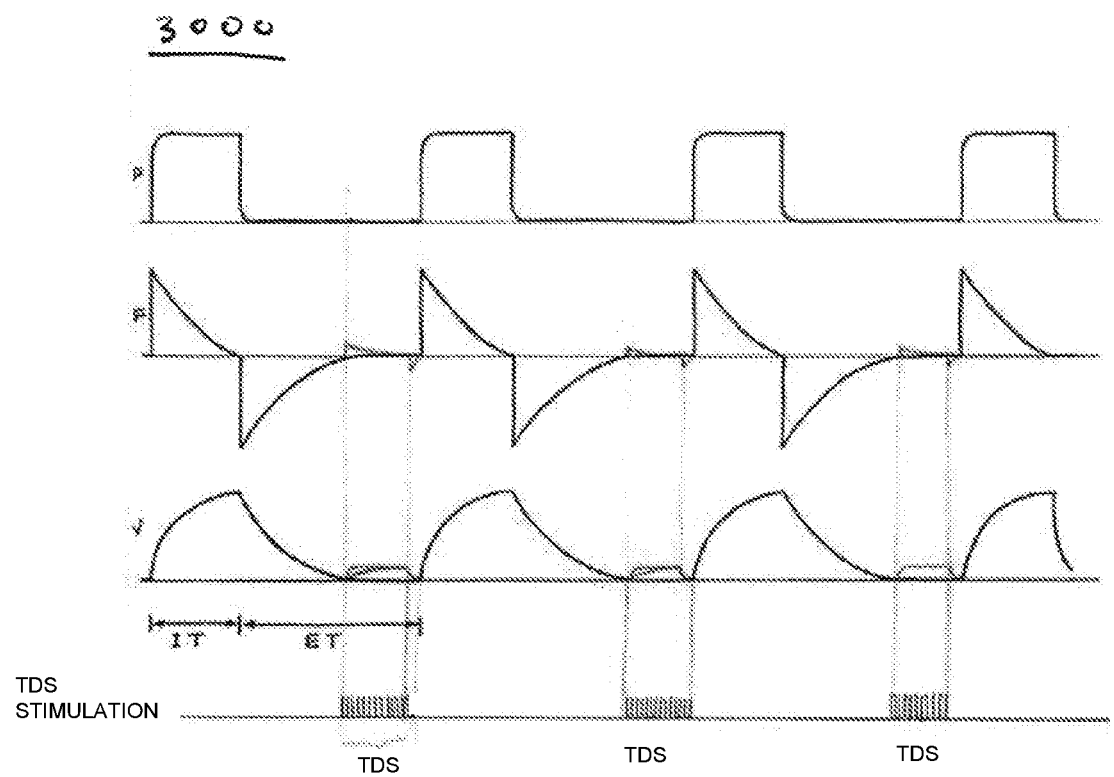
FIG. 30 is a graph of breathing and stimulus waveforms which illustrate how both the MV and the TDS are adjusted the proper respiratory rate for the patient in accordance with embodiments of the present system.
Figure 31:
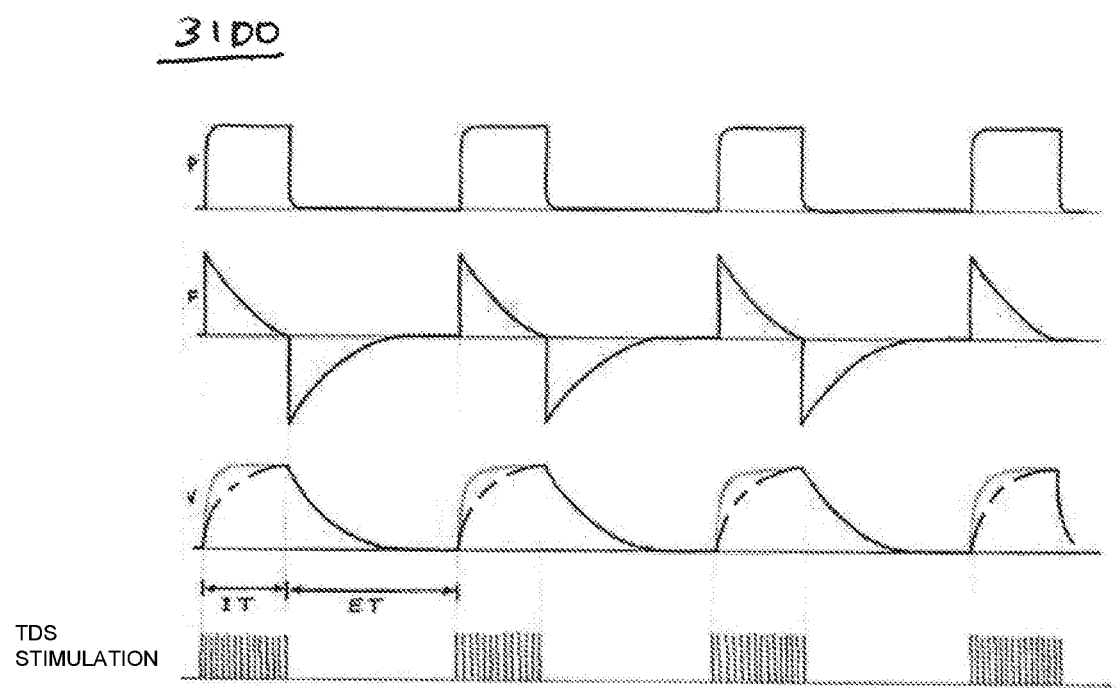
FIG. 31 is a graph of breathing and stimulus waveforms which illustrate a TDS generating stimulation during the entire inspiratory period of each breath in accordance with embodiments of the present system.
Figure 32:
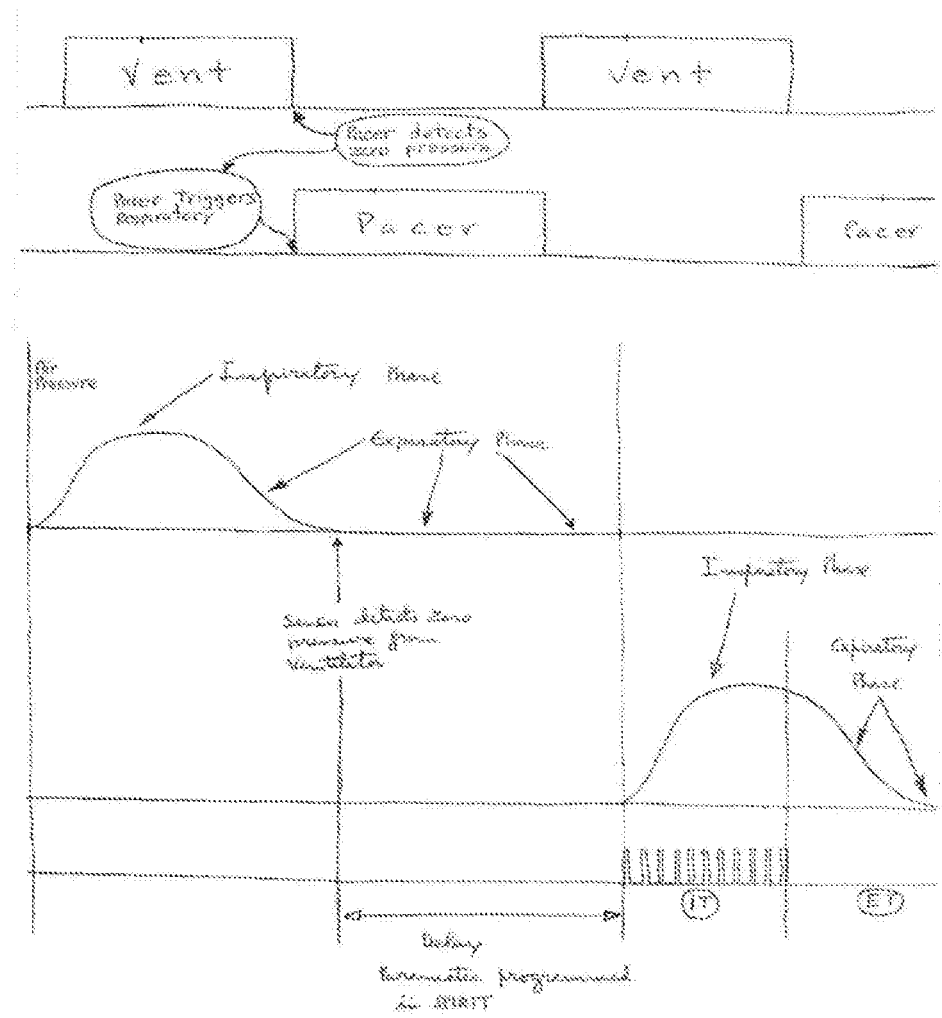
FIG. 32 is a graph of breathing and stimulus waveforms which illustrate an alternate operation of the MV and the stimulator in accordance with embodiments of the present system.
Figure 35:
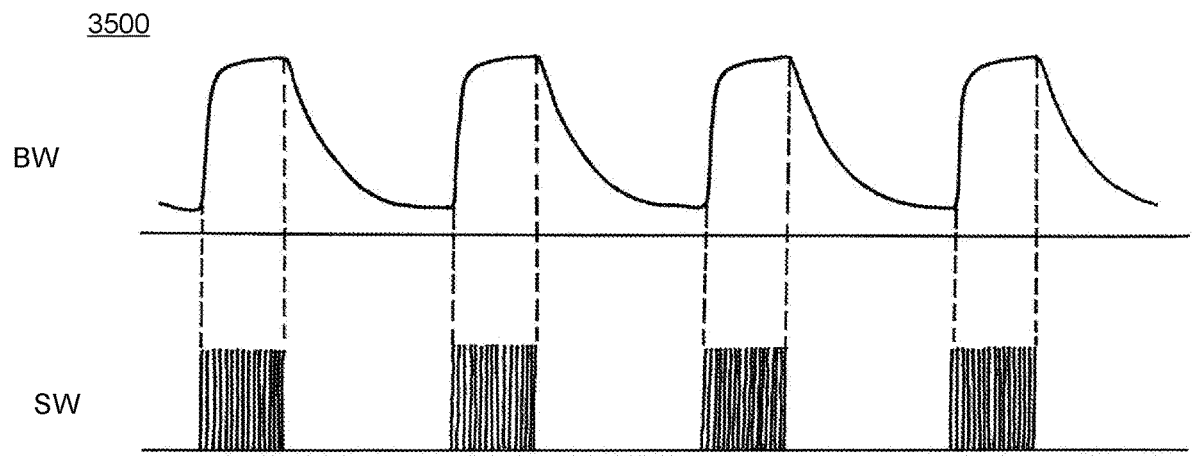
FIG. 35 shows a portion of a graph of a breathing waveform BW produced by a corresponding stimulation waveform SW having a fixed stimulus amplitude in accordance with embodiments of the present system.

The stimulation modes are as follows: Minimum Mode, Medium Mode, Maximum Mode, Combined Mode, and Support Mode, are discussed below for example with reference to FIGS. 18A through 18D, FIGS. 29-32 and FIG. 35 wherein: FIG. 18A shows a graph 1800A of a breathing waveform (BW) and a corresponding stimulation waveform SW in accordance with embodiments of the present system; FIG. 18B shows a graph 1800B of a breathing waveform BW and a corresponding stimulation waveform SW in accordance with embodiments of the present system; FIG. 18C shows a graph 1800C of a breathing waveform BW and a corresponding stimulation waveform SW in accordance with embodiments of the present system; and FIG. 18D shows a graph 1800D of a breathing waveform BW and a corresponding stimulation waveform SW in accordance with embodiments of the present system; FIG. 29 shows a graph 2900 of pressure, flow and volume breathing waveforms and a corresponding TDS stimulation waveform in accordance with embodiments of the present system; FIG. 30 shows a graph 3000 of pressure, flow and volume waveforms and a corresponding TDS stimulation waveform in accordance with embodiments of the present system; FIG. 31 shows a graph 3100 of pressure, flow and volume breathing waveforms and a corresponding TDS stimulation waveform in accordance with embodiments of the present system; FIG. 32 shows a graph 3200 of the breathing waveform periods of the ventilator (VENT) and the stimulator (PACER) and the corresponding breathing waveforms of ventilator and the stimulator in accordance with embodiments of the present system; and FIG. 35 shows a graph 3500 of a breathing waveform BW and a corresponding stimulation waveform SW in accordance with embodiments of the present system.

When the patient can breathe on his/her own, contraction of the diaphragm is caused by stimulation of the phrenic nerves with the physiological signals originating at the brain control centers. Electrical stimulation of the phrenic nerves can also achieve the same result, re-establish normal breathing to a patient, and provide the patient with a valid alternative to successfully replace the MV for one or more breadths.

In accordance with embodiments of the present system, a train of electrical pulses is utilized to contract the diaphragm. When the phrenic nerve is stimulated, the stimulus is propagated down the diaphragm which contracts for the period of time the pulses are delivered to the phrenic nerve. When contracting, the diaphragm moves down towards the abdominal cavity and the negative pressure created inside the lungs forces air to be inhaled into the lungs. This is the inspiratory period or inspiratory phase of the breath. When no pulses are delivered to the phrenic nerves, the diaphragm stops contracting and relaxes to its normal position, moving up into the abdominal cavity and the air is exhaled out of the lungs. This is the expiratory period or the expiratory phase of the breath.

When the patient has ventilatory support via a MV, the concurrent stimulation of the phrenic nerves to prevent atrophy of the diaphragm has to be such that the stimulation does not interfere with the main work of the MV. In accordance with embodiments of the present system, the main goal to keep the diaphragm active can be achieved by stimulating the phrenic nerves such that the diaphragm doesn't atrophy. Exercising the diaphragm while the patient has ventilatory support should be done such that it doesn't disturb the MV work. For example, stimulation may be used with a very small amplitude so that is creates a slight contraction of the diaphragm. As it doesn't disturb the MV work, this stimulus can be continuous or done periodically. In either case (i.e., continuous or periodic stimulation), because a very mild contraction is produced, the stimulus may occur in the inspiratory and/or the expiratory phases.

In a case wherein the stimulation has a higher amplitude such that a shallow breath is produced as a result of the stimulation, the stimulation may still be utilized without affecting the ventilatory support the patient is getting from the MV. As the most important work done by the MV occurs during the inspiratory phase (or inspiratory period), it is envisioned that a larger stimulus amplitude to stimulate the diaphragm occurs during the last portion of the expiratory phase, when most of the air inside the lungs has exited the lungs. In accordance with embodiments of the present system, stimulation causing some contraction above the minimum may not affect the MV support. Careful adjustment of the amplitude may be performed by verifying the work of the MV, the settings and the proper gas exchange of the patient.

In a case wherein stimulation is of a much higher amplitude such that it would cause a full breath, careful adjustment of the MV settings is needed so that, although disturbing the MV, proper ventilatory support and the resulting gas exchange of the patient remains correct. For example, the MV may be set to a mode so as to allow the patient to create his/her own spontaneous breaths although these breadths would be provided by stimulating the phrenic nerve in accordance with embodiments of the present system.

Depending on the condition of the patient and treatment the patient is getting, the contractions to exercise the diaphragm to prevent it from being atrophied should be adjusted in light of the main objective of keeping the patient alive, breathing with the proper gas exchange and recovering from his/her condition. Due to the above considerations, in certain cases it may not be possible to have mild or large contractions of the diaphragm during certain periods of the treatment (e.g., stimulation may be performed intermittently skipping one or more breaths between stimulation). Optionally, the amplitudes may be lowered to a value corresponding to a smaller contraction that does not affect MV support.

When it's possible to allow larger contractions (i.e., larger than the minimum contraction) such that a shallow breath occurs as a result of the stimulation, the stimulation may be provided for example during the expiratory phase. In this case, the MV settings may have to be adjusted to allow the contraction without changing the gas exchange of the patient.

When the patient has shown signs of recovery and the treatment allows full breaths, a larger amplitude may be used to fully exercise the diaphragm and more effectively reduce or eliminate atrophy of the diaphragm muscle fibers. In this case, the MV operation may still act as the main ventilatory support of the patient but full breaths generated by the TDS may for example be interposed with the breaths generated by the MV or even in support of all the MV breaths, for example as illustrated in FIG. 32.

In all these cases, the stimulus amplitude should be adjusted depending on the patient's condition. It is envisioned that the minimum or threshold amplitude may vary from patient to patient and may also depend on the drug treatment the patient is on. For example, in some patients a very small amplitude may be enough to generate a minimum contraction or threshold contraction while in other patients, a larger amplitude may be necessary to generate the same minimum contraction or threshold contraction.

Following is a description of five different modes of stimulation in accordance with embodiments of the present system.

Minimum Mode

With reference to FIG. 18A, in Minimum Mode, the stimulation is very small (as illustrated by a stimulation amplitude (SA)) so that a minute contraction of the diaphragm is elicited and may be detected. This stimulation may be called a threshold stimulation and is shown in the stimulation waveform as an impulse waveform SW with the amplitude SA. With reference to the breathing waveform BW, it is seen that the contraction of the diaphragm, being very small does not cause a breath or any change in the pressure, flow and volume set by the MV. The goal for this mode is to allow the diaphragm to be constantly exercised, keeping it minimally contracted, without affecting the MV settings and the treatment of the patient.

With reference to graph 1800B, in some instances, instead of the diaphragm being constantly exercised, it can be exercised for some period of time followed by a period of no stimulation for example to prevent possible muscle fatigue. This is shown in FIG. 18B, wherein the stimulation may be intermittent and in synchronization with predetermined events in the breathing waveform (BW) such as the start of an inspiratory period (In) (e.g., see dotted line (a)) and a may be discontinued at the end of a second expiratory (Ex) period after the inspiration period (e.g., see dotted line (b) BW waveform). The stimulation may be discontinued for example for one complete breath before restarting at the beginning of the next breath. This is illustrated with reference to on and off intervals as shown in the graph 1800B. It is also envisioned that stimulation may also occur for one period of time and thereafter be discontinued for another period of time which periods may be the same or different. For example, there may be stimulation during three minutes, with no stimulation for the following two minutes. As seen for example in the graphs 1800A and 1800B, due to the minute contraction of the diaphragm, there is no modification of the tidal volume waveforms that are attributed to the MV support provided to the patient.

The parameters for this mode may include pulse amplitude and repetition rate. The amplitude may be adjusted manually and when a threshold value is found, this value may for example be stored in a memory of the system for later use.

For example, the stimulus amplitude value may be determined by slowly increasing the amplitude until a small contraction is detected using normal methods such as visual observation of the abdomen, palpation, fluoroscopy, spirometry, etc., and/or other methods to measure tidal volume. In accordance with embodiments of the present system, stimulation may not be synchronized with the MV breaths. Optionally, stimulation may be synchronized with the MV for a determined number of breaths (e.g., 3 breaths although other numbers are also envisioned and may be set by the system and/or user), with a pause in stimulation for a determined number of breaths (e.g., 1 breath although other numbers are also envisioned and may be set by the system and/or user) and/or a period of time, e.g., stimulating during all the breaths for 5 minutes, then no stimulation for 5 minutes. In the embodiment illustrated, stimulation is shown starting at the beginning of the inspiratory period of the next MV breath.

In accordance with embodiments of the present system, timing of stimulation may be entered by a user such as a clinician. For example, the user may select to generate a stimulation period (e.g., an on period) and then a pause (e.g., an off period which is no stimulation) period to be generated by the system as well as associated settings (e.g., amplitude, etc.) and store this setting with a descriptor (e.g., a setting name as may be set by the system or user) in a memory of the system. A value of these on and off periods may be set by the system and/or user and may range as little as from one minute or less to 1 hour or more and the pause period may also range from as little as one minute or less to one hour or more although other values for the ranges are also envisioned. Moreover, it is envisioned that the ranges may be variably set for example about a set value (e.g., 10 minutes+/−1 minute as may be variably determined by the system and/or the user).

Medium Mode

In Medium Mode, the stimulation may be performed at an amplitude which is determined to cause a shallow breath by the patient, but not enough to allow the patient to sustain proper ventilation without the MV. The main goal for this mode is to allow the diaphragm to be periodically exercised without affecting the treatment of the patient and the MV settings.

The parameters for this mode may include pulse amplitude, repetition rate and pulse train slope. The amplitude may be adjusted automatically and/or manually until a shallow breath is achieved as may be sensed by a user or the system (e.g., based upon a comparison). When a value is determined for the amplitude, it may be stored in a memory of the system for later use. Stimulation may then be optionally synchronized with the MV breaths for example as shown in FIG. 18C. With regard to the repetition rate, a value for this rate may be determined by the system and/or may be entered by the clinician and stored in memory of the system for later use. An envisioned range may vary from every breath (1:1) to one breath for every 60 MV breaths (1:60) although a time duration may also be utilized for providing/not providing stimulation. However, other values and/or ranges are also envisioned. For example, stimulation may start at about halfway of a corresponding expiratory period of the programmed MV breaths and may end before the beginning of the inspiratory period of the next MV breath (e.g., see, graph 1800C). As shown in FIG. 1800C, the pressure waveform is slightly modified showing a rise in the pressure during the stimulation. It is envisioned that stimulation should stop before the start of the next breath generated by the MV so that the MV support is not interfered with by the TDS stimulation.

Maximum Mode

In Maximum Mode, a stimulation may be performed at maximum amplitude to produce a volume identical or similar to that of an MV breath. A goal for this mode is to allow the diaphragm to be fully exercised such that it generates full breaths. Optionally, the amplitude may be adjusted to generate a large breath but not as large as the one generated by the MV and corresponding to the optimal tidal volume of the patient (i.e., the volume of air inspired in each breath). This may be illustrated with reference to graph 1800D illustratively shown in FIG. 18D and FIG. 32 wherein the full breaths occur during the MV inspiratory period. During this stimulation, the system or a clinician may adjust the amplitude of the stimulation pulses (e.g., see waveform SW) until a full breath may be determined using any suitable method. For example, the user may manually compare the waveform of the MV breath and the stimulator breath and adjust the amplitude of the stimulation pulses until a desired waveform such as the waveform BW shown in graph 1800D or the like may be obtained. This mode may be desirable when the patient is able to be on SIMV (synchronized intermittent mandatory ventilation) or AC (assist control) mode of the MV or any other mode that allows the ventilator to suspend ventilatory support and breaths are skipped when spontaneous breaths from the patient are detected.

The parameters for this mode may include amplitude, repetition rate and pulse train slope. The amplitude may be adjusted automatically and/or manually and may be stored in a memory of the system for later use. Stimulation may be performed periodically and before the start of a MV breath, otherwise, the MV begins another breath on its own. When diaphragmatic contraction begins, the MV may detect a drop in pressure inside the lungs as if it was due to a spontaneous breath, and does not trigger the next breath. The lungs may then be filled with air solely due to the contraction of the diaphragm. After the breath generated by the TDS, no further stimulation occurs and the MV should resume generating breaths. The repetition rate may be entered by the clinician or obtained from a memory of the system. An envisioned range may be from one stimulator breath for every two MV breaths (1:2) to one stimulator breath for every 60 MV breaths (1:60), however, other values and/or ranges are also envisioned.

Combined Mode

In a Combined Mode, the stimulation may be programmed with two simultaneous modes: Minimum and Medium stimulation, Minimum and Maximum stimulation or Medium and Maximum stimulation.

a) Minimum stimulation and Medium stimulation. The repetition of each may be programmed. For example, the minimum stimulation may be performed continuously or for a certain number of breaths and medium stimulation may be programmed once every 6 MV breaths during which stimulation with the minimum amplitude is halted. However, other values and/or ranges of values are also envisioned.

b) Minimum stimulation and Maximum stimulation. The repetition of each may be programmed. For example, the minimum stimulation may be performed every breath and maximum stimulation may be programmed once every 8 MV breaths, however, other values and/or ranges of values are also envisioned.

c) Medium stimulation and Maximum stimulation. The repetition of each may be programmed. For example, the medium stimulation may be performed every 3 MV breaths and maximum stimulation may be programmed once every 12 MV breaths, however, other values and/or ranges of values are also envisioned.

Support Mode

In Support Mode, the stimulation may be programmed to occur on all MV-generated breaths for example as illustratively shown in FIGS. 31 and 35 described further herein below. This mode is similar to Maximum Mode but instead of allowing one MV breath to be replaced by a TDS breath periodically, there may be stimulation on all MV breaths. The stimulation amplitude doesn't have to be adjusted to a maximum amplitude value because the MV will still provide all the breaths to the patient. In this mode, the TDS will simply support the MV breath. Accordingly, a lower amplitude value may be used to create some diaphragmatic contraction that supports the MV-generated breaths. It is envisioned that this amplitude may range from the minimum amplitude necessary to cause a discernible contraction to the maximum amplitude necessary to cause the optimal tidal volume of the patient. This amplitude may be adjusted depending on the condition and treatment of the patient. The stimulus pulse train generated by the TDS may start at the beginning of the inspiratory phase and may end at the end of the inspiratory phase coinciding with the full inspiratory phase of the MV. The stimulation should occur during the inspiratory phase and may continue for its entirety for all breaths. Illustratively, the pulse train may be identical to that used in the Maximum Mode.

In this mode, the MV should be adjusted to a mode that may allow spontaneous breaths without skipping the normal mandatory MV breath. Depending on the MV mode selected and not to disturb the operation and settings of the MV, a delay in the stimulation pulse train produced by the TDS may be utilized at the start of the MV inspiratory phase of the breath. In this way, the stimulation may occur during the inspiratory phase but does not begin with the start of the inspiratory phase. The parameters for this mode may include pulse amplitude and pulse train slope. The amplitude may be adjusted manually and may be stored in a memory of the system for later use. Due to the additional support of the breath due to the diaphragm contraction, the volume waveform (as well as the pressure and flow waveforms) visualized on the MV or a patient monitor will include the component created by the TDS stimulation.

Some distortion of the typical waveform may occur, however, for a small stimulus amplitude, this component may not be clearly visible. For larger amplitudes, the combined overall waveform may have a sharper rise at the beginning of the inspiratory period due to the TDS stimulation component as for example illustrated in FIGS. 31 and 35. As described herein, a pulse train slope may be used to allow for a smoother contraction of the diaphragm thereby causing a more gradual rise of the tidal volume (e.g., refer to FIGS. 34B to 34E). The resulting waveform visualized in the MV may have a similar shape to the waveform caused by the MV without any TDS support (e.g., refer to FIGS. 35 and 36). The slope may be adjusted so that the effects can be immediately visualized (e.g., refer to FIGS. 26A and 26B).

Figure 26A:
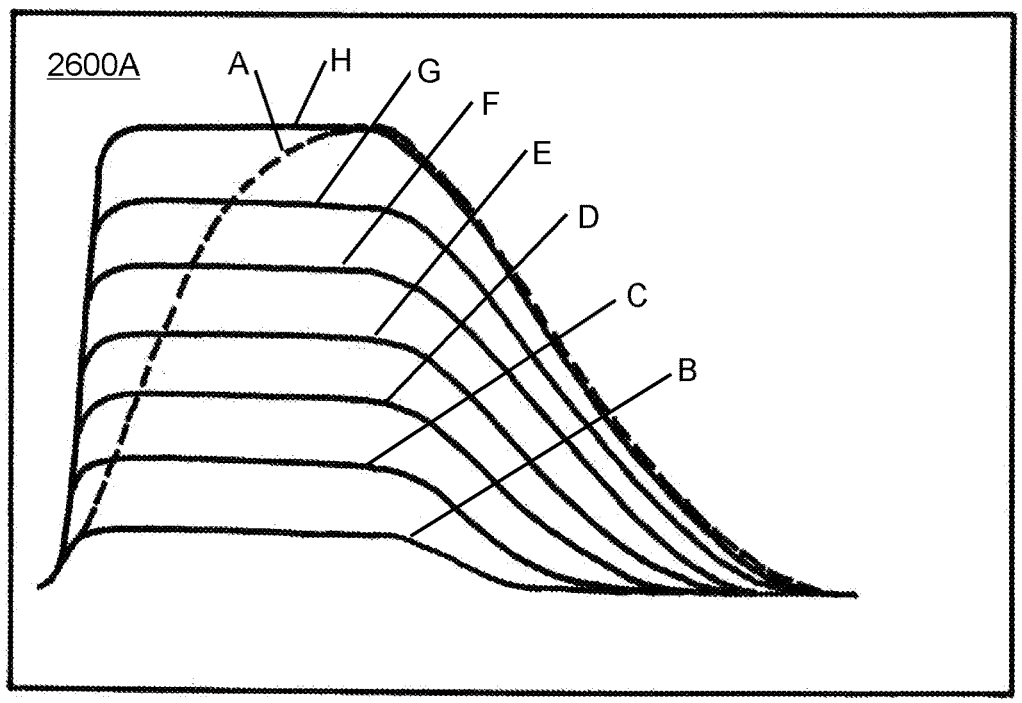
FIG. 26A shows a graph 2600A including portions of breathing waveforms in accordance with embodiments of the present system.
Figure 26B:
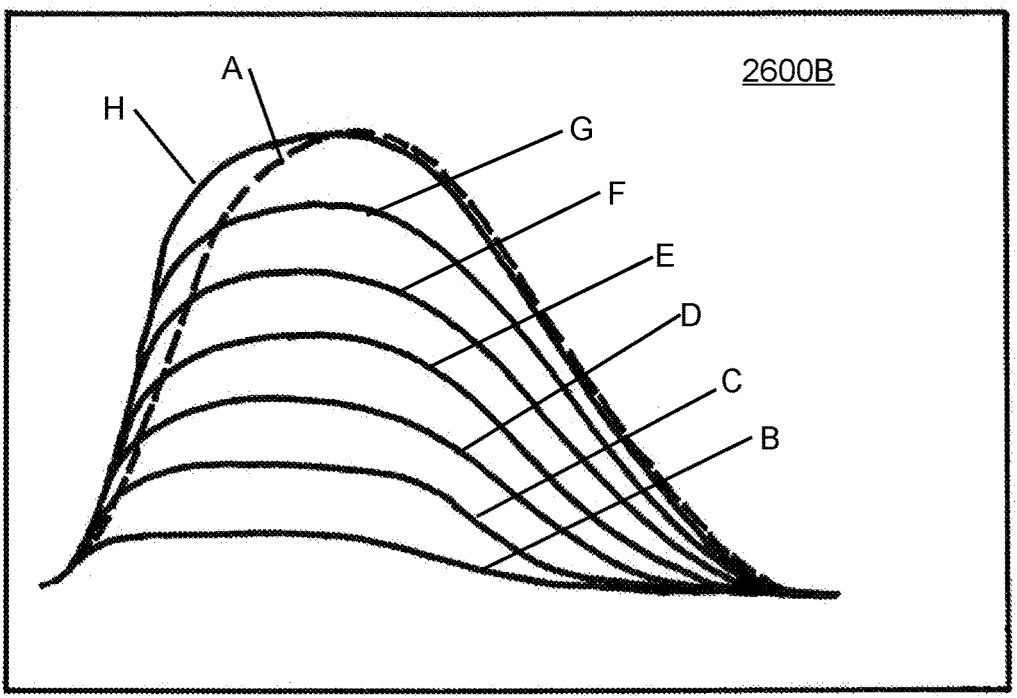
FIG. 26B shows a graph 2600B including portions of breathing waveforms in accordance with embodiments of the present system.

In FIG. 26A, multiple waveforms are shown as solid lines B-H that represent the tidal volume created due to contraction of the diaphragm with stimulus pulse trains with no slope, i.e., all pulses within a given waveform with the same amplitude such as illustratively shown in FIGS. 34A and 35. In FIG. 26A, the dashed line A represents the tidal volume created due to the MV action without diaphragm contraction produced by the TDS. FIG. 26B shows multiple waveforms as solid lines B-H that represent the tidal volume created due to contraction of the diaphragm with stimulus pulse trains with a slope, i.e., a portion of all pulses with a different amplitude (e.g., refer to FIGS. 34B to 34E and 36). The waveforms approach that of the MV waveform (e.g., see dashed line A of FIG. 26B), providing a smoother breath. Changes in the amplitude stimulus may be utilized in Medium, Maximum, Combined and the Support Mode when both the MV and the TDS concurrently deliver each breath.

To adjust the contraction for the desired effect, stimulation can be adjusted in the inspiratory phase of a breath as for example illustrated in FIGS. 26A and 26B. However, introducing contraction of the diaphragm during the inspiratory phase may disturb the breath cycle. In accordance with embodiments of the present system, stimulation may be performed during the expiratory phase of the breath because there may be less interference to the MV work and because the expiratory period is normally longer than the inspiratory period. To further minimize this interference, the stimulation period may be relatively short compared to the entire expiratory period.

Figure 40A:
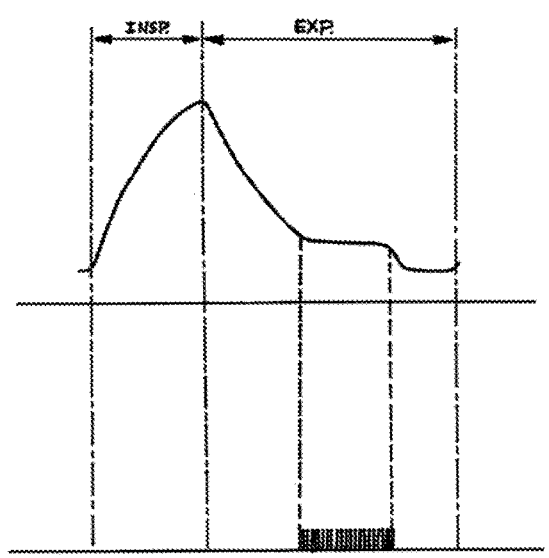
FIG. 40A shows a portion of a graph of a breathing waveform produced by a corresponding stimulation waveform with a threshold stimulus amplitude in accordance with embodiments of the present system.
Figure 40B:
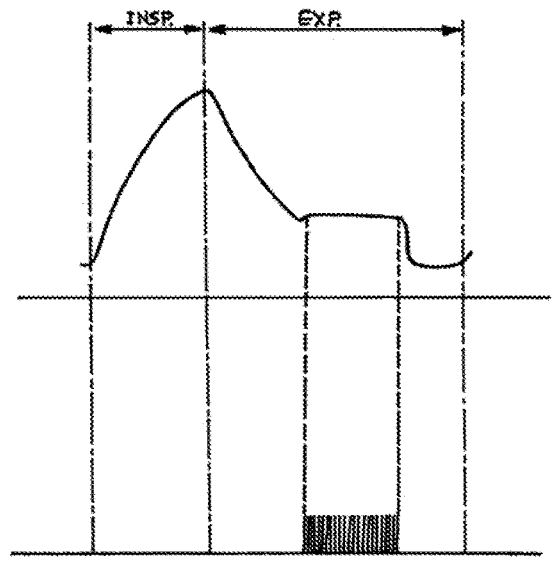
FIG. 40B shows a portion of a graph of a breathing waveform produced by a corresponding stimulation waveform with a low stimulus amplitude in accordance with embodiments of the present system.
Figure 40C:
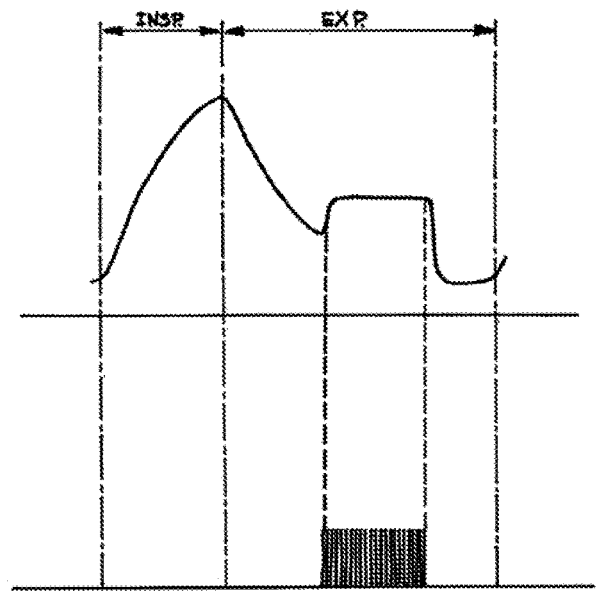
FIG. 40C shows a portion of a graph of a breathing waveform produced by a corresponding stimulation waveform with an intermediate stimulus amplitude in accordance with embodiments of the present system.
Figure 40D:
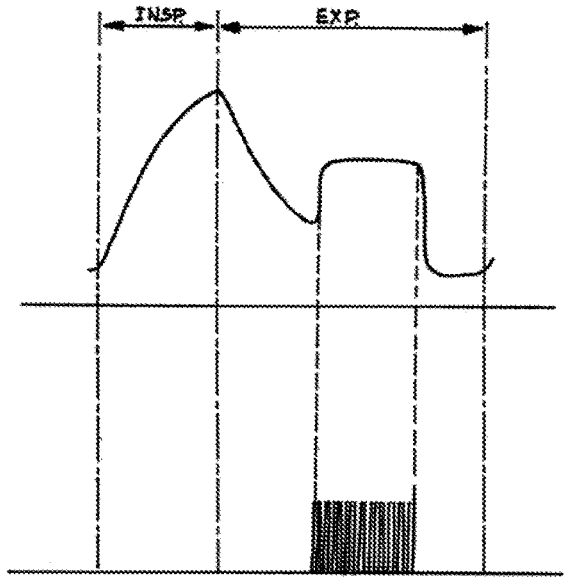
FIG. 40D shows a portion of a graph of a breathing waveform produced by a corresponding stimulation waveform with an intermediate stimulus amplitude in accordance with embodiments of the present system.
Figure 40E:
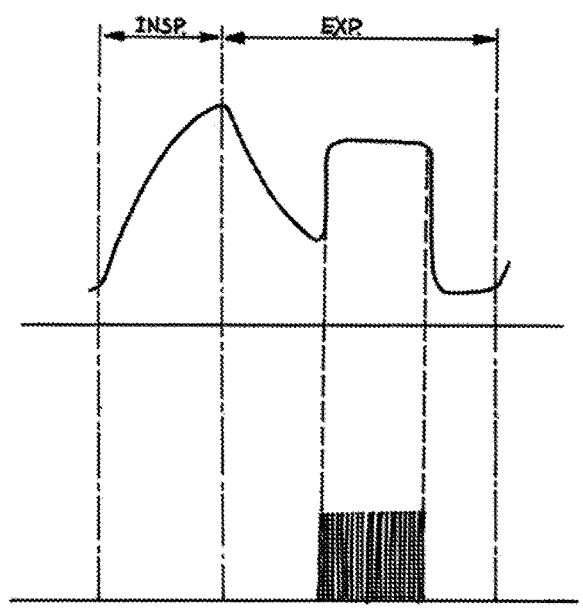
FIG. 40E shows a portion of a graph of a breathing waveform produced by a corresponding stimulation waveform with an intermediate stimulus amplitude in accordance with embodiments of the present system.
Figure 40F:
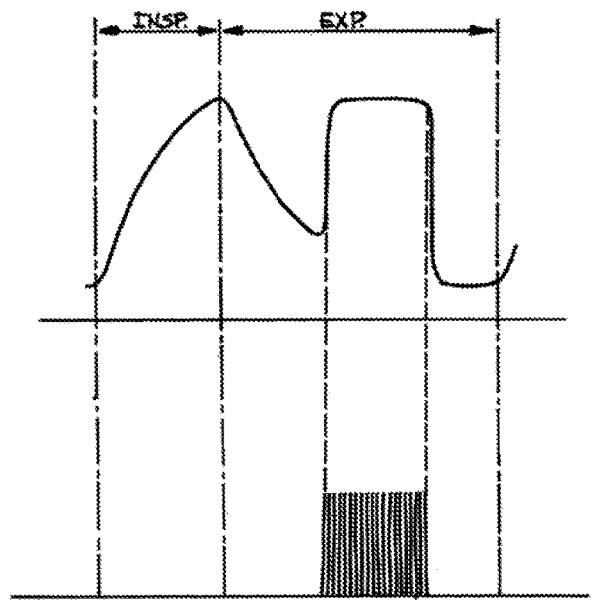
FIG. 40F shows a portion of a graph of a breathing waveform produced by a corresponding stimulation waveform with a maximum stimulus amplitude in accordance with embodiments of the present system.

For example, FIGS. 40A to 40F illustrate the effect of the contraction at varying amplitudes showing in FIG. 40 A the lowest amplitude (threshold) to cause minimum contraction, with FIGS. 40B to 40E with increasing amplitudes and showing the contraction caused by these amplitudes, and FIG. 40F showing the amplitude and its corresponding maximum contraction corresponding to the tidal volume generated by the MV. It is envisioned that these waveforms may differ depending on the MV modes.

As readily appreciated, the tidal volume produced when both the MV and the TDS concurrently deliver each breath may not be the same as without TDS stimulation. This is due to the fact that when there is electrical stimulation, the diaphragm contracts. Accordingly, the volume of the thoracic cavity is expected to be larger when the diaphragm also contracts on its own rather than when simply pushed down by positive air pressure generated by the MV. The visualized peak pressure of the tidal volume when there is combined MV breath and TDS stimulation may be not be the same as when no TDS stimulation is provided. With a larger internal volume inside the lungs, the MV settings (i.e., pressure, flow, and volume) may have to be adjusted because more air is drawn into the lungs. The adjustments of the MV settings depend on the patient condition and treatment.

Figure 36:
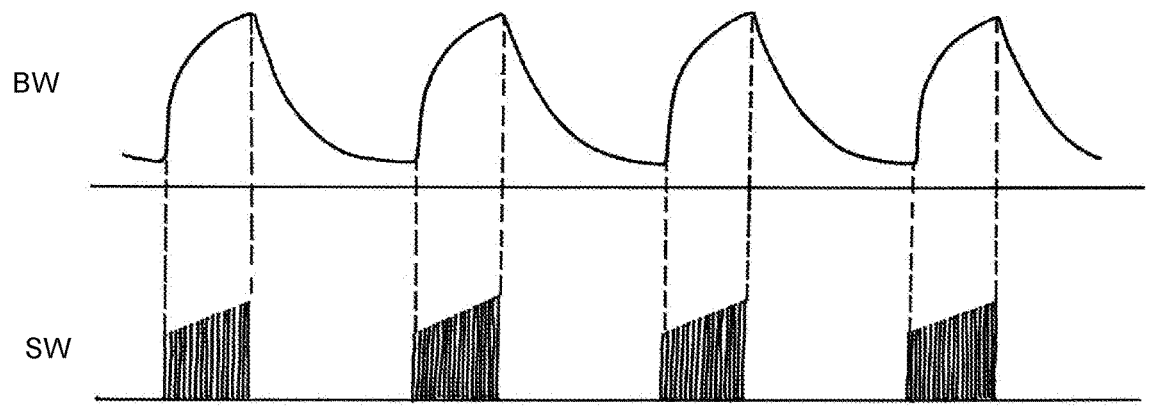
FIG. 36 shows a portion of a graph of a breathing waveform BW produced by a corresponding stimulation waveform SW having an increasing stimulus amplitude in accordance with embodiments of the present system.

As discussed, FIG. 35 shows a portion of a system graph of a breathing waveform BW produced by a corresponding stimulation waveform SW having a fixed stimulus amplitude in accordance with embodiments of the present system. FIG. 36 shows a portion of a system graph of a breathing waveform BW produced by a corresponding stimulation waveform SW having an increasing stimulus amplitude in accordance with embodiments of the present system.

In accordance with another embodiment of the present system, if the treatment and condition of the patient allow generation of a full breath by the TDS with equivalent tidal volume to that generated solely by the MV, the respiratory rate of the MV may be adjusted to half of what is needed and the TDS, also set at half of the respiratory rate with both may generating breaths alternately, as for example illustrated in FIG. 32. It is further envisioned that the MV could be set to a mode that forces a breath in case the TDS does not produce a stimulation for example due to low battery, electrode failure or one or more of the electrodes becoming dislodged, etc.

In accordance with embodiments of the present system, the stimulator may utilize some form of feedback to properly synchronize the contractions of the diaphragm with the ventilator support from the MV. One method to obtain feedback may include sensors in the tubing which connects the MV to the patient which may sense air flow and air pressure within the tubing as described herein.

Figure 19:
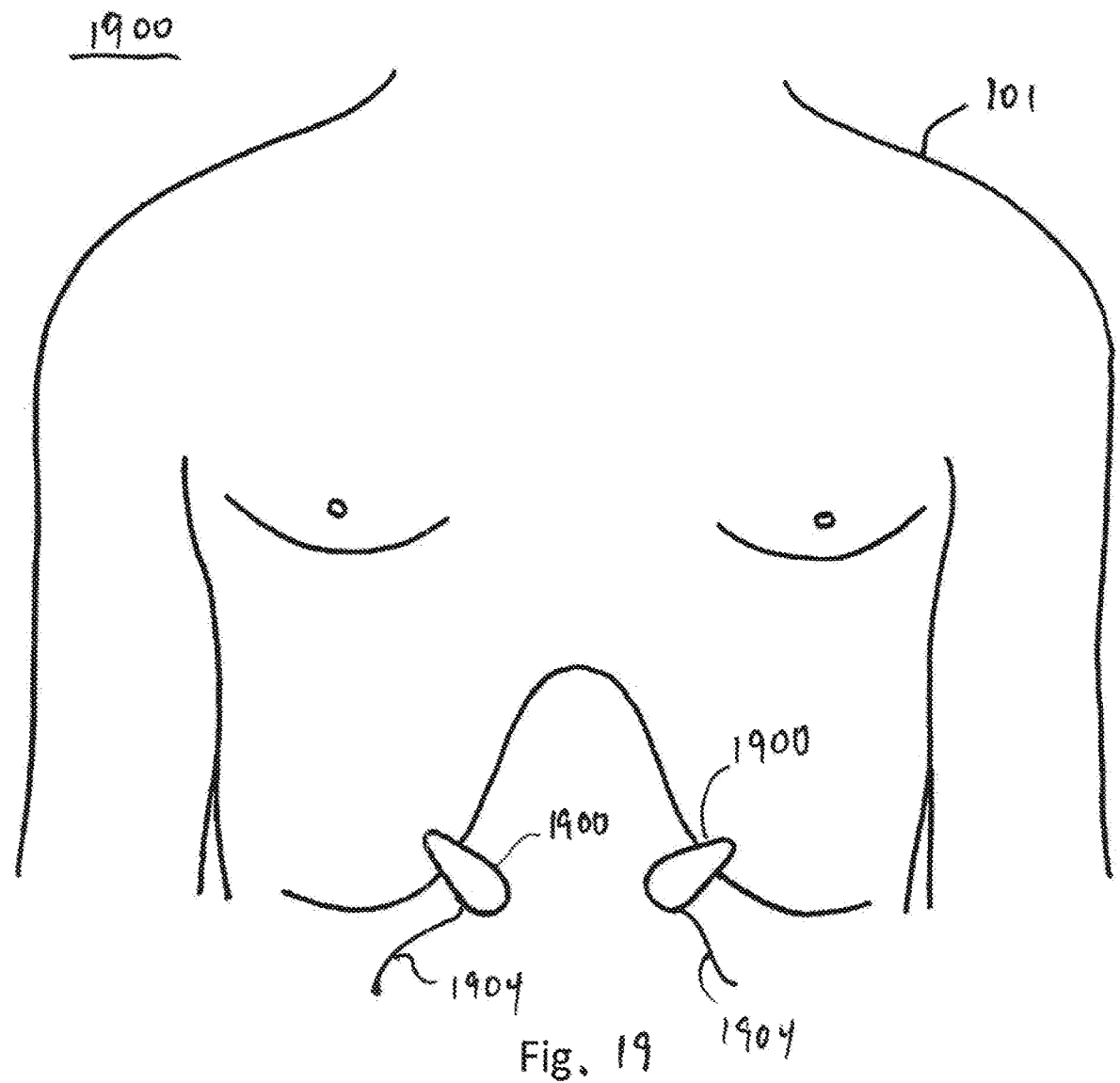
FIG. 19 which shows two sensor patches placed on the skin of the patient between the abdominal and the thoracic regions in accordance with embodiments of the present system.

Further, a method to eliminate wires, tube connections and/or to simplify operation, is also described herein below. In accordance with embodiments of the present system, the stimulator may be synchronized with the MV using sensor information obtained such as via sensor patches. For example, it is envisioned that a plurality of sensor patches such as two sensor patches may be placed on the skin of the patient between the abdominal and the thoracic regions, for example with one on each side. This is illustrated in FIG. 19 which shows two sensor patches 1900 placed on the skin of the patient 101 between the abdominal and the thoracic regions in accordance with embodiments of the present system. Each of these sensors 1900 may be coupled to a stimulator via a wireless or wired communication methods. Accordingly, an antenna may be provided for wireless communication and a communication cable such as cable 1904 may be provided for wired communication.

FIG. 20 shows a top planar view of a portion of the sensor patch 1900 of FIG. 19 in accordance with embodiments of the present system; FIG. 21 shows a front side view of a portion of the sensor patch 1900 of FIG. 20 in accordance with embodiments of the present system; and FIG. 22 shows a bottom planar view of a portion of the sensor patch 1900 of FIG. 19 in accordance with embodiments of the present system. The rear side view of the sensor patch 1900 may be similar to the front side view shown in FIG. 21 and is not shown for the sake of clarity.

With reference to FIG. 20, the sensor patch 1900 may include a power button 2060 and a status indicator 2062. The power button 2060 may be depressed to switch the sensor patch 1900 from an on or off mode (e.g., to toggle) which may turn power on or off, respectively, within at least a portion of the sensor patch 1900.

Figure 38A:
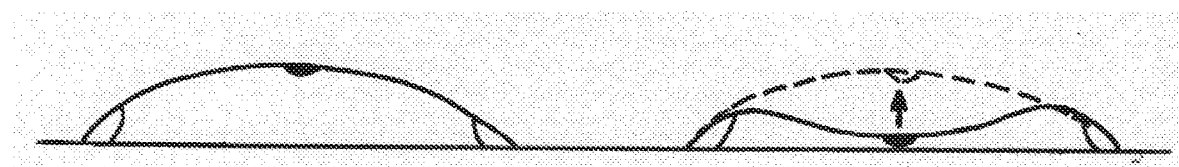
FIG. 38A shows a portion of a sensor button in accordance with embodiments of the present system.

FIG. 38A shows an embodiment of a power button in accordance with embodiments of the present system. As shown, when the button is in an off mode, depression of the button may turn power on a sensor patch in accordance with embodiments of the present system. When the button is depressed again, the button returns to the off mode from the on mode, thereby turning power off to the sensor patch.

Figure 38B:
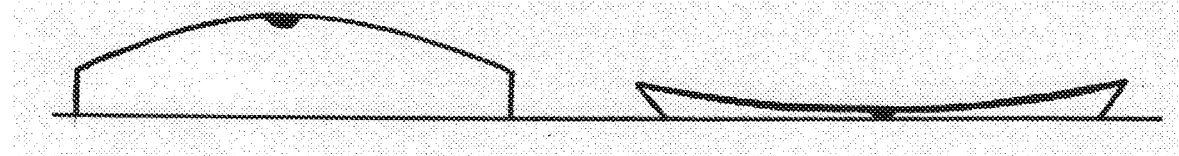
FIG. 38B shows a portion of an alternate sensor button in accordance with embodiments of the present system.

In accordance with embodiments of the present system, the power button 2060 may only be operative to turn on power to ensure that it accidentally doesn't turn off while the patient is pacing with the TDS. FIG. 38B shows an embodiment of a power button in accordance with embodiments of the present system. As shown, when the button is in an off mode, depression of the button may turn power on a sensor patch in accordance with embodiments of the present system, however, once turned to the on mode, the power button cannot return to the off mode. In FIG. 20, a status indicator 2062 may indicate a status of the sensor patch 1900 such as whether it is in an on or off mode. The status indicator 2062 may include a suitable illumination source such as a light emitting diode (LED) which may be illuminated when the sensor patch 1900 is an on mode and not illuminated when in an off mode.

With reference to FIG. 21, the sensor patch 1900 may include a body 1902 having at least one cavity 2064 within which control circuitry and a power source may be located. The sensor patch 1900 may further include at least one mounting surface such as first and second mounting islands 2066 and 2068, respectively, each of which may have a surface 2070 and 2072, respectively. The sensor patch 1900 may be formed from any suitable material such as first and second layers 2078 and 2076, respectively, which may be coupled to each other using any suitable method such as adhesives, bonds, welds, etc. It is envisioned that the first and second layers 2078 and 2076 respectively, may be formed from any suitable material such as plastic, silicone, polypropylene, thermoplastic polymers, or the like and may be shaped using any suitable method such as thermoforming, molding, etc., and may be sealed with the other layers using methods such as heat, RF, ultrasound, UV-cured epoxy, etc.

With reference to FIG. 22, a first skin pad contact 2071 may be situated within the first mounting island 2066 and a second skin pad contact 2073 may be located within the second mounting island 2068. An adhesive layer 2074 may be situated on a surface 2070 of the first mounting island 2066 and on the surface 2072 of the second mounting island 2068 and may be suitable for coupling the first and second skin pad contacts 2071 and 2073, respectively, to the skin of the patient 101. An adhesive protective backing may be placed over the adhesive layers 2074 for protection during shipping, storage, and/or handling and may be removed prior to use. The adhesive protective backing may be formed from any suitable material such as from any suitable release liner or the like.

During use, the abdominal movement caused by either the MV-generated breath or TDS-generated breath is captured for example by the accelerometer 2080 as vibrations and/or the flexing and displacement of the sensor patch which in response thereto forms corresponding sensor information which may be provided to a controller of the sensor patch 1900. This controller may then process the sensor information and communicate with a controller of the system such as a controller of a stimulator using any suitable wired or wireless communication methods. For example to further minimize connections and simplify operation, these two patches may have bidirectional wireless communication with the stimulator such as via Bluetooth™, Zigbee™, WiFi™, and/or other wired and/or wireless protocol(s).

Figure 23:
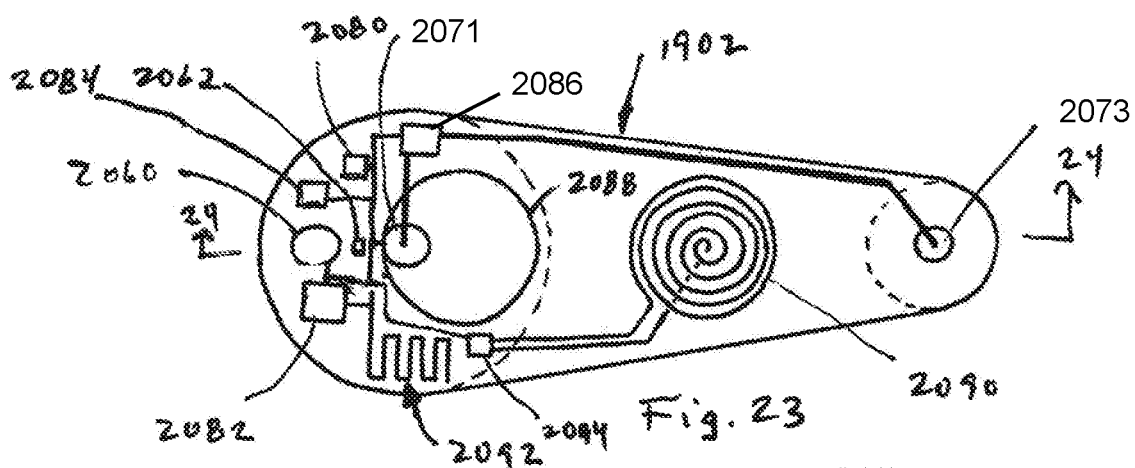
FIG. 23 shows a top planar view of a portion of the sensor patch of FIG. 19 with a transparent first layer in accordance with embodiments of the present system.
Figure 24:
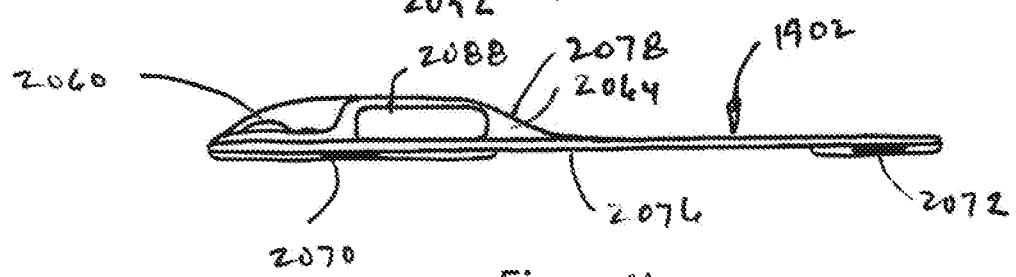
FIG. 24 shows a cutaway side view of a portion of the sensor patch taken along lines 24-24 of FIG. 23 in accordance with embodiments of the present system.

FIG. 23 shows a bottom planar view of a portion of the sensor patch 1900 of FIG. 19 with a first layer 2078 in accordance with embodiments of the present system; and FIG. 24 shows a cutaway side view of a portion of the sensor patch 1900 taken along lines 24-24 of FIG. 23 in accordance with embodiments of the present system. The sensor patch 1900 may include at least one vibration sensor 2080 such as a 3-axis accelerometer, piezoelectric sensor, strain gauge, force sensor, or other technology or types of sensors. The sensor patch may further include a controller such as a microcontroller 2082 and other digital circuits that may read the sensor information from the at least one vibration sensor 2080, filter the sensor information, and transmit the filtered sensor information using any suitable method such as a wireless transmission method to the stimulator for further processing. The sensor patch 1900 may further include an antenna 2092 coupled to the microcontroller 2082 for bidirectional communications with the stimulator. Communications may be performed via any suitable wired and/or wireless link protocol such as via Bluetooth™, Zigbee™, WiFi™, RS-232™, or others. Communications may also be performed via any suitable protocol such as a proprietary protocol specifically designed for this application to minimize power consumption.

The sensor patch 1900 may further include a power supply which may include at least one of a capacitor or at least one battery 2088 that may provide power to one or more portions or circuits within the sensor patch 1900 such as a power bus of the sensor patch which may supply power as may be required within the sensor patch 1900. The at least one battery 2088 may be a rechargeable or non-rechargeable battery as may be desired. Similarly, the at least one battery 2088 may be replaceable or non-replaceable as may be desired.

It is further envisioned that the power supply may include a power conditioner 2084 which may condition power from any source such as from battery 2088, a capacitor, or from a power converter circuit 2094 as discussed below, so that the conditioned power is at a desired characteristics such as voltage, current, waveform, (e.g., DC, AC, etc.), ripple, etc.

The at least one capacitor may include any suitable capacitor with very high capacity such as an electric double-layer capacitor (EDLC) also known as a supercapacitor, or ultracapacitor, which may be recharged using any suitable wired or wireless methods.

The sensor patch 1900 may further include a charging antenna 2090 and the power converter circuit 2094 to convert RF energy into DC current and properly condition this DC current to a desired voltage, etc. to provide conditioned power to the power supply (such as the at least one capacitor, battery, etc.) or other circuits of the sensor patch 1900.

To wirelessly charge the power source or to otherwise supply power to the sensor patch 1900, an external charging loop antenna may be placed over the charging antenna 2090 until fully charged or a desired amount of power is obtained. If an EDLC is used, charging may take only a few seconds. It is envisioned that during charging, sensing operations such as sensing of the breaths and transmission of the data may continue undisturbed by the charging. However, during charging, an isolation circuit may be operative to temporarily disable the charging while the bidirectional wireless transmission between the sensor patch 1900 and the TDS is being performed to prevent any possible disturbance or interference of the transmission.

It is envisioned that while in the packaging, the sensor patch 1900 may be in the off position, all the circuits are unpowered, and no current is drawn from the power supply. After removing the sensor patch 1900 from the packaging and before a release layer is removed from the adhesive protective backing just before the sensor patch 1900 is placed on the skin of the patient, a clinician may depress the power button 2060.

In accordance with embodiments of the present system, the power button 2060 may be a normally-open switch which has two positions, on and off as detailed with reference to FIGS. 38A and 38B. In accordance with embodiments of the present system, this normally-open switch may be a toggle on switch only as shown in FIG. 38B in which case once the power button 2060 is pressed and the sensor patch 1900 is turned to an on mode wherein current starts flowing to the circuits of the sensor patch 1900, the power cannot be turned off. Optionally, an electronic latching circuit can be implemented instead using such button. In this case, a momentary pushbutton will turn on the power to all circuits but after it's released, the electronic latching circuit will guarantee the power is kept on and will not be turned off. In these embodiments, the sensor patch 1900 may only be toggled from the off to the one modes and not vice versa. This may prevent reuse of the sensor patch 1900 which may be disposable after use and guarantees that the sensor is not inadvertently turned off during operation.

After switching to an on mode (e.g., during power up), the status indicator 2062 (e.g., the LED) may indicate a status of the sensor patch 1900 such as whether the power is on (e.g., in the on mode) and/or whether the device is operating properly by flashing a certain number of times, after which the flashing may stop to reduce power draw. The microcontroller 2082 may be powered up and may transmit certain information to the stimulator such as a battery voltage and/or a serial number of the sensor patch 1900 and/or other data to the stimulator such as operational status information indicating the sensor patch 1900 is in the on mode and whether the sensor patch 1900 is operating properly. A rendering device of the stimulator may render information such as the operational status information indicating an operational status of the sensor patch 1900. Accordingly, visual and/or audible information may be rendered by the rendering device to provide a user with an indication of an operational status of the sensor patch 1900.

Once in the on mode, the clinician may select on the TDS which side of the patient 101 the patch has been placed on, i.e., left side or right side of the abdomen of the patient. This selection may be performed using a UI of the stimulator.

The electronics of the sensor patch 1900 may continue to operate by constantly sending sensor information including breathing information wirelessly to the stimulator until the power is exhausted from the power supply. For example, it is envisioned that when a non-rechargeable sensor patch 1900 is used, when the battery 2088 of the power supply is exhausted, the sensor patch 1900 may be removed and disposed of and a new sensor patch 1900 may be applied to the patient. However, if a rechargeable sensor patch 1900 is used, an external charging antenna may be placed over the charging antenna 2090 of the sensor patch 1900 to charge the power battery or capacitor.

The stimulator may determine a power level (or time in use) of a sensor patch 1900 and may render using a rendering device of the stimulator a visual and/or an audible alarm to warn the clinician that the power supply (e.g., the battery 2088) may be low and the sensor patch 1900 may require replacement or, in case of a rechargeable power supply, the sensor patch 1900 may require recharging.

When a new sensor patch 1900 is turned to an on mode, it may transmit its serial number, which may be unique to each sensor patch 1900, to the stimulator. This way the stimulator may recognize that a new patch is being used and may recognize this patch so as to communicate with and/or obtain information from this new sensor patch 1900. After the side of the sensor patch 1900 relative to the patient is selected (e.g., right side, left side, etc.), any data received from the sensor patch 1900 that was previously positioned in the same location as that of the newly recognized patch may be ignored by the stimulator. In other words, once removed from the patient, the removed sensor patch 1900, even if it still has some energy will be ignored as its unique serial number is no longer considered valid by the stimulator. In any case, information transmitted from the removed sensor patch 1900 would be meaningless because it's not picking up the abdominal movements of the patient 101.

The components of all circuits in the sensor patch 1900 may be powered by the power supply such as the battery 2088 for a limited period of time, say one week or other desired time. One week has been found to be satisfactory as some 40% of patients may rely upon MV for four to six days. To extend the life of the battery 2088, the microcontroller 2082 and most circuits of the sensor patch 1900 may operate in a normal mode when sensing and transmitting but, during periods of inactivity, even for brief moments, e.g., periods in the range of microseconds to milliseconds, these circuits may be switched to operate in low-power mode to save as much energy as possible. In this manner, a very small button-type battery can last for one week or more while continuously monitoring the diaphragm activity of a patient, forming corresponding sensor information and transmitting this sensor information to the stimulator for further processing.

The microcontroller 2082 in the sensor patch 1900 may continuously monitor the voltage of the power supply such as the battery 2088. When this voltage is determined to be less than a threshold voltage, it may be determined to be low, and the microcontroller 2082 may be operative to transmit, e.g., via wireless communication, information indicating that the voltage has been determined to be low to the stimulator which may then render information of such on a rendering device for the convenience of a user. Accordingly, a user may be alerted when the battery runs low so that the sensor patch 1900 may be recharged or replaced. The stimulator may recognize from the unique serial number of the sensor patch 1900 whether it has a rechargeable power supply and may be recharged or whether it has a non-rechargeable power supply and should be replaced and may render information indicating such when alerting a user via a user interface (e.g., via a display device) and/or other rendering device (e.g., an audible alert, etc.).

For every breath, the sensor patch 1900 may sense, it may transmit information related to the expansion of the thoracic and abdominal cavity to the stimulator. With this data, the stimulator may be able to accurately calculate the respiratory rate of the MV and correctly synchronize the phrenic nerve stimulation and diaphragm contraction to the proper operation of the MV. It is envisioned that the sensor patch may also send a short series of pulses to synchronize the stimulation with the breath generated by the MV instead of sending the entire data stream. Since the respiratory rate, the tidal volume, and the operation mode of MV rarely changes, the likelihood that the next breath is identical to the previous breath, transmission of data of breaths may be skipped, thereby saving battery power. It is envisioned that the sensor patch continues to read and calculate all parameters of each breath but it will only transmit the information when there are changes compared to the previous breaths. In these embodiments, the microprocessor in the sensor patch may compare readings from a current breadth to the previous data stored in memory. In a case wherein they are identical, the micro-processor may determine there is no need to send the same information related to the thoracic and abdomen movement.

It is further envisioned that the sensor patch may only send a set of pulses to the TDS to synchronize the stimulation of the diaphragm for the next breath meaning the breath is the same as the previous one. This greatly minimizes battery current of the sensor patch. In a case wherein a change in the data recorded for the current breath is different from that data recorded for the previous breath, the entire information may be transmitted to the TDS.

It is also envisioned that the short pulse train may be encoded so that the TDS recognizes it as valid data from one of the sensor patches. The pulse train may also include information identifying which side of the patient the sensor patch that is sending said information is positioned. Further, the information sent by the sensor patch may also include battery level. In this case, the battery level information may be just a short piece of information associated to the battery level, for example, meaning "battery good". In accordance with embodiments of the present system, when the battery is low, the full stream of data may be sent from the sensor patch to the TDS. The sensor patch transmission when power is low may use the same protocol standard of wireless communication such as Bluetooth™, Zigbee™, WiFi™, and/or other wired and/or wireless protocol(s) or optionally may use a proprietary protocol aimed at sending the minimum information with the lowest power consumption compared to that required during transmission with the standard protocol used. The at least one vibration sensor 2080 may detect movement of the patient and its generated data may form a corresponding waveform which may correlate with pressure and timing information due to operation of the MV for example, received from the MV.

Figure 25:
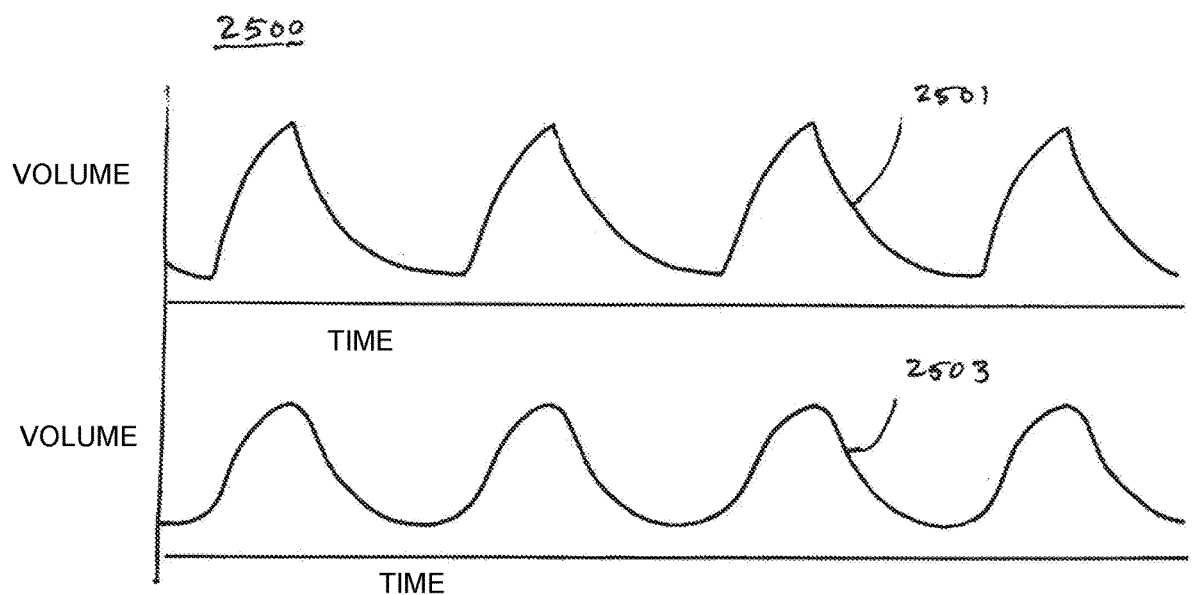
FIG. 25 shows a graph 2500 including portions of breathing waveforms in accordance with embodiments of the present system.

When a MV pumps air into the lungs, the pressure waveform displayed on the MV or a patient monitor normally shows a waveform similar to 2501 of FIG. 25 on which the start and the end of the inspiratory period can be accurately determined. However, the sensor patches don't have a way to directly measure the tidal volume inspired during each breath. With one or more vibration sensors in each sensor patch, the data gathered from them may not show the same waveform because the sensors do not measure pressure inside the lungs but simply measure movement associated with the expansion of the chest and abdominal cavities. Accordingly, a sharp rise at the beginning of the inspiratory period and a sharp drop at the beginning of the expiratory period may not be present in the waveform generated as a result of data received from the vibration sensors because of the physiology of the human body such as elasticity and mechanics of the chest and abdominal walls. It is envisioned that another vibration sensor may pick up the noise generated when air is inspired into the lungs which may be utilized to accurately determine the start and end of the inspiratory period.

In accordance with embodiments of the present system, with the combined data gathered by the two or more sensors, the waveform produced may correlate to the waveform of the MV. The sensor patch waveform shown on 2503 of FIG. 25 shows the same start and end of each inspiratory phase but the exact moments are not well defined. These two start and end points of the inspiratory period can be easily derived through software. The system may employ algorithms (e.g., running in the software) to calculate precise points of the breath waveform so that the beginning and the end of the stimulation starts and ends at the proper moments. For example, FIG. 25 shows a graph 2500 including portions of breathing waveforms in accordance with embodiments of the present system. More particularly, graph 2500 includes a comparison of breathing waveforms (BW) 2501 and 2503 of a patient on support of an MV. However, BW 2501 illustrates a breathing waveform illustrating a volume of air in the lungs over time generated by the MV and displayed by the MV or a patient monitor and BW 2503 illustrates a breathing waveform for the same tidal volume as BW 2501 illustrating the expansion of the thoracic and abdominal cavities over time as detected by the sensor patch in accordance with embodiments of the present system.

FIG. 26A shows a graph 2600A including portions of breathing waveforms as displayed by the TDS in accordance with embodiments of the present system. This graph 2600A includes a plurality of BWs A through H of a patient on support of an MV and a stimulator operating in accordance with embodiments of the present system. BW A shows the MV waveform displayed by the TDS based on signals sent by the sensor patch sensors. Superimposed with BW A are a plurality of BWs B through H displayed when different "fixed" stimulation amplitudes are applied (e.g., see, FIG. 34A). For example, BW B depicts a minimum amplitude which generates a discernible contraction of the diaphragm (threshold amplitude). BWs C through G depict increasing amplitudes of the stimulation waveform that cause an increasing larger diaphragm contraction. BW H depicts the amplitude which is adjusted so that the contraction of the diaphragm generated a peak tidal volume similar or at the same level of that generated by the MV. Waveforms BW B through H show a sharp rise at the beginning of the inspiratory period which demonstrates the contraction of the fast-twitch muscle fibers of the diaphragm.

In accordance with embodiments of the present system, the stimulus pulse train may be programmed to have a certain slope (e.g., see, FIG. 34B-34E). This may be necessary when the condition or the treatment of the patient may better tolerate a more gradual contraction of the diaphragm. FIG. 26B shows a graph 2600B including portions of breathing waveforms as displayed by the TDS in accordance with embodiments of the present system where an increasing amplitude or slope is applied by the stimulator. This graph 2600B includes a plurality of BWs A through H of a patient on support of an MV and a stimulator operating in accordance with embodiments of the present system.

In accordance with embodiments of the present system, the sensor patch 1900 may further include circuitry to measure an action potential created by diaphragm muscle contraction of the patient. The circuitry may be composed of the skin pad contacts 2071 and 2073, an amplifier (e.g., an instrumentation amplifier) and filter 2086 circuit of FIG. 23.

In accordance with embodiments of the present system, the skin pad contacts 2071 and 2073 may be made with silver/silver chloride (Ag/AgCl), widely used to monitor biopotentials (i.e., sensing bioelectric signals), providing a low-DC offset, a high cut-off frequency and very good electrical stability. Other materials are also envisioned. The skin pad contacts 2071 and 2073 capture the action potentials generated by the muscles when they contract. These action potentials are detected when electrical stimulation occurs, not when the abdomen expands due to air being pumped into the lungs by the MV.

The electrodes may be recessed in the sensor patch and may be surrounded by electrolyte gel (i.e., a high viscosity electrolyte solution) or gel-impregnated sponge to reduce the effects of possible motion artifact. This way, the electrolyte adheres directly to the skin, increasing the mechanical stability of the interface between the skin and the electrode. Therefore, the motions detected in the abdominal/thoracic areas by the sensor patch during breathing may cause a minimal impact to the signal being measured.

The analog signal may be amplified, filtered and converted to digital data by the microprocessor which further may encode and send the information wirelessly to the TDS. When a nerve is stimulated or a muscle contracts, a small voltage signal may be generated. This signal, for example in the range between −100 mV to +100 mV, may be measured through the skin and recorded, allowing proper monitoring and diagnosis of parts of the body of the patient. In accordance with yet other embodiments, the sensor patch 1900 may provide electromyography (EMG) information to the stimulator for further processing. As the skin pad contacts 2071 and 2073 pickup the signal measured on the skin surface (e.g., as amplified and filtered), the data contains information related to each stimulus pulse. This way, the sensor patch can send important data to the TDS that may be visualized on the display. In accordance with embodiments of the present system, the data and/or the visualization may be used as a diagnostic tool to ascertain if the electrode is in the proper place or if it was dislodged. A displaced electrode could eventually not stimulate the phrenic nerve and the diaphragm would not contract. It is envisioned that other issues may be determined in accordance with embodiments of the present system. For example, if the biopotentials show a substantially smaller amplitude than previously measured, chances are that the stimulation may not result in proper contraction as before, perhaps due to medications administered to the patient or the patient got an infection such as a pneumonia. In such a case, a suitable message may be generated to alert the clinician.

In accordance with embodiments of the present system, the sensor patch 1900 may provide electrocardiography (ECG) information such as heart rate to the stimulator which can further be analyzed and visualized on the TDS.

It is further envisioned that the sensor patch 1900 may also include other sensors to capture biometric parameters such as an oxygen sensor (e.g., using oximetry to measure the oxygen level (02) or oxygen saturation of the blood), or carbon dioxide sensor (e.g., using transcutaneous carbon dioxide monitoring to measure the blood $CO_2$ level). This information can also be analyzed and visualized on the TDS. Other biometric data such as body temperature can be acquired such as via a temperature sensor, analyzed and visualized. This data can also be used in a feedback system to adjust the TDS as described herein.

It is further envisioned that embodiments of the present system may further employ analysis methods to remotely analyze the condition of the various portions of the system such as lead wires and electrodes using any suitable method such as Transtelephonic Monitoring (TTM) methods or the like, normally used in electrocardiography (ECG) or electromyography (EMG) recordings. If it is determined that there is an action potential sensed between the first and second skin pad contacts 2071 and 2073, respectively, of the sensor patches 1900 positioned on each side of the patient 101 during electrical stimulation, hardware of the stimulator such as the electrode elements (whether surface mounted or implanted) may be determined to be operating properly.

Figure 37:
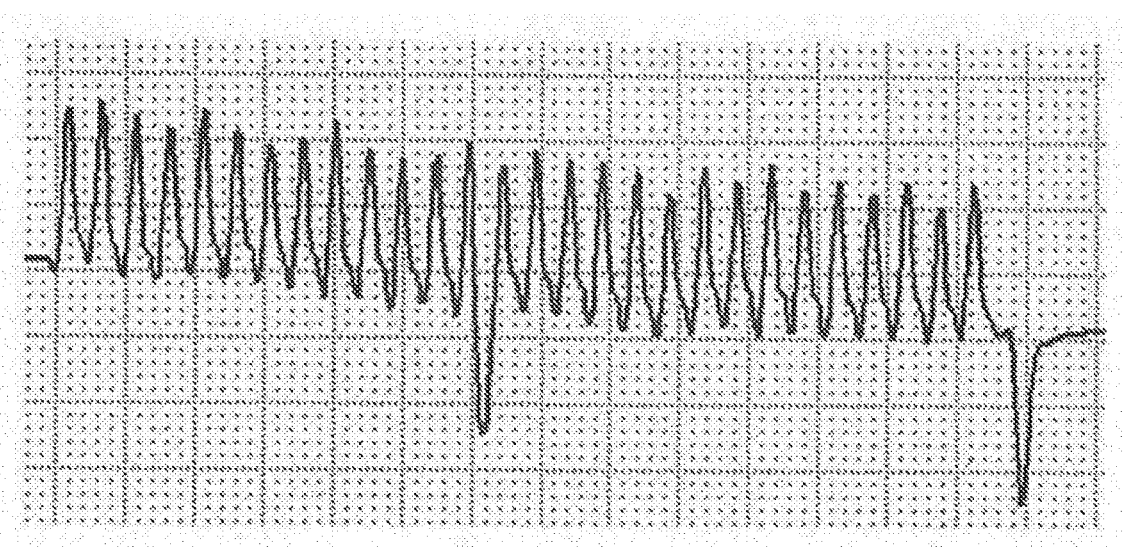
FIG. 37 shows a portion of a waveform captured by skin electrodes conveying a proper contraction of the diaphragm in accordance with embodiments of the present system.

FIG. 37 shows a waveform captured by the two skin electrodes conveying a proper contraction of the diaphragm. Each pulse is related to the action potential generated by the muscle (diaphragm) for each electrical pulse delivered to the phrenic nerve, with its depolarization (rising edge) and polarization (falling edge), normally seen in ECG, EMG and other biopotential recordings. Also seen in FIG. 37 are two negative peaks of larger amplitudes originating from the heart contractions (ECG). In patients chronically implanted with a breathing pacemaker, the waveform such as provided by TTM, may be an invaluable diagnostics tool to confirm the implanted hardware components are working properly. The TDS may detect that one of the stimulating electrodes is properly placed and stimulating the corresponding phrenic nerve but the other stimulating electrode may have been dislodged or moved to a location away from the corresponding phrenic nerve which may not stimulate it properly. For these patients implanted with a breathing pacemaker, at least one skin electrode may be placed on the sternum of the patient (e.g., a reference electrode), and two additional skin electrodes, one on each side of the intercostal area of the patient and which may provide information related to potentials across the corresponding areas of the anatomy of the patient in a manner similar to the skin pads used in an ECG recording. These three electrodes may be coupled to the TTM device which may capture and record the action potentials caused by diaphragm contractions for later analysis.

For temporary pacing applications, the sensing patches may include vibration sensors to detect the inspiratory and expiratory movements. Further, the sensor patches may also include skin electrodes to detect the muscle action potentials or biopotentials, in effect replacing the three skin pads used in the chronically implanted patients as each sensor patch includes one electrode which is the reference electrode and another which is the sensing electrode. In accordance with embodiments of the present system, the sensing patches 1900 may communicate with the stimulator using wireless communication methods, accordingly, there may not be a need for feedback wires coupled from the sensing patches to the stimulator although in accordance with embodiment of the present system wired and/or wireless communication methods may be employed.

More particularly, signals sensed by one or more of the first and second skin pad contacts 2071 and 2073, respectively, such as signals for determining action potential measurements, may be sensed by the first and second skin pad contacts 2071 and 2073, respectively, and analyzed by the microcontroller 2082 to, which may for example, digitize these signals and may determine the action potential of each side of the diaphragm or hemidiaphragm. The microcontroller 2082 may then transmit this information along with identifying information, status information, etc., to the stimulator and/or other portions of the system using any suitable communication method such as wireless and/or wired communication methods, etc. Accordingly, conventional wired electrode patches to determine action potential measurements may not be required when using embodiments of the present system.

In use, part of the sensor patch 1900 may be positioned and located such that it and one of the skin pad contacts (2071 and 2073) included in this part touches the abdominal area and the other part and the other the skin pad contacts (2071 and 2073) included in this part may extend to the thoracic area of the patient to measure the action potentials in the diaphragm, which is located between these two parts of the sensor patch 1900. Accordingly, each side of the sensor patch 1900 may include a skin pad contact (e.g., an electrode) selected from the first and second skin pad contacts 2071 and 2073, respectively, which provides for the collection of action potentials within a corresponding hemidiaphragm in real time and may be represented using analog signals which may be optionally digitized by the microcontroller 2082 before being transmitted to the stimulator and/or other portions of the system such as an electromyography (EMG) system that may be communicatively coupled to one or more of the stimulator and/or sensor patches 1900. It is envisioned that these signals may be rendered in the User Interface of the TDS or other device.

Information from signals generated by the sensor patch 1900, which may include, for example, information related to the action potentials, acceleration information from the accelerometer 2080, battery condition and/or status information, for example which may include information related to a status of the sensor patch 1900 such as power information (e.g., voltage low, time of operation, etc.) and the like may be transmitted via a wireless communication interface link to the stimulator.

The information transmitted by the sensor patch 1900 may be analyzed or otherwise used when adjusting the amplitudes (e.g., of the stimulation pulses) during setup as well as when the stimulator is being synchronized and/or otherwise operating synchronously with the MV. This information may also be useful as a diagnostics tool. For example, in a case wherein a signal is not received (e.g., from the sensor patch 1900), a controller of the system such as a controller of the stimulator may determine that a stimulus electrode or a stimulus patch has been dislodged or otherwise is not making good contact with the patient. Accordingly, the stimulator may generate an alarm and/or render a message on a user interface (UI) indicating such to inform a user that the identified sensor patch 1900 has been dislodged and should be replaced and may identify a position of the sensor patch 1900 relative to the patient 101. For example, if it is determined that the right sensor patch (relative to the patient 101) has been dislodged, a controller of the system may generate and render information such as "right sensor patch has been dislodged reposition patch or replace with new sensor patch".

After the amplitudes of stimulus pulses are adjusted, the stimulation rate and timing are set, and the mode is selected, the stimulator may still need to be enabled to start generating stimulus pulse trains. At any moment during treatment of the patient or when bathing, turning, etc., diaphragmatic stimulation can be halted or paused. It can later be resumed when the clinician finds appropriate.

In accordance with embodiments of the present system, the stimulator may be activated periodically or continuously and, if desired, immediately after the MV begins to provide ventilatory support. Once the patient is able to breathe on his/her own and has been taken off the MV, the stimulating electrodes or the stimulating patches and the sensing patches may be removed and disposed of as desired. In accordance with embodiments of the present system, the sensor patches may detect one or more of the breathing rate and the start of each breath. The selected operating mode generates the required stimulation to prevent diaphragm disuse while the patient is on the MV. Through use of the sensing patches, several breath cycles after the stimulator is enabled, the stimulator may accurately detect the start of each breath and may thereafter stimulate the phrenic nerves for the diaphragm to contract at the proper times according to the selected mode, without disturbing the ventilator support generated by the MV.

The advantages of stimulators according to embodiments of the present system is that besides preventing diaphragm disuse (e.g., VIDD), the device is simple to setup, and may simplify a workflow of caregivers or clinicians who are using embodiments of the present system to prevent a diaphragm of a patient from atrophying. The advantages of exercising the diaphragm at the beginning of the MV support will further reduce the weaning period as discussed. Long term exercise of the diaphragm in patients who were thought to be chronically dependent of the MV may allow them to be completely weaned off from it.

Figure 27:
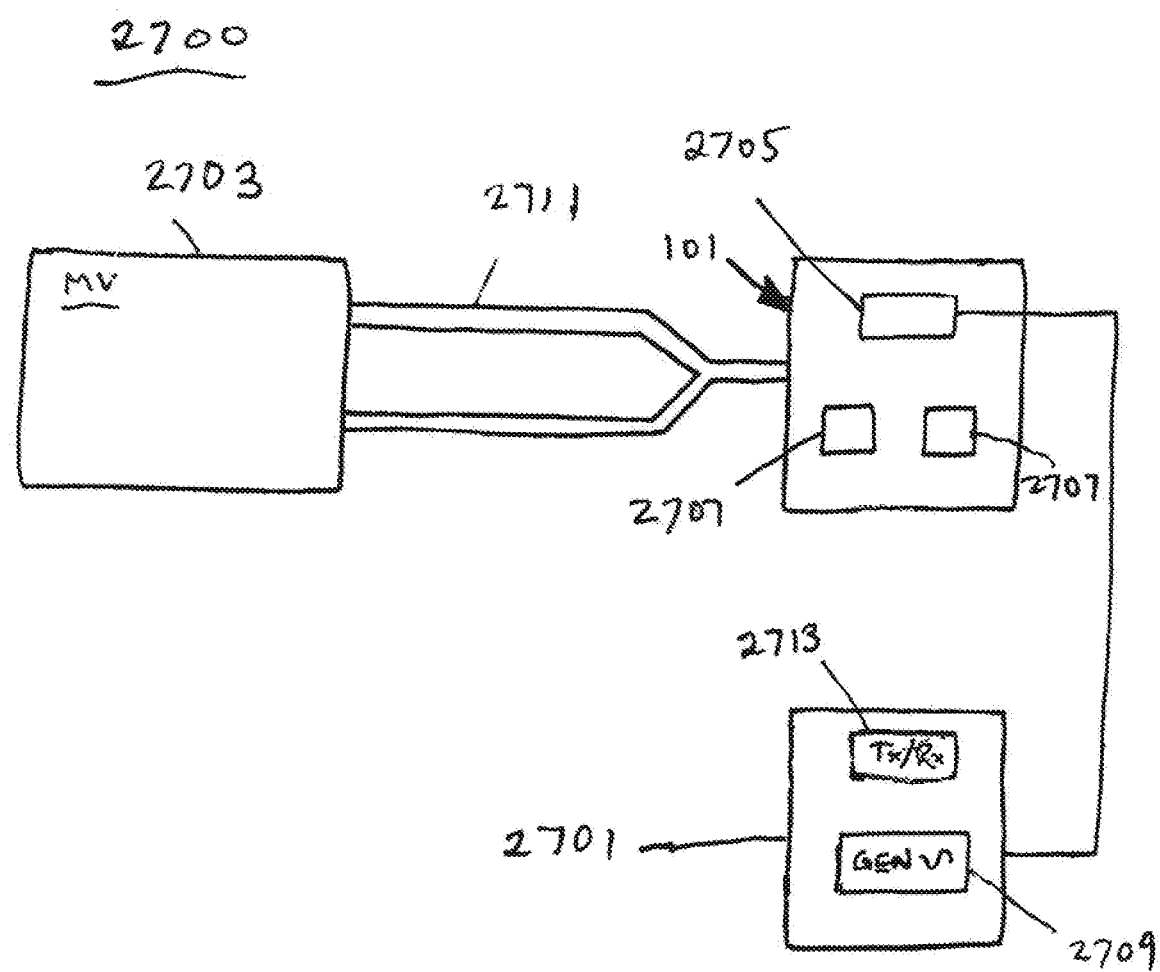
FIG. 27 shows a schematic block diagram of configuration of a stimulation system during operation in accordance with embodiments of the present system.

FIG. 27 shows a schematic block diagram of a configuration of a stimulation system 2700 during operation in accordance with embodiments of the present system. The stimulation system 2700 may include one or more an MV 2703 coupled to a patient 101 via a conduit 2711. A stimulator 2701 such as a TDS stimulator may control a signal generator 2709 to generate a stimulus waveform which may then be transmitted to selected electrode elements 2705 coupled to the patient so as to stimulate the phrenic nerve of the patient 101. Sensors such as wireless sensing patches 2707 may transmit feedback information which may be received by a wireless transmitter/receiver (Tx/Rx) 2713 of the stimulator 2713 and analyzed to determine breathing waveform information of the patient 101 which information may be used to adjust, among other things, the timing of the stimulation waveform. The tubing 2711 may include wye tubing, etc. to connect both the inspiratory circuit and the expiratory circuit of the MV to one common port at the mask or tracheostomy tube of the patient.

Figure 28:
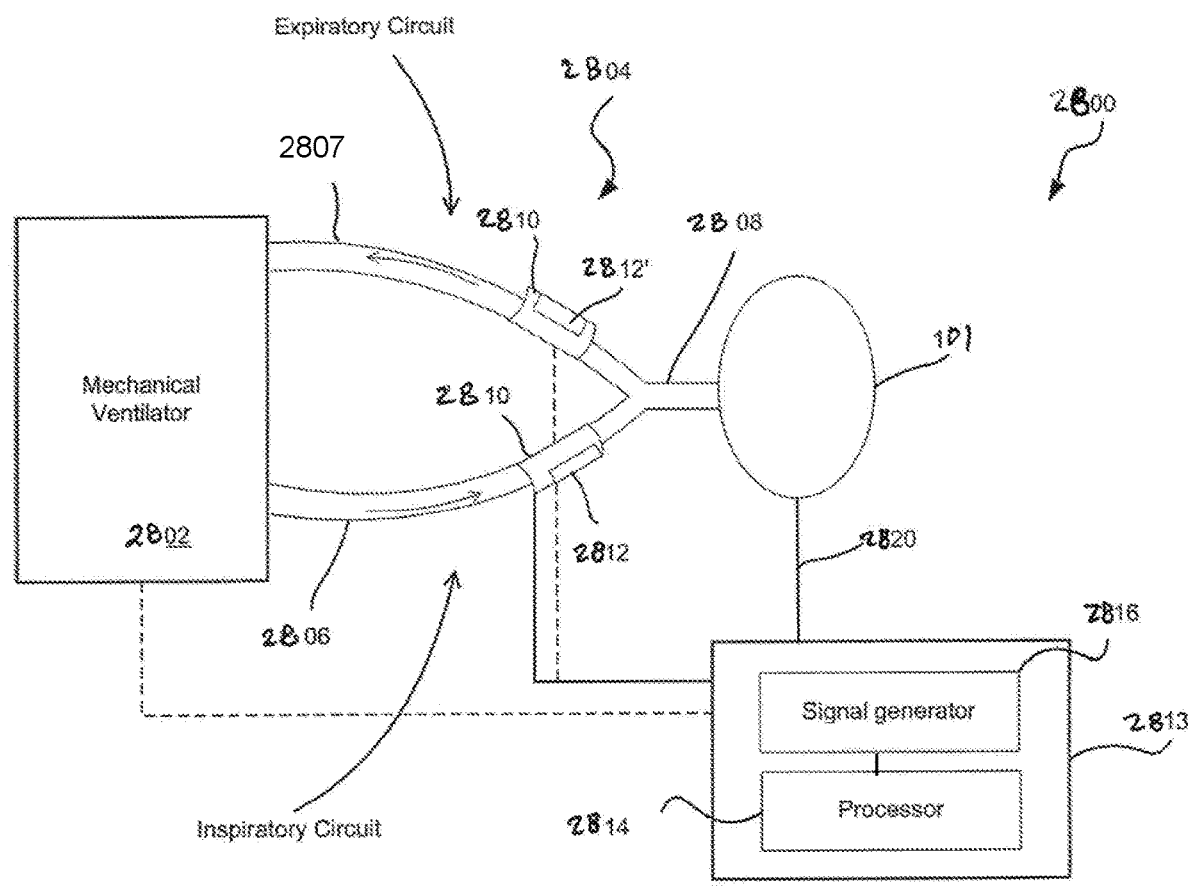
FIG. 28 shows a portion of a schematic block diagram of a system for reducing or substantially preventing VIDD in accordance with embodiments of the present system.

FIG. 28 shows a portion of a schematic block diagram of a system 2800 for reducing or substantially preventing VIDD in accordance with embodiments of the present system. The system 2800 may be implemented in the context of a patient 101 being ventilated under the assistance of a mechanical ventilator 2802 via a ventilation conduit circuit 2804. The conduit circuit 2804 may include an inspiratory conduit 2806 from the mechanical ventilator 2802, an expiratory conduit 2807, and a tracheal tube assembly 2808. The tracheal tube assembly 2808 generally includes one-way valves for controlling one-way flow from the inspiratory conduit 2806 to the patient 101 and from the patient 101 to the expiratory conduit 2807.

The circuit 2804 further includes an adapter 2810 interposed between the inspiratory conduit 2806 and the tracheal tube assembly 2808. The adapter 2810 includes a device 2812 suitable for sensing airflow and pressure between the inspiratory conduit 2806 and the tracheal tube assembly 2808. Any appropriate device can be used in this regard including an electrical sensor and/or a pressure sensor assembly. A further adapter 2810' including a further device 2812' for sensing airflow and pressure in the expiratory flow path may be interposed between the tracheal tube assembly 2808 and the expiratory conduit 2807. In addition, a valve may be provided to reduce pressure in the tracheal tube assembly 2808. With use of this valve, the MV 2802 may be prevented from sensing the negative pressure associated with the TDS-induced breath.

A signal indicative of sensed airflow may be provided from the adapter 2810 (and, optionally, adapter 2810') to stimulator 2813 such as a TDS. For example, the signal from the adapter 2810' may be provided wirelessly or via a wired-line connection. The signal may be a raw sensor output, e.g., a series of pressure readings, voltage readings or resistor values, may be data of the waveform envelope, or may include processed values, e.g., calculated frequency values, phase values, or time values.

In one embodiment, the stimulator 2813 may include a processor 2814 and a stimulus signal generator 2816 operative under the control of the processor 2814. The processor 2814 may receive one or more signals indicative of sensed airflow provided from the adapter 2810 and may determine a signal waveform (e.g., a breathing waveform (BW)) for this signal using any suitable method such as using digital signal processing (DSP) methods or the like. Thereafter, the processor 2814 may determine timing of the BW such as inspiration and expiration phases of a breath of the patient 101. The processor 2814 may then control the signal generator 2816 to produce a stimulus signal that may be applied to the patient 101 in accordance with a selected mode of operation.

For example, in accordance with embodiments of the present system, the processor 2814 may accumulate information from the adapter 2810 and/or adapter 2810' over a number of breathing cycles so as to determine how to drive the signal generator 2816. As shown, the signal generator 2816 may be a portion of a breathing pacemaker or diaphragmatic pacemaker (e.g., the stimulator 2813). The illustrated system 2800 may further include leads 2820 for applying electrical stimuli (e.g., the stimulus signal) to the patient 101.

The processor 2814 may drive the signal generator 2816 such that electrical stimuli are provided to the patient's 101 diaphragm so that the diaphragm does breathing work. That is, the processor 2814 may control the electrical stimulator 2813 such that the stimulator causes the patient's diaphragm to contract and draw air into the patient's lungs due to forces exerted by the patient's diaphragm and not due solely to air forced into the lungs by the mechanical ventilator 2802. For example, the signal generator 2816 operating in accordance with a selected mode of operation may stimulate the diaphragm in-between forced breathing cycles of the ventilator 2802 or in conjunction with forced breathing cycles as discussed above.

Operation of the stimulator 2813 may be accomplished, for example, by manually setting the respiratory rate of the mechanical ventilator 2802 to be about one-half of the desired respiratory rate for the patient 101 or the same respiratory rate set on the MV may be used. The processor 2814 may then control the electrical stimulator 2813 to stimulate diaphragm-controlled breathing cycles in between the MV-forced breathing cycles such that the mechanical ventilator 2802 and electrical stimulator 2813 may collectively yield the desired respiratory rate for the patient 101.

It is further envisioned that, the processor 2814 may receive signals from the mechanical ventilator 2802 and/or may provide control signals to the mechanical ventilator 2802. For example, it is envisioned that the processor 2814 may receive inputs from the ventilator 2802 indicating a respiratory rate setting or other setting of the mechanical ventilator 2802 or may otherwise receive signals indicative of the respiratory rate and/or phase (or may receive signals indicating suspension of ventilator forced breathing). Such signals may be explicitly provided by the mechanical ventilator 2802 and/or may be deduced, for example, by monitoring a drive component of the mechanical ventilator 2802 and/or via sensing patches as described herein. In accordance with embodiments of the present system, the processor 2814 may be operative to provide control signals to the ventilator 2802 to control the rate and/or timing of the breathing cycle or changes thereto.

Figures 39A, 39B:
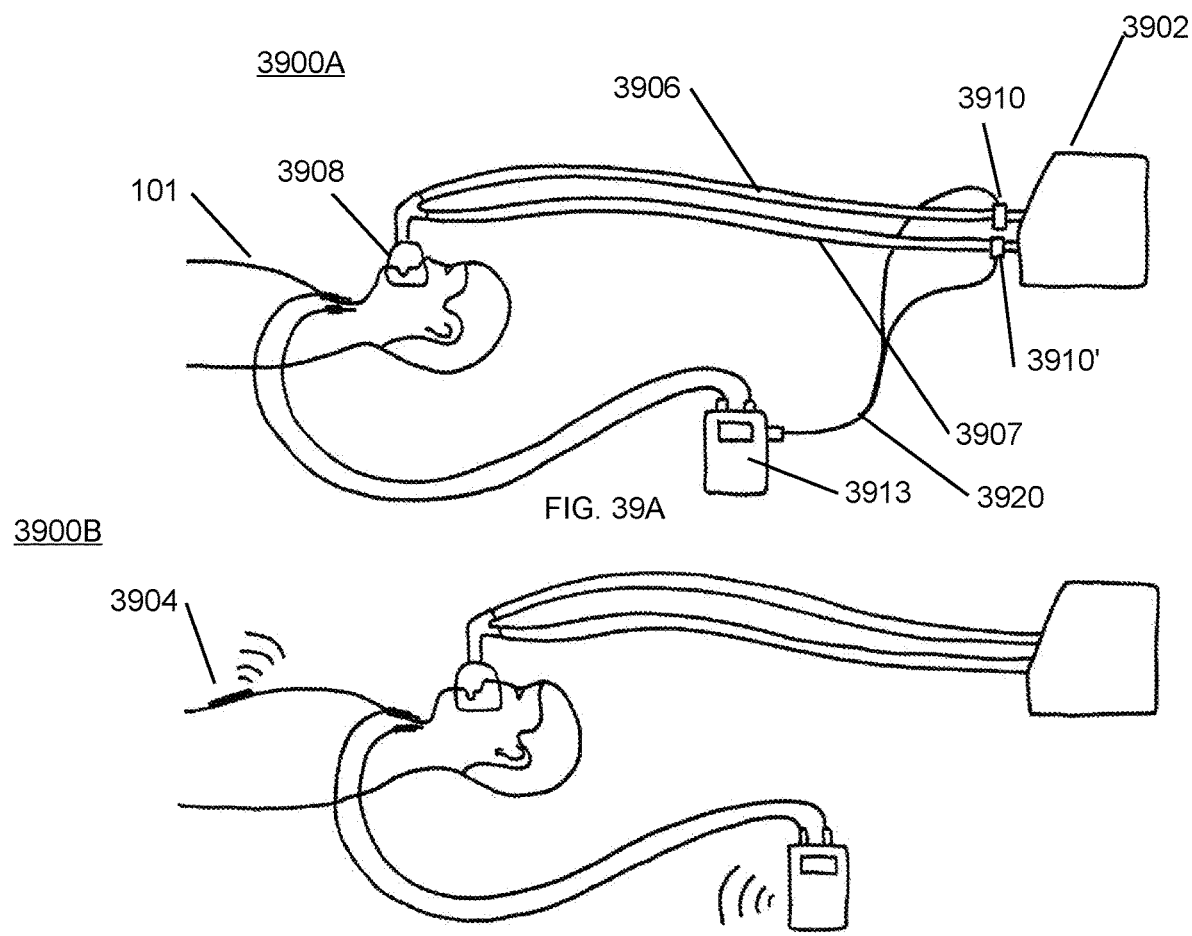
FIG. 39A shows a portion of a system in accordance with embodiments of the present system.
FIG. 39B shows a portion of a system in accordance with embodiments of the present system.

FIG. 39A shows a portion of a schematic block diagram of a system 3900A in accordance with embodiments of the present system. The system 3900A may be implemented in the context of a patient 101 being ventilated under the assistance of a mechanical ventilator 3902 via a ventilation conduit circuit. The conduit circuit may include an inspiratory conduit 3906 from the mechanical ventilator 3902, an expiratory conduit 3907, and a ventilation mask 3908. The circuit 3904 further includes an adapter 3910 interposed between the inspiratory conduit 3906 and the ventilation mask 3908. The adapter 3910 is suitable for sensing airflow and pressure between the inspiratory conduit 3906 and the ventilation mask 3908. Any appropriate device can be used in this regard including an electrical sensor and/or a pressure sensor assembly. A further adapter 3910' may provide for sensing airflow and pressure in the expiratory flow path and may be interposed between the ventilation mask 3908 and the expiratory conduit 3907. In addition, a valve may be provided to reduce pressure in the tracheal tube assembly 3908.

A signal indicative of sensed airflow may be provided from the adapter 3910 (and, optionally, adapter 3910') to a stimulator 3913 such as a TDS. For example, the signal from the adapter 3910' may be provided via a wired-line connection 3920 or may be provided wirelessly. The signal may be a raw sensor output, e.g., a series of pressure readings, voltage readings or resistor values, or may include processed values, e.g., calculated frequency values, phase values, or time values.

FIG. 39B shows a portion of a schematic block diagram of a system 3900B in accordance with embodiments of the present system that is similar to the system 3900A shown in FIG. 39A with the exception that the adapters 3910, 3910' are replaced by sensor patches 3904 that are similar to the sensor patches such as shown in FIG. 19 which transmit sensor signals via a cable and/or wirelessly to the stimulator.

FIG. 29 is a graph 2900 of breathing and stimulus waveforms which illustrate adjustment of each of a mechanical ventilator (MV) and a Temporary Diaphragmatic Stimulator (TDS) to half of a desired respiratory rate such that together the desired respiratory rate is provided to a patient for proper oxygenation/ventilation in this mode of operation in accordance with embodiments of the present system. In this mode, both the MV and the TDS are adjusted to half of the respiratory rate for proper oxygenation/ventilation of the patient. The MV generates one breath and the TDS generates a following (and/or prior) breath with each alternating, thereby providing the breathing stimulus (e.g., air pressure (P) by the MV and TDS Stimulation to provide diaphragm contraction by the TDS). In accordance with embodiments of the present system, the start of each desired breath is calculated by the TDS such that simulation by the TDS is synchronized and starts when the MV would have generated a breath had the TDS not been connected or otherwise been activated to generate a breathing stimulus such that the respiratory rate for proper oxygenation/ventilation of the patient is provided. In the pressure waveform (P), every other breath is crossed out in FIG. 29 and indicated as a TDS BREATH to show the breaths that are provided by the TDS thereby indicating the breaths that are not provided by the MV.

The bottom diagram shows the stimulus pulse train at a maximum amplitude (or a high amplitude) sufficient to generate a full breath with a tidal volume similar to that generated by the MV. This TDS stimulation synchronized to the MV ventilation is particularly useful in cases where the MV has no capability to switch to a mode which allows the patient to generate spontaneous breaths. In accordance with the embodiment of the present system, the TDS is able to measure the start of each breath generated by the MV, determine the exact respiratory rate and generate one breath alternately and between two MV breaths. As seen in the volume graph, the volume of the breaths generated by the TDS raises more sharply due to the contraction of the fast-twitch muscle fibers. Optionally, the stimulus pulse train may be programmed to have a certain slope which may be desired when the condition or the treatment of the patient may better tolerate a more gradual contraction of the diaphragm.

As shown in FIG. 29, when the TDS is utilized to fill the lungs, the flow has a much sharper drop because the contraction of the diaphragm is more abrupt, compared to that of the MV. These waveforms may be deduced based on general mechanics and on observation in the operating room and/or visiting or assisting patients using a diaphragmatic pacemaker. With the breath provided by the MV, the air is pumped by a bellows or other device and therefore a more gradual air flow is provided to the lungs while the diaphragm contraction due to electrical stimuli by the TDS (shown as TDS STIMULATION) in accordance with embodiments of the present system is much quicker. Similarly, the Volume waveform (V) shows a sharper rise with the TDS breath than provided by the MV. While a pressure waveform is not shown for the TDS, it would be opposite to what the MV generates because the TDS causes a negative pressure based on contraction of the diaphragm. The amplitude and/or frequency of the TDS STIMULATION may be set and/or adjusted as described herein.

FIG. 30 is a graph 3000 of breathing and stimulus waveforms which illustrate a mode wherein a TDS generates stimulation (TDS STIMULATION) during the last part of an expiratory time period (ET) of each breath in accordance with embodiments of the present system. In this mode, the TDS generates a relatively low amplitude stimulation (e.g., low TDS STIMULATION compared to that provided in FIG. 29) during the last part of the expiratory time period (ET) of each breath which produces an additional flow (F) and volume (V) to the lungs of the patient caused by the small contraction of the diaphragm in response to the low TDS STIMULATION. This mode of operation does not significantly interfere with the breathing support provided by the MV although, it may be desired that the MV is set to a mode wherein it does not respond to patient breaths such as SIMV or others.

FIG. 31 is a graph 3100 of breathing and stimulus waveforms which illustrate a mode wherein both the MV and the Temporary Diaphragmatic stimulator (TDS) are adjusted to the proper respiratory rate for the patient in accordance with embodiments of the present system. Diaphragmatic stimulation provided by the TDS is synchronized with the MV-provided breath rate and takes place during the inspiratory time period (IT) of each breath. In accordance with embodiments of the present system, a stimulus amplitude provided by the TDS (see, TDS STIMULATION) is set at a relatively low value (e.g., compared to the stimulation provided when the TDS provides the stimulation for a breath by itself such as shown in FIG. 29) to allow some excursion of the diaphragm. In these embodiments, the MV may be set to a mode which is not interfered by the operation of the TDS (e.g., a mode of the MV wherein the breaths are provided by the MV without responding to patient breathing, intake volume, etc.), otherwise the MV may refrain from providing breathing support and the TDS would constantly take over the patient's ventilatory needs. As shown by the solid line compared to the dashed line during the inspiratory time period (IT) of the breathing volume waveform (V), the TDS stimulus generates some additional contraction of the diaphragm shown by the solid line. The dashed line shown in the inspiratory time period (IT) is provided merely to illustrate a difference between breathing with (e.g., see solid line) and without (e.g., see dashed line) the additional breathing support provided by the TDS.

In accordance with embodiments of the present system, a combined mode of operation may be provided wherein two or more of the TDS stimulations shown in FIGS. 29-31 are utilized for stimulating the diaphragm of a patient during breathing support provided by the MV. For example, during operation in accordance with embodiments of the present system, a weak TDS STIMULATION may be provided during an inspiratory time period (IT) as shown in FIG. 31 and a weak TDS STIMULATION may be provided during the end of the expiratory time period (ET) as shown in FIG. 30.

FIG. 32 shows a graph 3200 illustrating breathing and stimulus waveforms in accordance with embodiments of the present system. The top part of FIG. 32 is a graph 3200 of breathing and stimulus waveforms which illustrate a timing diagram of the alternating stimulation of the MV and the TDS in accordance with embodiments of the present system. The bottom part of the diagram illustrates the delay between a breath generated by the MV and a breath generated by the TDS so that the overall respiratory rate is the required rate for the patient to have proper ventilatory support and with the right gas exchange.

Figure 33:
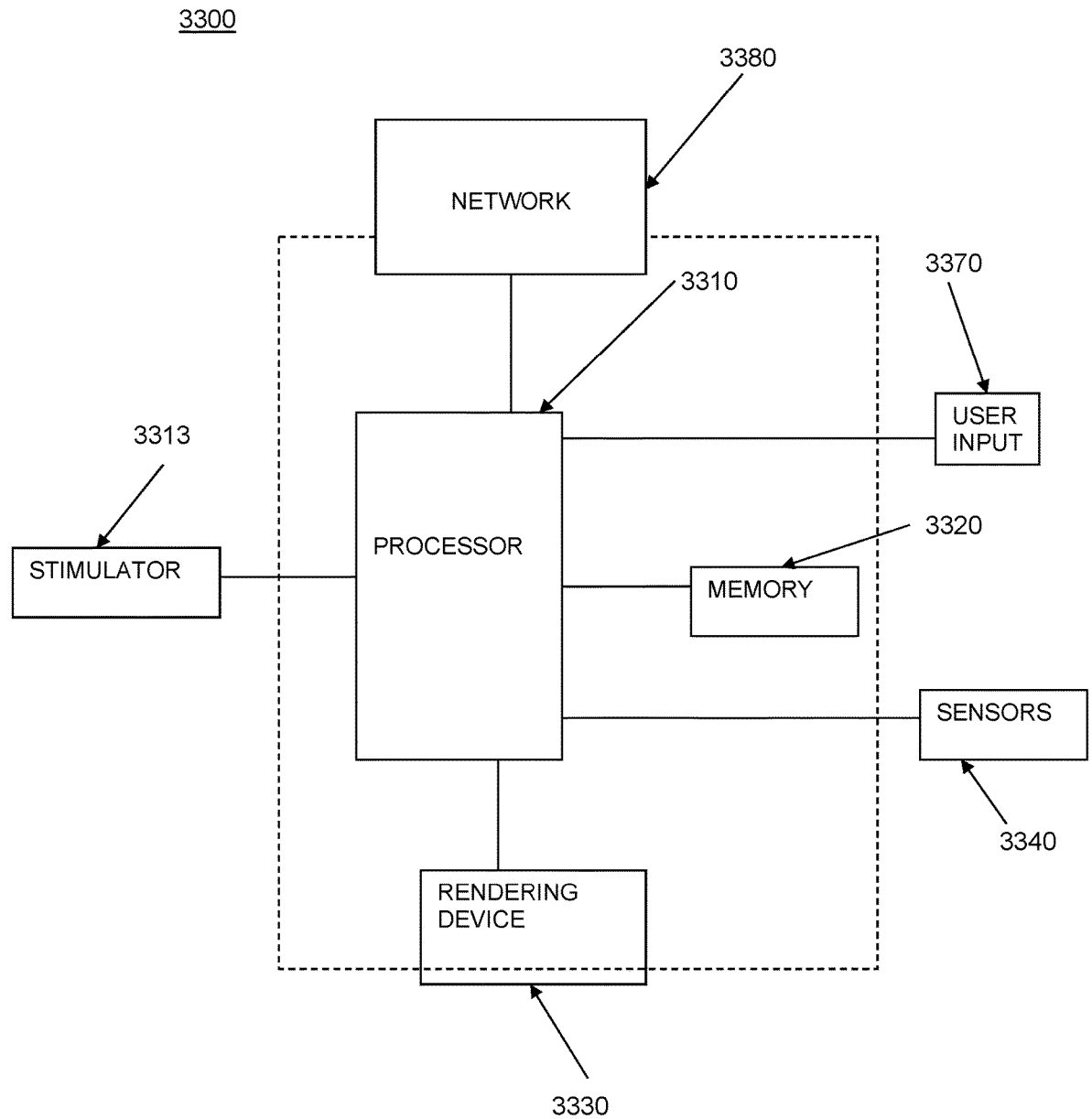
FIG. 33 shows a portion of a system in accordance with embodiments of the present system.

FIG. 33 shows a portion of a system 3300 in accordance with embodiments of the present system. For example, a portion of the present system may include a processor 3310 (e.g., a controller) operationally coupled to a memory 3320, a user interface (UI) including a rendering device such as a display 3330, sensors 3340 (e.g., sensing patches as described herein, see, FIGS. 19-24), and a user input device 3370. The memory 3320 may be any type of device for storing application data as well as other data related to the described operation. The application data and other data are received by the processor 3310 for configuring (e.g., programming) the processor 3310 to perform operation acts in accordance with the present system. The processor 3310 so configured becomes a special purpose machine particularly suited for performing in accordance with embodiments of the present system.

The operation acts may include the processor 3310 configuring the system 3300 to control one or more stimulation and monitoring systems so that sensor information signals indicative of breathing by a patient may be generated. The processor 3310, thereof may process received signals such as sensor information, transform these signals to breathing information (e.g., breathing waveforms, etc.) of a patient, and may analyze this information to determine points in a breathing cycle (e.g., start of inspiratory period, end of inspiratory period, start of expiratory period, end of expiratory period, and/or points within these periods), and control a stimulator system, such as a stimulator 3313 to stimulate a phrenic nerve to exercise a diaphragm of a patient. The processor 3310 may further generate content such as graphs (e.g., still and/or video graphs in real time) including breathing waveforms, stimulator waveforms (of an output pulse train of the stimulator), status information (e.g., on, off, operating modes, errors, etc.) that may be rendered on, for example, a UI of the system such as on the display 3330, a speaker, etc. The content may include image information as may be generated by the present system. Further, the content may then be stored in a memory of the system such as the memory 3320 for later use. Thus, operation acts may include requesting, providing, and/or rendering of content as well as control of the sensors 3340 and the stimulating 3313. The processor 3310 may render the content such as real-time video information on a UI of the system such as a display of the system.

The user input 3370 may include a keyboard, a mouse, a trackball, or other device, such as a touch-sensitive display, which may be stand alone or part of a system, such as part of a personal computer, a personal digital assistant (PDA), a mobile phone (e.g., a smart phone), a monitor, a smart or dumb terminal or other device for communicating with the processor 3310 via any operable link such as a wired and/or wireless communication link. The user input device 3370 may be operable for interacting with the processor 3310 including enabling interaction within a UI as described herein such as setting an operating mode of the stimulator 3313, etc. Clearly the processor 3310, the memory 3320, display 3330, and/or user input device 3370 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 3320 or other memory coupled to the processor 3310.

The program and/or program portions contained in the memory 3320 may configure the processor 3310 to implement the methods, operational acts, and functions disclosed herein. The memories may be distributed, for example between the clients and/or servers, or local, and the processor 3310, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 3310. With this definition, information accessible through a network 3380 is still within the memory, for instance, because the processor 3310 may retrieve the information from the network 3380 for operation in accordance with the present system.

The processor 3310 is operable for providing control signals and/or performing operations in response to input signals from the user input device 3370 as well as in response to other devices of a network and executing instructions stored in the memory 3320. The processor 3310 may include one or more of a microprocessor, an application-specific or general-use integrated circuit(s), a logic device such as a Field-Programmable Gate array (FPGA), etc. Further, the processor 3310 may be a dedicated processor for performing in accordance with the present system or may be a general-purpose processor wherein only one of many functions operates for performing in accordance with the present system. The processor 3310 may operate utilizing a program portion, multiple program segments, or may be a hardware device utilizing a dedicated or multi-purpose integrated circuit. Embodiments of the present system may provide imaging methods to acquire and/or reconstruct images. Suitable applications may include imaging systems such as ultrasound. However, without limitation it should be understood that embodiments of the present system may further include mechanical ventilation (MV) systems, capnograph systems, humidification systems, and electromiography (EMG), and stimulator systems, and/or combinations thereof operating in accordance with embodiments of the present system. Further, embodiments of the present system may be ideally suited for weaning a patient from the support of a MV.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, any section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function;
e) any of the disclosed elements may be comprised of hardware portions (e.g., including discrete and integrated electronic circuitry), software portions (e.g., computer programming), and any combination thereof;
f) hardware portions may be comprised of one or both of analog and digital portions;
g) any of the disclosed devices or portions thereof may be combined together or separated into further portions unless specifically stated otherwise;
h) no specific sequence of acts or steps is intended to be required unless specifically indicated;
i) the term "plurality of" an element includes two or more of the claimed element, and does not imply any particular range of number of elements; that is, a plurality of elements may be as few as two elements, and may include an immeasurable number of elements; and
j) the term and/or and formatives thereof should be understood to mean that only one or more of the listed elements may need to be suitably present in the system in accordance with the claims recitation and in accordance with one or more embodiments of the present system.

REFERENCES

These references are included herewith as if set out in entirety.
1) Healthcare Cost and Utilization Project. 2009 Agency for Healthcare Research and Quality. http://hcupnetahrqqov. Accessed Nov. 23, 2011.
2) Nelson J E, Cox C E, Hope A A, Carson 55. Chronic critical illness. A M J Res Crit Care Med. 2010; 182: 446-454.
3) Esteban A, Frutos F, Tobin M J, Alia I, So/sona J F, Valverdu I, Fernandez R, de la CalMA, Benito
4) Tomas R. A comparison of four methods of weaning patients from mechanical ventilation. Spanish Lung Failure Collaborative Group. N Eng/J Med 1995; 332: 345-350.
5) Esteban A, Alia I, Ibanez J, Benito 5, Tobin M J. Modes of mechanical ventilation and weaning: a national survey of Spanish hospitals. Spanish Lung Failure Collaborative Group. Chest 1994; 106: 1188-1193.
6) N Engl J Med 2008; 358: 1327-1335 Mar. 27, 2008.
7) J of Pacing and Clinical Electrophysiology 25(6) June 2002.
8) Eur Radio/(2010) 20: 659-665.
9) Innovations Volume 6, Number 5, September/October.
10) Kite-Powell, D M et al. Crit Care Nurse Q. November 1996; 19:77-90.
11) Collaborative Practice: Development, Implementation, and Evaluation of a weaning Protocol for Patients Receiving Mechanical Ventilation. Grap, Mary Jo, R N et al. American Journal of Critical Care. September 2003, Vol 12.
12) The epidemiology of mechanical ventilation use in the United States, Hannah Wunsch, M D et al. Crit Care Med 2010 vol. 38, No 10.
13) Modes of Mechanical Ventilation and Weaning: A National Survey of Spanish Hospitals. A. Esteban et al. J. Hosp Infect. 1994; 106:1188-1193.
14) Daily cost of an intensive care unit day: the contribution of mechanical ventilation. Dasta JF1, McLaughlin T P, Mody S H, Piech C T. Crit Care Med. 2005 June; 33(6):1266-71.

What is claimed is:

1. An apparatus for reducing ventilation induced diaphragm disuse in a patient receiving ventilation support from a mechanical ventilator (MV) that provides cyclic ventilation with an inspiratory phase and an expiratory phase during each cycle of the cyclic ventilation, the apparatus comprising:
an electrode array of first and second types and comprising a plurality of electrodes configured to stimulate a phrenic nerve of the patient; and
at least one controller configured to:
identify a type of electrode array from at least two different types, and
generate a stimulus signal for stimulating a phrenic nerve of the patient based upon the identity of the electrode type during the cyclic ventilation provided by the MV, wherein the stimulus signal comprises portions that stimulate the phrenic nerve and portions that do not stimulate the phrenic nerve, wherein the MV contributes to a given pressure, flow and tidal volume that is received by the patient during each cycle of the cyclic ventilation, and wherein the at least one controller is configured to generate the stimulus signal such that there is no modification of the given pressure, flow and tidal volume that is received by the patient between when the phrenic nerve is stimulated by the stimulus signal during the cyclic ventilation and when the phrenic nerve is not stimulated by the stimulus signal during the cyclic ventilation.

2. The apparatus of claim 1, wherein the electrode array of the first and second types comprise a plurality of control pins, wherein the at least one controller is further configured to determine a jumper setting to identify the type of electrode array, and wherein the jumper setting comprises a wired connection between at least two of the plurality of control pins.

3. The apparatus of claim 1, wherein the at least one controller is further configured to control an amplitude of the stimulus signal in accordance with the identified type of electrode array.

4. The apparatus of claim 1, wherein the at least one controller is further configured to obtain breathing cycle information indicative of at least one of the inspiratory phase and the expiratory phase of the cyclic ventilation provided by the MV and is configured to generate the stimulus signal during both the inspiratory and expiratory phases.

5. The apparatus of claim 4, wherein the at least one controller is further configured to discontinue a repetition of the stimulus signal for one ventilation cycle following a plurality of ventilation cycles provided by the MV.

6. The apparatus of claim 4, comprising a sensor coupled to the controller and configured to determine the breathing cycle information, wherein the at least one controller is further configured to identify an identifier (ID) of the sensor which determines the breathing cycle information.

7. The apparatus of claim 6, further comprising a display operatively coupled to the at least one controller, wherein the at least one controller is further configured to:
determine a battery type of the identified sensor as one of a rechargeable or non-rechargeable battery based on the identifier (ID),
determine an operating state of the rechargeable or non-rechargeable battery, and
provide an indication on the display of the battery type and the operating state.

8. A method for reducing ventilation induced diaphragm disuse in a patient receiving ventilation support from a mechanical ventilator (MV) that provides cyclic ventilation with an inspiratory phase and an expiratory phase during each cycle of the cyclic ventilation, the method comprising acts of:
a processor
identifying a type of electrode array coupled to a patient from at least two different possible electrode types, and
generating a stimulus signal for stimulating a phrenic nerve of the patient during the cyclic ventilation provided by the MV based upon the identification of the electrode type, wherein the stimulus signal comprises portions that stimulate the phrenic nerve and portions that do not stimulate the phrenic nerve, the MV contributing to a given pressure, flow and tidal volume that is received by the patient during each cycle of the cyclic ventilation, and wherein generating the stimulus signal comprises generating the stimulus signal such that there is no modification of the given pressure, flow and tidal volume that is received by the patient between when the phrenic nerve is stimulated by the stimulus signal during the cyclic ventilation and when the phrenic nerve is not stimulated by the stimulus signal during the cyclic ventilation.

9. The method of claim 8, wherein the electrode array of the at least two different possible electrode types comprise a plurality of control pins, wherein the processor performs an act of determining a jumper setting to identify the type of electrode array, and wherein the jumper setting comprises a wired connection between at least two of the plurality of control pins.

10. The method of claim 8, wherein the processor performs an act of controlling an amplitude of the stimulus signal in accordance with the identified type of electrode array.

11. The method of claim 8, wherein the processor performs an act of obtaining breathing cycle information indicative of at least one of the inspiratory phase and the expiratory phase of the cyclic ventilation provided by the MV, wherein generating the stimulus signal comprises generating the stimulus signal during both the inspiratory and expiratory phases.

12. The method of claim 11, wherein the processor performs an act of discontinuing a repetition of the stimulus signal for one ventilation cycle following a plurality of ventilation cycles provided by the MV.

13. The method of claim 11, wherein a sensor determines the breathing cycle information, and wherein the processor performs an act of identifying an identifier (ID) of the sensor which determines the breathing cycle information.

14. The method of claim 13, wherein the processor performs acts of:
determining a battery type of the identified sensor as one of a rechargeable or non-rechargeable battery based on the identifier (ID),
determining an operating state of the rechargeable or non-rechargeable battery, and
providing an indication of the battery type and the operating state.

15. A non-transitory computer readable medium comprising computer instructions which, when executed by a processor, configure the processor to perform a method for reducing ventilation induced diaphragm disuse in a patient receiving ventilation support from a mechanical ventilator (MV) that provides cyclic ventilation with an inspiratory phase and an expiratory phase during each cycle of the cyclic ventilation, the method comprising acts of:
identifying a type of electrode array coupled to a patient from at least two different possible electrode types, and generating a stimulus signal for stimulating a phrenic nerve of the patient during the cyclic ventilation provided by the MV based upon the identification of the electrode type, wherein the stimulus signal comprises portions that stimulate the phrenic nerve and portions that do not stimulate the phrenic nerve, the MV contributing to a given pressure, flow and tidal volume that is received by the patient during each cycle of the cyclic ventilation, and wherein generating the stimulus signal comprises generating the stimulus signal such that there is no modification of the given pressure, flow and tidal volume that is received by the patient between when the phrenic nerve is stimulated by the stimulus signal during the cyclic ventilation and when the phrenic nerve is not stimulated by the stimulus signal during the cyclic ventilation.

16. The medium of claim 15, wherein the electrode array of the at least two different possible electrode types comprise a plurality of control pins, wherein the method includes an act of determining a jumper setting to identify the type of electrode array, and wherein the jumper setting comprises a wired connection between at least two of the plurality of control pins.

17. The medium of claim 15, wherein the method includes an act of controlling an amplitude of the stimulus signal in accordance with the identified type of electrode array.

18. The medium of claim 15, wherein the method includes an act of obtaining breathing cycle information indicative of at least one of the inspiratory phase and the expiratory phase of the cyclic ventilation provided by the MV, wherein generating the stimulus signal comprises generating the stimulus signal during both the inspiratory and expiratory phases.

19. The medium of claim 18, wherein the method includes an act of discontinuing a repetition of the stimulus signal for one ventilation cycle following a plurality of ventilation cycles provided by the MV.

20. The medium of claim 18, wherein a sensor determines the breathing cycle information, and wherein the method includes acts of:

identifying an identifier (ID) of the sensor which determines the breathing cycle information, determining a battery type of the identified sensor as one of a rechargeable or non-rechargeable battery based on the identifier (ID), determining an operating state of the rechargeable or non-rechargeable battery, and providing an indication of the battery type and the operating state.

\* \* \* \* \*